(12) United States Patent
MacDonald et al.

(10) Patent No.: US 11,864,988 B2
(45) Date of Patent: *Jan. 9, 2024

(54) FENESTRATED SHEATH FOR EMBOLIC PROTECTION DURING TRANSCAROTID CAROTID ARTERY REVASCULARIZATION

(71) Applicant: Silk Road Medical, Inc., Sunnyvale, CA (US)

(72) Inventors: Sumaira MacDonald, Sunnyvale, CA (US); Stewart M. Kume, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 93 days.

This patent is subject to a terminal disclaimer.

(21) Appl. No.: 17/470,213

(22) Filed: Sep. 9, 2021

(65) Prior Publication Data

US 2022/0202552 A1  Jun. 30, 2022

Related U.S. Application Data

(63) Continuation of application No. 16/171,784, filed on Oct. 26, 2018, now Pat. No. 11,141,259.
(Continued)

(51) Int. Cl.
*A61F 2/01* (2006.01)
*A61M 25/00* (2006.01)
(Continued)

(52) U.S. Cl.
CPC .............. *A61F 2/014* (2020.05); *A61B 17/12* (2013.01); *A61F 2/954* (2013.01);
(Continued)

(58) Field of Classification Search
CPC ............ A61M 25/005; A61M 25/0051; A61M 25/0052; A61M 25/0053; A61M 1/3613;
(Continued)

(56) References Cited

U.S. PATENT DOCUMENTS

| 4,493,707 A | 1/1985 | Ishihara |
| 4,865,581 A | 9/1989 | Lundquist et al. |

(Continued)

FOREIGN PATENT DOCUMENTS

| EP | 2525742 B1 | 3/2015 |
| JP | H07-265412 A | 10/1995 |

(Continued)

OTHER PUBLICATIONS

U.S. Appl. No. 16/281,311, filed Feb. 21, 2019, US 2019-0388654.
(Continued)

*Primary Examiner* — Thomas McEvoy
(74) *Attorney, Agent, or Firm* — Mintz Levin Cohn Ferris Glovsky and Popeo, P.C.

(57) ABSTRACT

Methods, devices, and systems establish and facilitate retrograde or reverse flow blood circulation in the region of the carotid artery bifurcation in order to limit or prevent the release of emboli into the cerebral vasculature such as into the internal carotid artery. The methods are particularly useful for interventional procedures, such as stenting and angioplasty, atherectomy performed through a transcarotid approach or transfemoral into the common carotid artery, either using an open surgical technique or using a percutaneous technique, such as a modified Seldinger technique or a micropuncture technique.

10 Claims, 31 Drawing Sheets

Related U.S. Application Data

(60) Provisional application No. 62/580,869, filed on Nov. 2, 2017.

(51) Int. Cl.
| | |
|---|---|
| *A61M 25/09* | (2006.01) |
| *A61F 2/954* | (2013.01) |
| *A61B 17/12* | (2006.01) |
| *A61M 25/06* | (2006.01) |
| *A61M 25/10* | (2013.01) |

(52) U.S. Cl.
CPC ........ *A61M 25/0032* (2013.01); *A61M 25/09* (2013.01); *A61M 2025/0008* (2013.01); *A61M 2025/0681* (2013.01); *A61M 2025/1052* (2013.01)

(58) Field of Classification Search
CPC .......... A61M 25/0015; A61M 25/0012; A61M 2025/1052; A61B 17/12022; A61B 17/12027; A61B 17/12031; A61B 17/12036; A61B 17/1204; A61B 17/12109; A61B 17/12136; A61B 5/6866; A61B 2017/1139
See application file for complete search history.

(56) References Cited

U.S. PATENT DOCUMENTS

| | | | |
|---|---|---|---|
| 5,584,803 A | 12/1996 | Stevens et al. |
| 5,727,594 A | 3/1998 | Choksi |
| 5,769,830 A | 6/1998 | Parker |
| 5,916,193 A | 6/1999 | Stevens et al. |
| 6,033,413 A | 3/2000 | Mikus et al. |
| 6,152,912 A | 11/2000 | Jansen et al. |
| 6,161,547 A | 12/2000 | Barbut |
| 6,165,199 A | 12/2000 | Barbut |
| 6,197,014 B1 | 3/2001 | Samson et al. |
| 6,206,868 B1 | 3/2001 | Parodi |
| 6,312,444 B1 | 11/2001 | Barbut |
| 6,383,172 B1 | 5/2002 | Barbut |
| 6,413,235 B1 | 7/2002 | Parodi |
| 6,423,032 B2 | 7/2002 | Parodi |
| 6,527,746 B1 | 3/2003 | Oslund et al. |
| 6,540,712 B1 | 4/2003 | Parodi et al. |
| 6,558,356 B2 | 5/2003 | Barbut |
| 6,595,953 B1 | 7/2003 | Coppi et al. |
| 6,626,886 B1 | 9/2003 | Barbut |
| 6,673,040 B1 | 1/2004 | Samson et al. |
| 6,682,505 B2 | 1/2004 | Bates et al. |
| 6,824,553 B1 | 11/2004 | Samson et al. |
| 6,837,881 B1 | 1/2005 | Barbut |
| 6,855,136 B2 | 2/2005 | Dorros et al. |
| 6,878,140 B2 | 4/2005 | Barbut |
| 6,887,227 B1 | 5/2005 | Barbut |
| 6,929,634 B2 | 8/2005 | Dorros et al. |
| 6,936,060 B2 | 8/2005 | Hogendijk et al. |
| 7,004,931 B2 | 2/2006 | Hogendijk |
| 7,083,594 B2 | 8/2006 | Coppi |
| 7,108,677 B2 | 9/2006 | Courtney et al. |
| 7,223,253 B2 | 5/2007 | Hogendijk |
| 7,422,579 B2 | 9/2008 | Wahr et al. |
| 7,604,612 B2 | 10/2009 | Ressemann et al. |
| 7,833,259 B2 | 11/2010 | Boatman |
| 8,083,788 B2 | 12/2011 | Acosta et al. |
| 8,157,760 B2 | 4/2012 | Criado et al. |
| 8,545,432 B2 | 10/2013 | Renati et al. |
| 9,126,018 B1 | 9/2015 | Garrison |
| 9,241,699 B1 | 1/2016 | Kume et al. |
| 9,789,242 B2 | 10/2017 | Criado et al. |
| 9,833,555 B2 | 12/2017 | Criado et al. |
| 10,039,906 B2 | 8/2018 | Kume et al. |
| 10,085,864 B2 | 10/2018 | Chou et al. |
| 10,159,479 B2 | 12/2018 | Hentges et al. |
| 10,286,139 B2 | 5/2019 | Criado et al. |
| 10,426,885 B2 | 10/2019 | Criado et al. |
| 2001/0044598 A1 | 11/2001 | Parodi |
| 2002/0052620 A1 | 5/2002 | Barbut |
| 2002/0087119 A1 | 7/2002 | Parodi |
| 2002/0165598 A1 | 11/2002 | Wahr et al. |
| 2002/0173815 A1 | 11/2002 | Hogendijk et al. |
| 2003/0040762 A1 | 2/2003 | Dorros et al. |
| 2003/0050600 A1 | 3/2003 | Ressemann et al. |
| 2003/0069468 A1 | 4/2003 | Bolling et al. |
| 2003/0212304 A1 | 11/2003 | Lattouf |
| 2004/0064179 A1 | 4/2004 | Linder et al. |
| 2005/0124973 A1 | 6/2005 | Dorros et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0222532 A1 | 10/2005 | Bertolero et al. |
| 2005/0228432 A1 | 10/2005 | Hogendijk et al. |
| 2005/0267323 A1 | 12/2005 | Dorros et al. |
| 2006/0106338 A1 | 5/2006 | Chang |
| 2006/0149350 A1 | 7/2006 | Patel et al. |
| 2009/0024072 A1 | 1/2009 | Criado et al. |
| 2009/0048654 A1 | 2/2009 | Chmura et al. |
| 2009/0198172 A1 | 8/2009 | Garrison et al. |
| 2009/0228020 A1 | 9/2009 | Wallace et al. |
| 2009/0254166 A1 | 10/2009 | Chou et al. |
| 2010/0042118 A1 | 2/2010 | Garrison et al. |
| 2010/0191169 A1 | 7/2010 | Chang |
| 2010/0191170 A1 | 7/2010 | Chang |
| 2010/0204684 A1 | 8/2010 | Garrison et al. |
| 2010/0217276 A1 | 8/2010 | Garrison et al. |
| 2010/0228269 A1 | 9/2010 | Garrison et al. |
| 2010/0280431 A1 | 11/2010 | Criado et al. |
| 2011/0004147 A1 | 1/2011 | Renati et al. |
| 2011/0034986 A1 | 2/2011 | Chou et al. |
| 2011/0166496 A1 | 7/2011 | Criado et al. |
| 2011/0166497 A1 | 7/2011 | Criado et al. |
| 2011/0213410 A1 | 9/2011 | Ginn et al. |
| 2012/0136350 A1 | 5/2012 | Goshgarian et al. |
| 2012/0197383 A1 | 8/2012 | Ivancev et al. |
| 2013/0172852 A1 | 7/2013 | Chang |
| 2014/0031925 A1 | 1/2014 | Garrison et al. |
| 2014/0058414 A1 | 2/2014 | Garrison et al. |
| 2014/0135661 A1 | 5/2014 | Garrison et al. |
| 2014/0296769 A1 | 10/2014 | Hyde et al. |
| 2014/0296868 A1 | 10/2014 | Garrison et al. |
| 2015/0025616 A1 | 1/2015 | Chang |
| 2015/0080942 A1 | 3/2015 | Garrison et al. |
| 2015/0141760 A1 | 5/2015 | Chou et al. |
| 2015/0150562 A1 | 6/2015 | Chang |
| 2015/0174368 A1 | 6/2015 | Garrison et al. |
| 2015/0327843 A1 | 11/2015 | Garrison |
| 2016/0128688 A1 | 5/2016 | Garrison et al. |
| 2016/0158044 A1 | 6/2016 | Chou et al. |
| 2016/0158502 A1 | 6/2016 | Kume et al. |
| 2016/0242764 A1 | 8/2016 | Garrison et al. |
| 2016/0271315 A1 | 9/2016 | Chang |
| 2016/0271316 A1 | 9/2016 | Criado et al. |
| 2016/0279379 A1 | 9/2016 | Chang |
| 2016/0296690 A1 | 10/2016 | Kume et al. |
| 2017/0021127 A1 | 1/2017 | Manouchehr et al. |
| 2017/0043141 A1 | 2/2017 | Kume et al. |
| 2017/0136212 A1 | 5/2017 | Garrison et al. |
| 2017/0209260 A1 | 7/2017 | Garrison et al. |
| 2017/0296798 A1 | 10/2017 | Kume et al. |
| 2017/0312491 A1 | 11/2017 | Ryan et al. |
| 2017/0354523 A1 | 12/2017 | Chou et al. |
| 2017/0354803 A1 | 12/2017 | Kume et al. |
| 2017/0361072 A1 | 12/2017 | Chou et al. |
| 2017/0368296 A1 | 12/2017 | Chang |
| 2018/0008294 A1 | 1/2018 | Garrison et al. |
| 2018/0154063 A1 | 6/2018 | Criado et al. |
| 2018/0185614 A1 | 7/2018 | Garrison et al. |
| 2018/0289884 A1 | 10/2018 | Criado et al. |
| 2019/0105439 A1 | 4/2019 | Criado et al. |
| 2019/0125512 A1 | 5/2019 | MacDonald et al. |
| 2019/0150916 A1 | 5/2019 | Hentges et al. |
| 2019/0175885 A1 | 6/2019 | Kume et al. |
| 2019/0231962 A1 | 8/2019 | Criado et al. |

(56) References Cited

U.S. PATENT DOCUMENTS

| | | |
|---|---|---|
| 2019/0254680 A1 | 8/2019 | Chang |
| 2019/0262530 A1 | 8/2019 | Criado et al. |
| 2019/0269538 A1 | 9/2019 | Chou et al. |
| 2019/0350568 A1 | 11/2019 | Garrison |
| 2019/0366070 A1 | 12/2019 | Kume et al. |
| 2019/0388654 A1 | 12/2019 | Chou et al. |
| 2020/0009406 A1 | 1/2020 | Garrison et al. |
| 2020/0015826 A1 | 1/2020 | Chang |
| 2020/0016321 A1 | 1/2020 | Criado et al. |
| 2020/0038576 A1 | 2/2020 | Garrison et al. |
| 2020/0054871 A1 | 2/2020 | Ryan et al. |
| 2020/0108221 A1 | 4/2020 | Chang |
| 2020/0113587 A1 | 4/2020 | Garrison et al. |
| 2020/0170637 A1 | 6/2020 | Garrison et al. |
| 2020/0171277 A1 | 6/2020 | Garrison et al. |
| 2020/0282127 A1 | 9/2020 | Garrison et al. |
| 2020/0297912 A1 | 9/2020 | Criado et al. |
| 2021/0212679 A1 | 7/2021 | Hentges et al. |
| 2021/0228847 A1 | 7/2021 | Kume et al. |
| 2021/0236790 A1 | 8/2021 | Kume et al. |
| 2021/0251634 A1 | 8/2021 | Chang |
| 2021/0290213 A1 | 9/2021 | Garrison |
| 2021/0290257 A1 | 9/2021 | Garrison et al. |
| 2021/0298929 A1 | 9/2021 | Wallace et al. |
| 2021/0299343 A1 | 9/2021 | Criado et al. |
| 2021/0299425 A1 | 9/2021 | Kume et al. |
| 2021/0307945 A1 | 10/2021 | Chou et al. |

FOREIGN PATENT DOCUMENTS

| | | | |
|---|---|---|---|
| JP | H08-071161 A | | 3/1996 |
| JP | 10-052490 A | | 2/1998 |
| JP | H10-033666 A | | 2/1998 |
| JP | 2001-523492 A | | 11/2001 |
| JP | 2002-522149 A | | 7/2002 |
| JP | 2002-543914 A | | 12/2002 |
| JP | 2003-521286 A | | 7/2003 |
| JP | 2003-521299 A | | 7/2003 |
| JP | 2005-523123 A | | 8/2005 |
| JP | 2007-301326 A | | 11/2007 |
| WO | WO-99/25419 A | | 5/1999 |
| WO | WO-99/040945 A2 | | 8/1999 |
| WO | WO-00/76390 A2 | | 12/2000 |
| WO | WO-03/090831 A2 | | 11/2003 |

OTHER PUBLICATIONS

U.S. Appl. No. 16/299,524, filed Mar. 12, 2019, US 2019-0366070.
U.S. Appl. No. 16/353,492, filed Mar. 14, 2019, US 2020-0009406.
U.S. Appl. No. 16/377,663, filed Apr. 8, 2019, US 2019-0231962.
U.S. Appl. No. 16/513,030, filed Jul. 16, 2019, US 2020-0170637.
U.S. Appl. No. 16/544,083, filed Aug. 19, 2019, US 2020-0171277.
U.S. Appl. No. 16/880,594, filed May 21, 2020, US 2020-0282127.
U.S. Appl. No. 17/345,544, filed Apr. 11, 2021, US 2021-0299425.
PCT/US2020/058365, dated Oct. 30, 2020, WO 2021/087363.
PCT/US2020/058588, dated Nov. 2, 2020, WO 2021/087480.
PCT/US2020/061073, dated Nov. 18, 2020, WO 2021/102011.
Alexandrescu et al. (2006) "Filter-protected carotid stenting via a minimal cervical access with transitory aspirated reversed flow during initial passage of the target lesion", J. Endovasc. Ther. 13(2):196-204.
Alvarez et al. (2008). "Transcervical carotid stenting with flow reversal is safe in octogenarians: A preliminary safety study" J. Vasc. Surg. 47:96-100.
Bates M.D., et al. "Reversal of the Direction of Internal Carotid Artery Blood Flow by Occlusion of the Common and External Carotid Arteries in a Swine Model" Catherization and Cardiovascular Intervention 60:270-275 (2003).
Bates, M.D., et al. (2004) "Internal Carotid Artery Flow Arrest/Reversal Cerebral Protection Techniques" The West Virginal Medical Journal, vol. 99:60-63.
Bergeron et al. (1999). "Percutaneous stenting of the internal carotid artery: the European CAST I Study" J. Endovasc. Surg. 6:155-159.
Bergeron P. et al. (1996) "Recurrent Carotid Disease: Will Stents be an alternative to surgery?" J Endovasc Surg; 3: 76-79.
Chang, D.W., et al., "A new approach to carotid angioplasty and stenting with transcervical occlusion and protective shunting: Why it may be a better carotid artery intervention" (J Vasc Surg 2004; 39:994-1002.).
Chang, M.D., "Carotid Angioplasty And Stenting Using Transcervical Occlusion And Protective Shunting Via A Mini Incision In The Neck: A New Technique For Difficult Femoral Access Or Filter Placement May Be The Better Carotid Artery Intervention" 30th Global: Vascular and Endovascular Issues, Techniques and Horizons Symposium, New York, NY, Nov. 20-23, 2003; XXVII 6.1-XXVII 6.2.
Coppi et al. (2005). "PRIAMUS Proximal flow blockage cerebral protection during carotid stenting: Results from a multicenter Italian registry" J. Cardiovasc. Surg. 46:219-227.
Criado et al. (1997) "Evolving indications for and early results of carotid artery stenting" Am. J. Surg.; 174:111-114.
Criado et al. (2004). "Transcervical carotid artery angioplasty and stenting with carotid flow reversal: Surgical technique" J. Vasc. Surg. 18:257-261.
Criado et al. (2004). "Transcervical carotid stenting with internal carotid artery flow reversal: Feasibility and preliminary results" J. Vasc. Surg. 40:476-483.
Criado, et al. (2007). "Transcervical carotid stenting with carotid artery flow reversal: 3-year follow-up of 103 stents." J Vasc Surg 46(5): 864-9.
Criado, F.J., et al., Access strategies for carotid artery intervention. J Invasive Cardiol, 2000. 12(1): p. 61-8.
Criado, M.D., et al. (2004) "Carotid angioplasty with internal carotid artery flow reversal is well tolerated in the awake patient" Journal of Vascular Surgery, 40(1):92-7.
Diethrich et al., (1996). "Percutaneous techniques for endoluminal carotid interventions" J. Endovasc. Surg. 3:182-202.
Henry et al. (1999) "Carotid stenting with cerebral protection: First clinical experience using the PercuSurge GuardWire System" J. Endovasc. Surg. 6:321-331.
Lin et al. (2005) "Protected carotid artery stenting and angioplasty via transfemoral versus transcervical approaches" Vasc. Endovasc. Surg. 39(6):499-503.
Lo et al. (2005) "Advantages and indications of transcervical carotid artery stenting with carotid flow reversal" J. Cardovasc. Surg (Torino). 46(3):229-239.
MacDonald, S. (2006) "Is there any evidence that cerebral protection is beneficial?" J. Cardiovasc. Surg. 47:127-36.
Matas et al. (2007). "Transcervical carotid stenting with flow reversal protection: Experience in high-risk patients" J. Vasc. Surg. 46:49-54.
Ohki, M.D., et al., "Efficacy of a proximal occlusion catheter with reversal of flow in the prevention of embolic events during carotid artery stenting: An experimental analysis" (J Vasc Surg 2001; 33:504-9).
Parodi (2005). "Is flow reversal the best method of protection during carotid stenting?" J Endovasc. Ther. 12:166-170.
Pipinos et al. (2005). "Transcervical approach with protective flow reversal for carotid angioplasty and stenting" J. Endovasc. Ther. 12:446-453.
Pipinos et al. (2006). "Transcervical carotid stenting with flow reversal for neuroprotection: Technique, results, advantages, and limitations" 14(5):245-255.
Ribo et al. (2006). "Transcranial doppler monitoring of transcervical carotid stenting with flow reversal protection: a novel carotid revascularization technique" 27:2846-2849 (originally published online Sep. 28, 2006).
Stecker et al., (2002). "Stent placement in common carotid and internal carotid artery stenoses with use of an open transcervical approach in a patient with previous endarterectomy" J. Vasc. Interv. Radiol. 13:413-417.
Stejskal et al., "Experience of 500 Cases of Neurophysiological Monitoring in Carotid Endarterectomy", Acta Neurochir, 2007, 149:681-689.

(56) References Cited

OTHER PUBLICATIONS

U.S. Appl. No. 14/227,585, filed Mar. 27, 2014, US 2014-0296769.
U.S. Appl. No. 15/049,637, filed Feb. 22, 2016, US 2016-0242764.
U.S. Appl. No. 15/399,638, filed Jan. 5, 2017, US 2017-0209260.
U.S. Appl. No. 16/530,783, filed Aug. 2, 2019, US 2020-0054871.
U.S. Appl. No. 16/894,474, filed Jun. 5, 2020, US 2020-0297912.
U.S. Appl. No. 16/906,457, filed Jun. 19, 2020, US 2020-0397472.
U.S. Appl. No. 16/939,396, filed Jul. 27, 2020, US 2020-0397446.
U.S. Appl. No. 16/951,767, filed Nov. 18, 2020, US 2021-0145453.
U.S. Appl. No. 16/999,634, filed Aug. 21, 2020, US 2020-0375728.
U.S. Appl. No. 16/999,640, filed Aug. 21, 2020, US 2020-0375729.
U.S. Appl. No. 17/000,004, filed Aug. 21, 2020, US 2020-0390438.
U.S. Appl. No. 17/074,299, filed Oct. 19, 2020, US 2021-0205571.
U.S. Appl. No. 17/092,635, filed Nov. 9, 2020, US 2021-0228847.
U.S. Appl. No. 17/108,711, filed Dec. 1, 2020, US 2021-0212679.
U.S. Appl. No. 17/149,450, filed Jan. 14, 2021, US 2021-0298929.
U.S. Appl. No. 17/179,746, filed Feb. 19, 2021, US 2021-0244522.
U.S. Appl. No. 17/193,962, filed Mar. 5, 2021, US 2021-0290257.
U.S. Appl. No. 17/206,665, filed Mar. 19, 2021, US 2021-0307945.
U.S. Appl. No. 17/220,718, filed Apr. 1, 2021, US 2021-0290213.
U.S. Appl. No. 17/237,911, filed Apr. 22, 2021, US 2021-0236790.
U.S. Appl. No. 17/307,359, filed May 4, 2021, US 2021-0322738.
U.S. Appl. No. 17/308,199, filed May 5, 2021, US 2021-0251634.
U.S. Appl. No. 17/345,502, filed Jun. 11, 2021, US 2021-0299343.
U.S. Appl. No. 17/345,544, filed Jun. 11, 2021, US 2021-0299425.
U.S. Appl. No. 17/398,969, filed Aug. 10, 2021, US 2022-0047267.
U.S. Appl. No. 17/406,822, filed Aug. 19, 2021, US 2022-0040502.
U.S. Appl. No. 17/555,127, filed Dec. 17, 2021, US 2022-0193321.
U.S. Appl. No. 17/684,745, filed Mar. 2, 2022, US 2023-0045964.
U.S. Appl. No. 17/749,423, filed May 20, 2022, US 2023-0001161.
U.S. Appl. No. 17/749,454, filed May 20, 2022, US 2023-0097442.
U.S. Appl. No. 17/773,200, filed Apr. 29, 2022, US 2022-0401111.
U.S. Appl. No. 17/773,206, filed Apr. 29, 2022, US 2022-0378565.
U.S. Appl. No. 17/899,279, filed Aug. 30, 2022, US 2023-0067426.
U.S. Appl. No. 17/951,727, filed Sep. 23, 2022, US 2023-0101242.
U.S. Appl. No. 18/071,323, filed Nov. 29, 2022, US 2023-0165696.
PCT/US2022/033588, dated Jun. 15, 2022, WO 2022/266195.
PCT/US2022/042074, dated Aug. 30, 2022, WO 2023/034325.
PCT/US2022/044533, dated Sep. 22, 2022, WO 2023/049343.
PCT/US2022/050714, dated Nov. 22, 2022, WO 2023/096898.
PCT/US2022/051275, dated Nov. 29, 2022, WO 2023/101982.
PCT/US2022/080992, dated Dec. 6, 2022, WO 2023/107926.

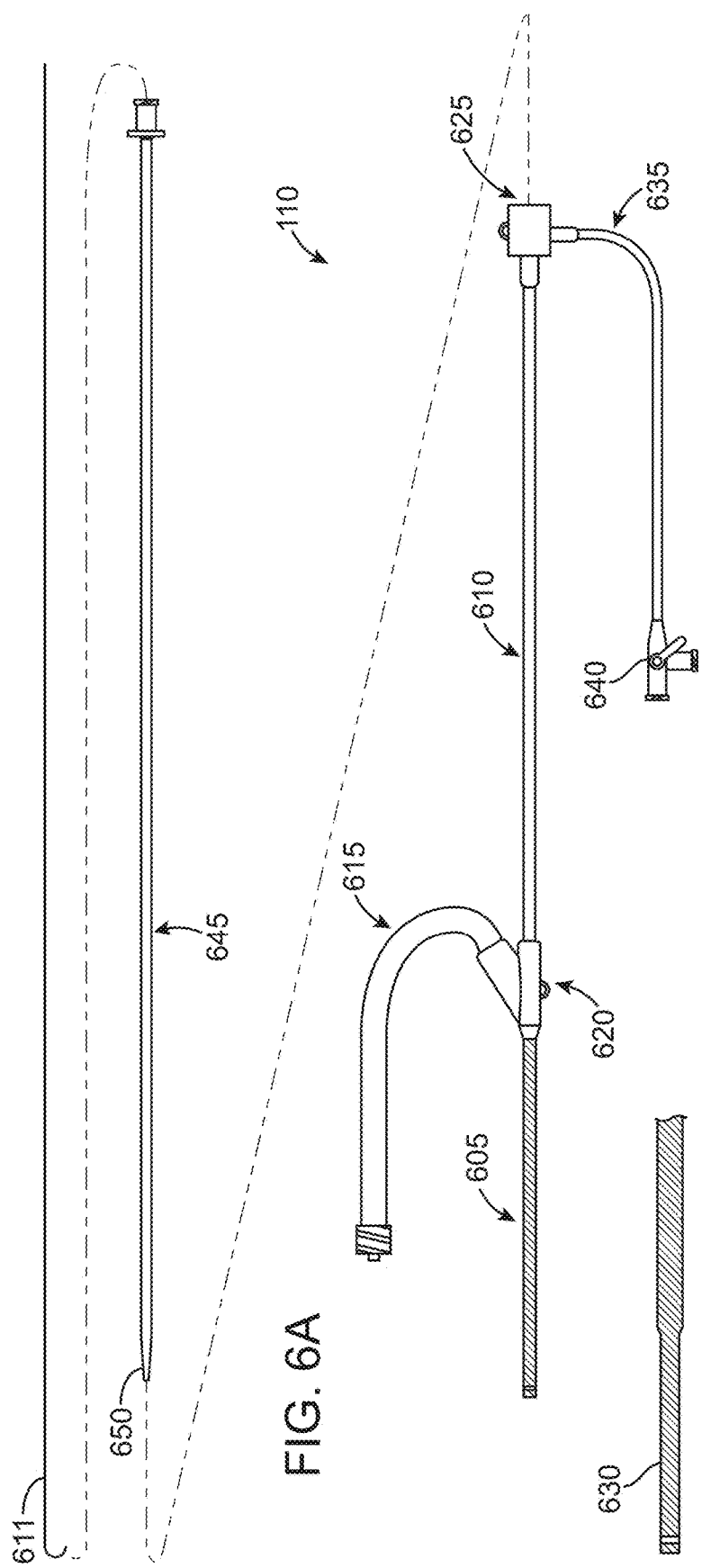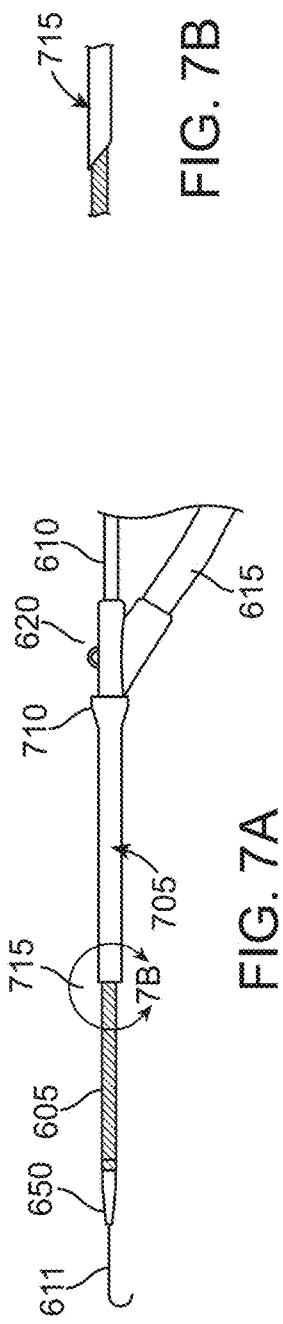

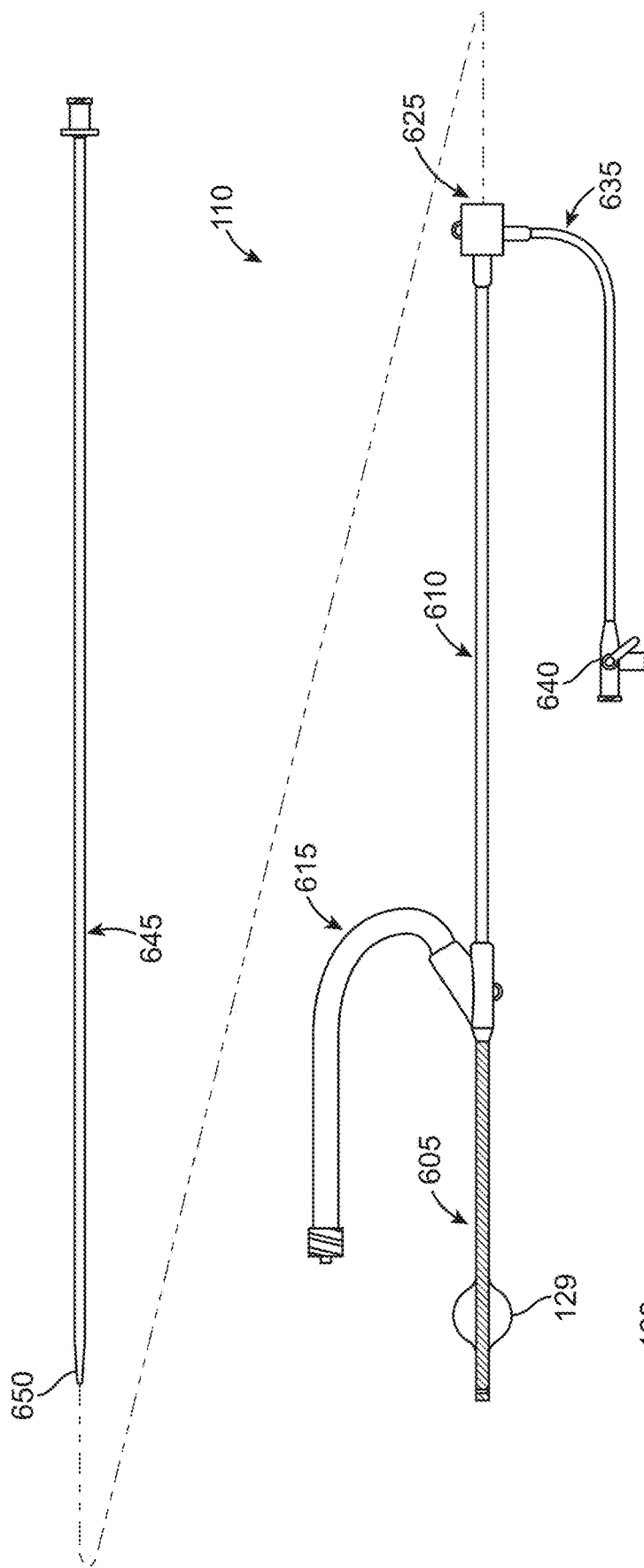
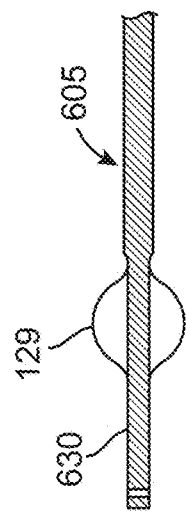
FIG. 8A
FIG. 8B

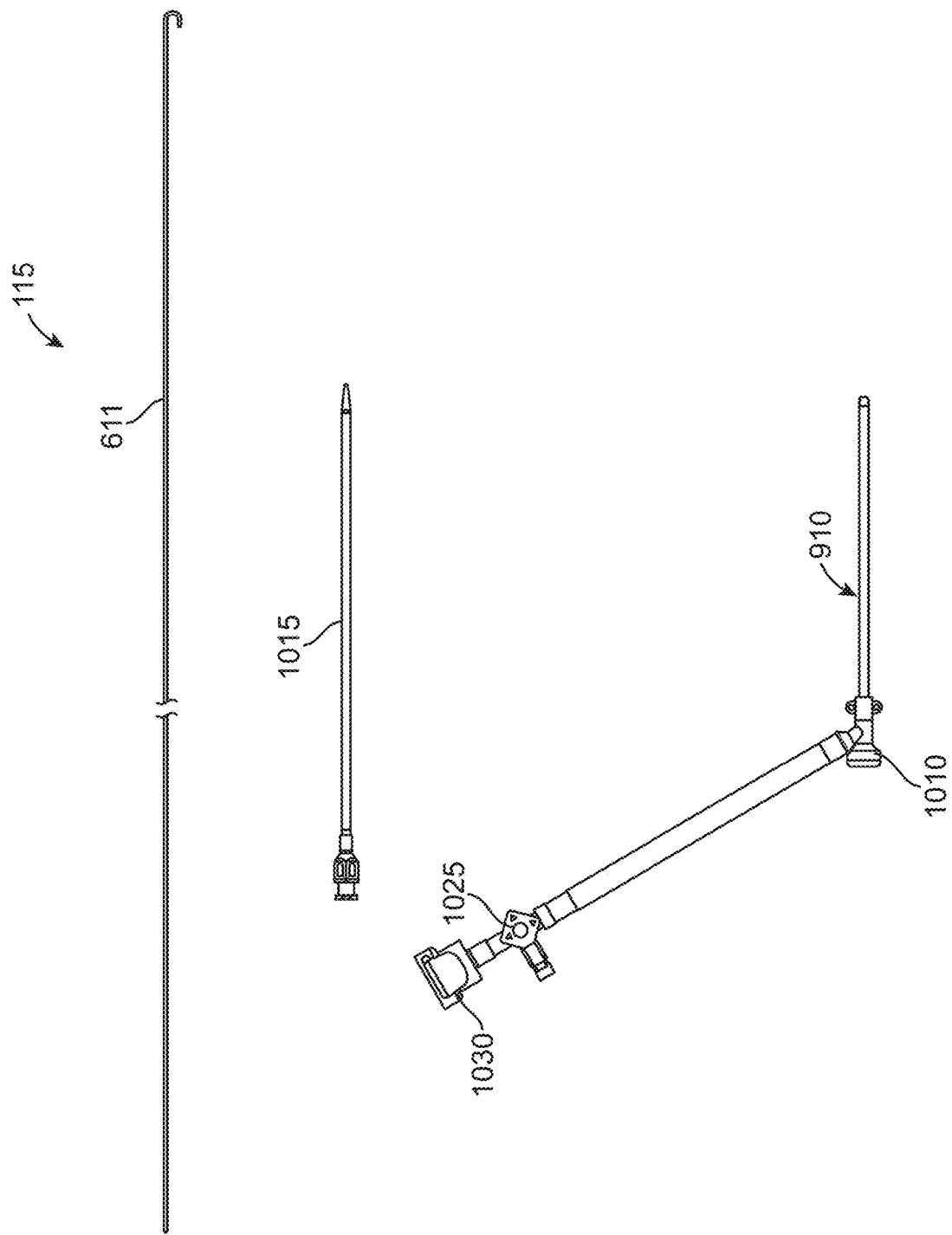

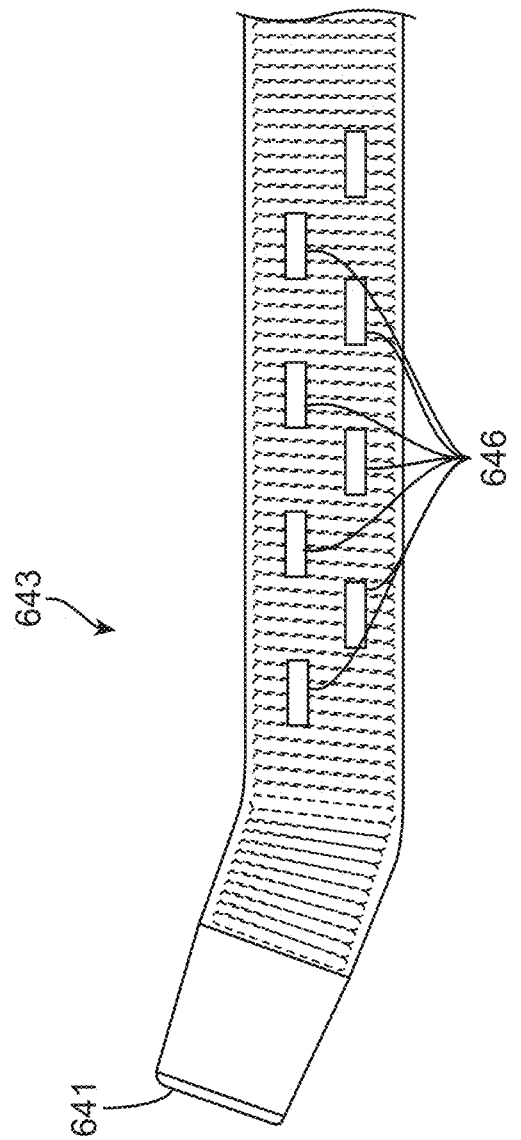

FENESTRATED SHEATH FOR EMBOLIC PROTECTION DURING TRANSCAROTID CAROTID ARTERY REVASCULARIZATION

CROSS-REFERENCE TO RELATED APPLICATION

This application is a continuation of U.S. patent application Ser. No. 16/171,784 filed on Oct. 26, 2018, and claims priority to U.S. Provisional Patent Application Ser. No. 62/580,869 filed on Nov. 2, 2017 and entitled "FENESTRATED SHEATH FOR EMBOLIC PROTECTION DURING TRANSCAROTID CAROTID ARTERY REVASCULARIZATION" the disclosure of these are incorporated herein by reference in their entirety.

BACKGROUND

The present disclosure relates generally to medical methods and devices. More particularly, the present disclosure relates to devices for use during carotid arterial vasculature and establishing retrograde blood flow during performance of carotid artery stenting and other procedures.

Carotid artery disease usually consists of deposits of plaque P which narrow the junction between the common carotid artery CCA and the internal carotid artery ICA, an artery which provides blood flow to the brain (FIG. 5). These deposits increase the risk of embolic particles being generated and entering the cerebral vasculature, leading to neurologic consequences such as transient ischemic attacks TIA, ischemic stroke, or death. In addition, should such narrowings become severe, blood flow to the brain is inhibited with serious and sometimes fatal consequences.

Two principal therapies are employed for treating carotid artery disease. The first is carotid endarterectomy CEA, an open surgical procedure which relies on occluding the common, internal and external carotid arteries, opening the carotid artery at the site of the disease (usually the carotid bifurcation where the common carotid artery CCA divides into the internal carotid artery ICA and external carotid artery ECA), dissecting away and removing the plaque P, and then closing the carotid artery. The second procedure relies on stenting of the carotid arteries, referred to as carotid artery stenting CAS, typically at or across the branch from the common carotid artery CAA into the internal carotid artery ICA, or entirely in the internal carotid artery. Usually, a self-expanding stent is introduced through percutaneous puncture into the femoral artery in the groin and up the aortic arch into the target common carotid artery CCA.

In both these approaches, the patient is at risk of emboli being released into the cerebral vasculature via the internal carotid artery ICA. The clinical consequence of emboli release into the external carotid artery ECA, an artery which provides blood to facial structures, is less significant. During CEA, the risk of emboli release into the internal carotid artery ICA is minimized by debriding and vigorously flushing the arteries before closing the vessels and restoring blood flow. During the procedure while the artery is opened, all the carotid arteries are occluded so particles are unable to enter the vasculature.

In carotid stenting CAS procedures, adjunct embolic protection devices are usually used to at least partially alleviate the risk of emboli. An example of these devices are distal filters, which are deployed in the internal carotid artery distal to the region of stenting. The filter is intended to capture the embolic particles to prevent passage into the cerebral vasculature. Such filtering devices, however, carry certain limitations. They must be advanced to the target vessel and cross the stenosis prior to deployment, which exposes the cerebral vascular to embolic showers; they are not always easy to advance, deploy, and remove through a tight stenosis and/or a severely angulated vasculature; and finally, they only filter particles larger than the filter pore size, typically 100 to 120 µm. Also, these devices do not filter 100% of the flow due to incomplete wall opposition of the filter, and furthermore there is a risk of debris escape during filter retrieval.

Of particular interest to the present disclosure, an alternative method for reducing the risk of emboli release into the internal carotid artery ICA has been proposed for use during carotid stenting CAS procedures utilizing the concept of reversing the flow in the internal carotid artery ICA to prevent embolic debris entering the cerebral vasculature. Although a number of specific protocols have been described, they generally rely on placing a sheath via the femoral artery (transfemoral access) into the common carotid artery. Flow in the common carotid artery is occluded, typically by inflating a balloon on the distal tip of the sheath. Flow into the external carotid artery ECA may also be occluded, typically using a balloon catheter or balloon guidewire introduced through the sheath. The sheath is then connected to a venous location or to a low pressure external receptacle in order to establish a reverse or retrograde flow from the internal carotid artery through the sheath and away from the cerebral vasculature. After such reverse or retrograde flow is established, the stenting procedure may be performed with a greatly reduced risk of emboli entering the cerebral vasculature.

An alternate system which simply halts forward flow in the ICA consists of a carotid access sheath with two integral balloons: an ECA occlusion balloon at the distal tip, and a CCA occlusion balloon placed some fixed distance proximal to the ECA balloon. Between the two balloons is an opening for delivery of the interventional carotid stenting devices. This system does not reverse flow from the ICA to the venous system, but instead relies on blocking flow and performing aspiration to remove embolic debris prior to establishing forward flow in the ICA.

While such reverse or static flow protocols for performing stenting and other interventional procedures in the carotid vasculature hold great promise, such methods have generally required the manipulation of multiple separate access and occlusion components. Moreover, the protocols have been rather complicated, requiring many separate steps, limiting their performance to only the most skilled vascular surgeons, interventional radiologists and cardiologists. In addition, due to the size limitations of the femoral access, the access devices themselves provide a very high resistance to flow, limiting the amount of reverse flow and/or aspiration possible. Furthermore, the requirement to occlude the external carotid artery adds risk and complexity to the procedure. The balloon catheter for occluding the external carotid artery can become trapped in the arterial wall in cases where the stent is placed across the bifurcation from the common carotid artery to the internal carotid artery, and may cause damage to the deployed stent when it is removed.

None of the cerebral protection devices and methods described offer protection after the procedure. However, generation of embolic particles has been measured up to 48 hours or later, after the stent procedure. During CEA, flushing at the end of the procedure while blocking flow to the internal carotid artery ICA may help reduce post-procedure emboli generation. A similar flushing step during CAS may also reduce emboli risk. Additionally, a stent which is designed to improve entrapment of embolic particles may also reduce post-procedure emboli.

In addition, all currently available carotid stenting and cerebral protection systems are designed for access from the femoral artery. Unfortunately, the pathway from the femoral artery to the common carotid artery is relatively long, has several turns which in some patients can be quite angulated, and often contains plaque and other diseases. The portion of the procedure involving access to the common carotid artery from the femoral artery can be difficult and time consuming as well as risk generating showers of embolic debris up both the target and the opposite common carotid artery and thence to the cerebral vasculature. Some studies suggest that up to half, or more, of embolic complications during CAS procedures occur during access to the CCA. None of the protocols or systems offer protection during this portion of the procedure.

Recently, a reverse flow protocol having an alternative access route to the carotid arteries has been proposed by Criado. This alternative route consists of direct surgical access to the common carotid artery CCA, called transcervical or transcarotid access. Transcarotid access greatly shortens the length and tortuosity of the pathway from the vascular access point to the target treatment site thereby easing the time and difficulty of the procedure. Additionally, this access route reduces the risk of emboli generation from navigation of diseased, angulated, or tortuous aortic arch or common carotid artery anatomy.

The Criado protocol is described in several publications in the medical literature cited below. As shown in FIG. 3, the Criado protocol uses a flow shunt which includes an arterial sheath 210 and a venous sheath 212. Each sheath has a side arm 214, terminating in a stopcock 216. The two sheaths stopcocks are connected by a connector tubing 218, thus completing a reverse flow shunt from the arterial sheath 210 to the venous sheath 212. The arterial sheath is placed in the common carotid artery CCA through an open surgical incision in the neck below the carotid bifurcation. Occlusion of the common carotid artery CCA is accomplished using a temporary vessel ligation, for example using a Rummel tourniquet and umbilical tape or vessel loop. The venous return sheath 212 is placed in the internal jugular vein IJV (FIG. 3), also via an open surgical incision. Retrograde flow from the internal carotid artery ICA and the external carotid artery ECA may then be established by opening the stopcock 216. The Criado protocol is an improvement over the earlier retrograde flow protocols since it eliminates the need for femoral access. Thus, the potential complications associated with the femoral access are completely avoided. Furthermore, the lower flow restrictions presented by the shorter access route offer the opportunity for more vigorous reverse flow rate, increasing the efficiency of embolic debris removal. Because of these reduced flow restrictions, the desired retrograde flow of the internal carotid artery ICA may be established without occluding the external carotid artery ECA, as required by the earlier protocols.

While a significant improvement over the femoral access-based retrograde flow protocols, the Criado protocol and flow shunt could still benefit from improvement. In particular, the existing arterial and venous sheaths used in the procedure still have significant flow restrictions in the side arms 214 and stopcocks 216. When an interventional catheter is inserted into the arterial access sheath, the reverse flow circuit resistance is at a maximum. In some percentage of patients, the external carotid artery ECA perfusion pressure is greater than the internal carotid artery ICA perfusion pressure. In these patients, this differential pressure might drive antegrade flow into the ICA from the ECA. A reverse flow shunt with lower flow resistance could guarantee reversal of flow in both the ECA and ICA despite a pressure gradient from the ECA to the ICA.

In addition, there is no means to monitor or regulate the reverse flow rate. The ability to increase and/or modulate the flow rate would give the user the ability to set the reverse flow rate optimally to the tolerance and physiology of the patient and the stage of the procedure, and thus offer improved protection from embolic debris. Further, the system as described by Criado relies on manually turning one or more stopcocks to open and close the reverse flow shunt, for example during injection of contrast medium to facilitate placement of the CAS systems. Finally, the Criado protocol relies on open surgical occlusion of the common carotid artery, via a vessel loop or Rummel tourniquet. A system with means to occlude the common carotid artery intravascularly, for example with an occlusion element on the arterial access sheath, would allow the entire procedure to be performed using percutaneous techniques. A percutaneous approach would limit the size and associated complications of a surgical incision, as well as enable non-surgical physicians to perform the procedure.

For these reasons, it would be desirable to provide improved methods, apparatus, and systems for performing transcarotid access, retrograde flow and flushing procedures and implantation of a carotid stent in the carotid arterial vasculature to reduce the risk of procedural and post-procedural emboli, to improve the level of hemostasis throughout the procedure, and to improve the ease and speed of carotid artery stenting. The methods, apparatus, and system should simplify the procedure to be performed by the physician as well as reduce the risk of improperly performing the procedures and/or achieving insufficient retrograde flow and flushing to protect against emboli release. The systems should provide individual devices and components which are readily used with each other and which protect against emboli-related complications. The methods and systems should also provide for convenient and preferably automatic closure of any and all arterial penetrations at the end of the procedure to prevent unintended blood loss. Additionally, the systems, apparatus, and methods should be suitable for performance by either open surgical or percutaneous access routes into the vasculature. Additionally, the methods, apparatus, and systems should enable implantation of an intravascular prosthetic implant which lowers post procedural complications. At least some of these objectives will be met by the inventions described herein below.

BRIEF DESCRIPTION OF THE DRAWINGS

FIG. 6A illustrates an arterial access device useful in the methods and systems of the present disclosure.

FIG. 6B illustrates an additional arterial access device construction with a reduced diameter distal end.

FIGS. 7A and 7B illustrate a tube useful with the sheath of FIG. 6A.

FIG. 8A illustrates an additional arterial access device construction with an expandable occlusion element.

FIG. 8B illustrates an additional arterial access device construction with an expandable occlusion element and a reduced diameter distal end.

FIGS. 10A through 10D illustrate embodiments of a venous return device useful in the methods and systems of the present disclosure.

FIGS. 13A-13D illustrate an embodiment of a fenestrated sheath.

DETAILED DESCRIPTION

Figure 1A:
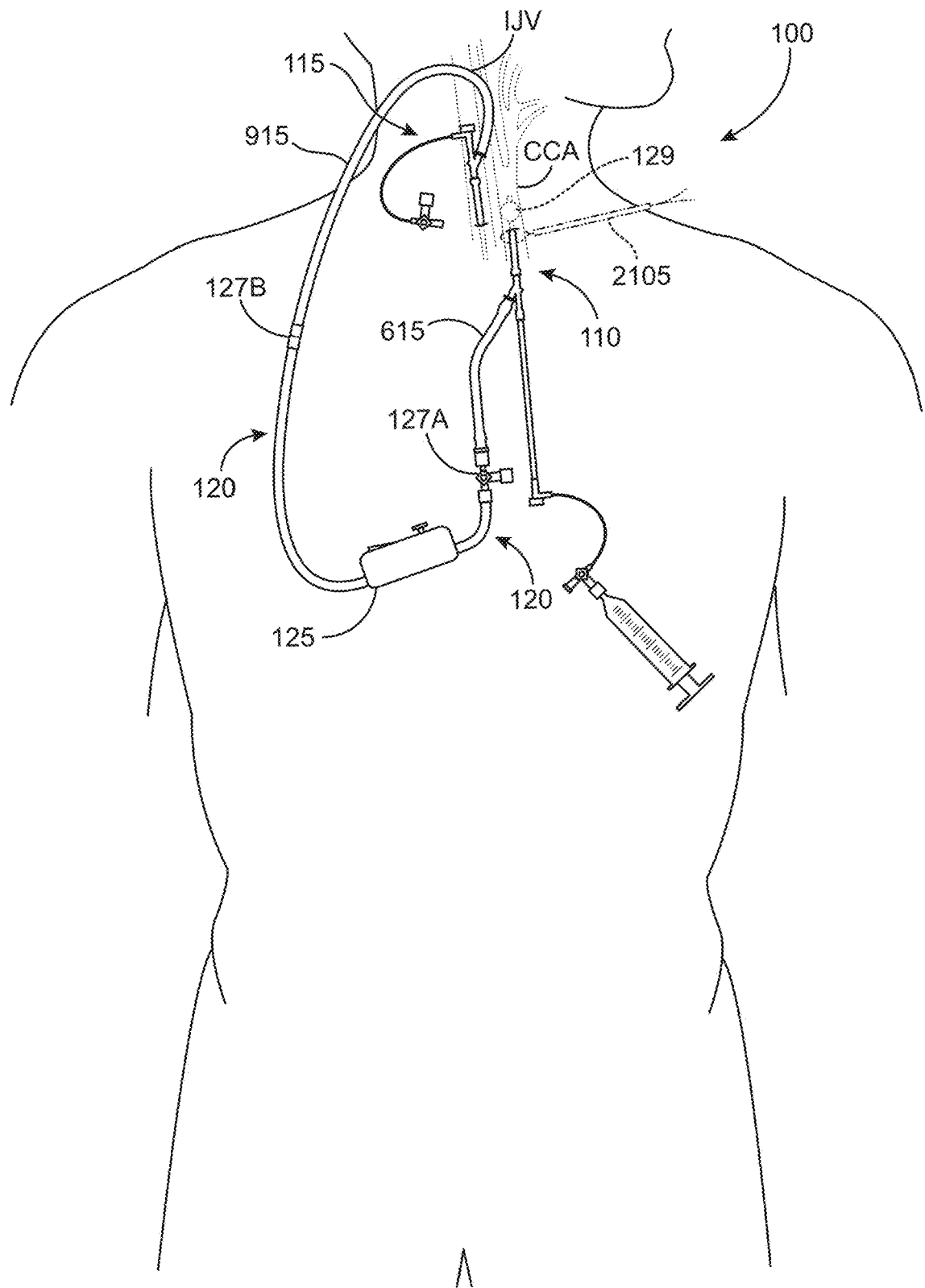
FIG. 1A is a schematic illustration of a retrograde blood flow system including a flow control assembly wherein an arterial access device accesses the common carotid artery via a transcarotid approach and a venous return device communicates with the internal jugular vein.

The disclosed methods, apparatus, and systems establish and facilitate retrograde or reverse flow blood circulation in the region of the carotid artery bifurcation in order to limit or prevent the release of emboli into the cerebral vasculature, particularly into the internal carotid artery. The methods are particularly useful for interventional procedures, such as stenting and angioplasty, atherectomy, performed through a transcarotid approach or transfemoral into the common carotid artery, either using an open surgical technique or using a percutaneous technique, such as a modified Seldinger technique or a micropuncture technique.

Access into the common carotid artery (FIG. 5) is established by placing a sheath or other tubular access cannula into a lumen of the artery, typically having a distal end of the sheath positioned proximal to the junction or bifurcation B from the common carotid artery to the internal and external carotid arteries. The sheath may have an occlusion member at the distal end, for example a compliant occlusion balloon. A catheter or guidewire with an occlusion member, such as a balloon, may be placed through the access sheath and positioned in the proximal external carotid artery ECA to inhibit the entry of emboli, but occlusion of the external carotid artery is usually not necessary. A second return sheath is placed in the venous system, for example the internal jugular vein IJV or femoral vein FV. The arterial access and venous return sheaths are connected to create an external arterial-venous shunt.

Retrograde flow is established and modulated to meet the patient's requirements. Flow through the common carotid artery is occluded, either with an external vessel loop or tape, a vascular clamp, an internal occlusion member such as a balloon, or other type of occlusion means. When flow through the common carotid artery is blocked, the natural pressure gradient between the internal carotid artery and the venous system will cause blood to flow in a retrograde or reverse direction from the cerebral vasculature through the internal carotid artery and through the shunt into the venous system.

Alternately, the venous sheath could be eliminated and the arterial sheath could be connected to an external collection reservoir or receptacle. The reverse flow could be collected in this receptacle. If desired, the collected blood could be filtered and subsequently returned to the patient during or at the end of the procedure. The pressure of the receptacle could be open to atmospheric pressure, causing the pressure gradient to create blood to flow in a reverse direction from the cerebral vasculature to the receptacle or the pressure of the receptacle could be a negative pressure.

Optionally, to achieve or enhance reverse flow from the internal carotid artery, flow from the external carotid artery may be blocked, typically by deploying a balloon or other occlusion element in the external carotid just above (i.e., distal) the bifurcation within the internal carotid artery.

Although the procedures and protocols described hereinafter will be particularly directed at carotid stenting, it will be appreciated that the methods for accessing the carotid artery described herein would also be useful for angioplasty, atherectomy, and any other interventional procedures which might be carried out in the carotid arterial system, particularly at a location near the bifurcation between the internal and external carotid arteries. In addition, it will be appreciated that some of these access, vascular closure, and embolic protection methods will be applicable in other vascular interventional procedures, for example the treatment of acute stroke.

The present disclosure includes a number of specific aspects for improving the performance of carotid artery access protocols. At least most of these individual aspects and improvements can be performed individually or in combination with one or more other of the improvements in order to facilitate and enhance the performance of the particular interventions in the carotid arterial system.

In one aspect, there is disclosed a system for use in accessing and treating a carotid artery. The system comprises an arterial access device adapted to be introduced into a common carotid artery and receive blood flow from the common carotid artery; a shunt fluidly connected to the arterial access device, wherein the shunt provides a pathway for blood to flow from the arterial access device to a return site; and a flow control assembly coupled to the shunt and adapted to regulate blood flow through the shunt between at least a first blood flow state and at least a second blood flow state, wherein the flow control assembly includes one or more components that interact with the blood flow through the shunt.

In another aspect, there is disclosed a system for use in accessing and treating a carotid artery. The system comprises an arterial access device adapted to be introduced into a common carotid artery and receive blood flow from the common carotid artery; a shunt fluidly connected to the arterial access device, wherein the shunt provides a pathway for blood to flow from the arterial access device to a return site; a flow mechanism coupled to the shunt and adapted to vary the blood flow through the shunt between a first blood flow rate and a second blood flow rate; and a controller that automatically interacts with the flow mechanism to regulate blood flow through the shunt between the first blood flow rate and the second blood flow rate without requiring input from a user.

In another aspect, there is disclosed a device for use in accessing and treating a carotid artery. The device comprises a distal sheath having a distal end adapted to be introduced into the common carotid artery, a proximal end, and a lumen extending between the distal and proximal ends; a proximal extension having a distal end, a proximal end, and a lumen therebetween, wherein the distal end of the proximal extension is connected to the proximal end of the sheath at a junction so that the lumens of each are contiguous; a flow line having a lumen, said flow line connected near the junction so that blood flowing into the distal end of the sheath can flow into the lumen of the flow line; and a hemostasis valve at the proximal end of the proximal extension, said hemostasis valve being adapted to inhibit blood flow from the proximal extension while allowing catheter introduction through the proximal extension and into the distal sheath.

In another aspect, there is disclosed a method for accessing and treating a carotid artery. The method comprises forming a penetration in a wall of a common carotid artery; positioning an access sheath through the penetration; blocking blood flow from the common carotid artery past the sheath; allowing retrograde blood flow from the carotid artery into the sheath and from the sheath via a flow path to a return site; and modifying blood flow through the flow path based on feedback data.

In another aspect, there is disclosed a method for accessing and treating a carotid artery. The method comprises forming a penetration in a wall of a common carotid artery; positioning an access sheath through the penetration; blocking blood flow from the common carotid artery past the sheath; allowing retrograde blood flow from the carotid artery into the sheath and from the sheath via a flow path to a return site; and monitoring flow through the flow path.

In another aspect, there is disclosed a method for accessing and treating a carotid artery. The method comprises: forming a penetration in a wall of a common carotid artery; positioning an arterial access sheath through the penetration; blocking blood flow from the common carotid artery past the sheath; allowing retrograde blood flow from the internal carotid artery into the sheath while the common carotid artery remains blocked; and adjusting the state of retrograde blood flow through the sheath.

In another aspect, there is disclosed a method for accessing and treating a carotid artery. The method comprises forming a penetration in a wall of a common carotid artery; positioning an arterial access sheath through the penetration; blocking blood flow from the common carotid artery past the sheath; allowing retrograde blood flow from the internal carotid artery into the sheath while the common carotid artery remains blocked; and adjusting a rate of retrograde blood flow from the sheath to as high a level as the patient will tolerate, wherein said adjusted rate is a baseline.

This application is related to U.S. Pat. No. 8,157,760 entitled "Methods and Systems for Establishing Retrograde Carotid Arterial Flow" and U.S. patent application Ser. No. 14/227,585 entitled "Methods and Systems For Establishing Retrograde Carotid Arterial Blood Flow", both of which are incorporated herein by reference.

FIG. 1A shows a first embodiment of a retrograde flow system 100 that is adapted to establish and facilitate retrograde or reverse flow blood circulation in the region of the carotid artery bifurcation in order to limit or prevent the release of emboli into the cerebral vasculature, particularly into the internal carotid artery. The system 100 interacts with the carotid artery to provide retrograde flow from the carotid artery to a venous return site, such as the internal jugular vein (or to another return site such as another large vein or an external receptacle in alternate embodiments.) The retrograde flow system 100 includes an arterial access device 110, a venous return device 115, and a shunt 120 that provides a passageway for retrograde flow from the arterial access device 110 to the venous return device 115. A flow control assembly 125 interacts with the shunt 120. The flow control assembly 125 is adapted to regulate and/or monitor the retrograde flow from the common carotid artery to the internal jugular vein, as described in more detail below. The flow control assembly 125 interacts with the flow pathway through the shunt 120, either external to the flow path, inside the flow path, or both. The arterial access device 110 at least partially inserts into the common carotid artery CCA and the venous return device 115 at least partially inserts into a venous return site such as the internal jugular vein IJV, as described in more detail below. The arterial access device 110 and the venous return device 115 couple to the shunt 120 at connection locations 127a and 127b. When flow through the common carotid artery is blocked, the natural pressure gradient between the internal carotid artery and the venous system causes blood to flow in a retrograde or reverse direction RG (FIG. 2A) from the cerebral vasculature through the internal carotid artery and through the shunt 120 into the venous system. The flow control assembly 125 modulates, augments, assists, monitors, and/or otherwise regulates the retrograde blood flow.

In the embodiment of FIG. 1A, the arterial access device 110 accesses the common carotid artery CCA via a transcarotid approach. Transcarotid access provides a short length and non-tortuous pathway from the vascular access point to the target treatment site thereby easing the time and difficulty of the procedure, compared for example to a transfemoral approach. In an embodiment, the arterial distance from the arteriotomy to the target treatment site (as measured traveling through the artery) is 15 cm or less. In an embodiment, the distance is between 5 and 10 cm. Additionally, this access route reduces the risk of emboli generation from navigation of diseased, angulated, or tortuous aortic arch or common carotid artery anatomy. At least a portion of the venous return device 115 is placed in the internal jugular vein IJV. In an embodiment, transcarotid access to the common carotid artery is achieved percutaneously via an incision or puncture in the skin through which the arterial access device 110 is inserted. If an incision is used, then the incision can be about 0.5 cm in length. An occlusion element 129, such as an expandable balloon, can be used to occlude the common carotid artery CCA at a location proximal of the distal end of the arterial access device 110. The occlusion element 129 can be located on the arterial access device 110 or it can be located on a separate device. In an alternate embodiment, the arterial access device 110 accesses the common carotid artery CCA via a direct surgical transcarotid approach. In the surgical approach, the common carotid artery can be occluded using a tourniquet 2105. The tourniquet 2105 is shown in phantom to indicate that it is a device that is used in the optional surgical approach.

Figure 1B:
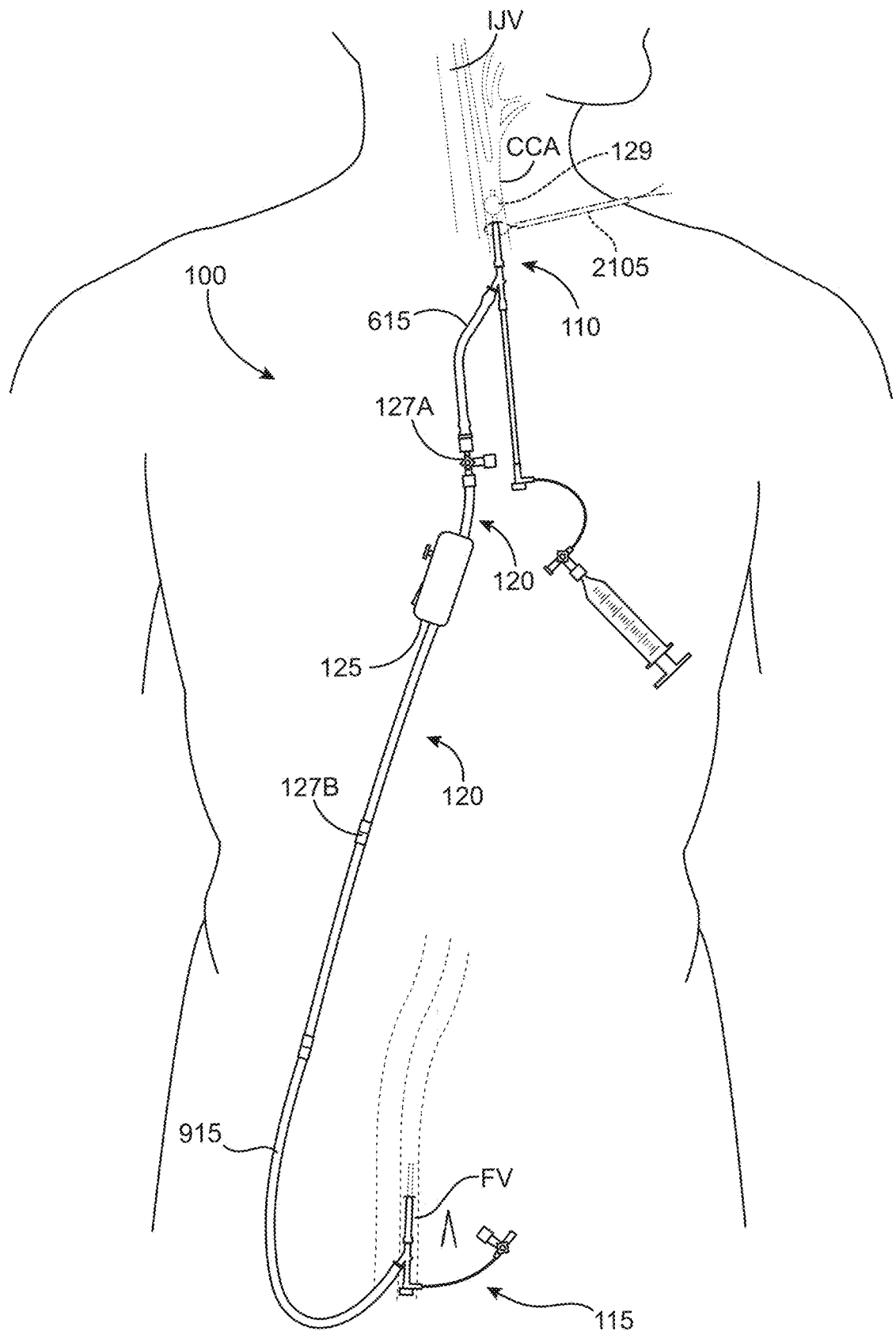
FIG. 1B is a schematic illustration of a retrograde blood flow system wherein an arterial access device accesses the common carotid artery via a transcarotid approach and a venous return device communicates with the femoral vein.

In another embodiment, shown in FIG. 1B, the arterial access device 110 accesses the common carotid artery CCA via a transcarotid approach while the venous return device 115 access a venous return site other than the jugular vein, such as a venous return site comprised of the femoral vein FV. The venous return device 115 can be inserted into a central vein such as the femoral vein FV via a percutaneous puncture in the groin.

Figure 1C:
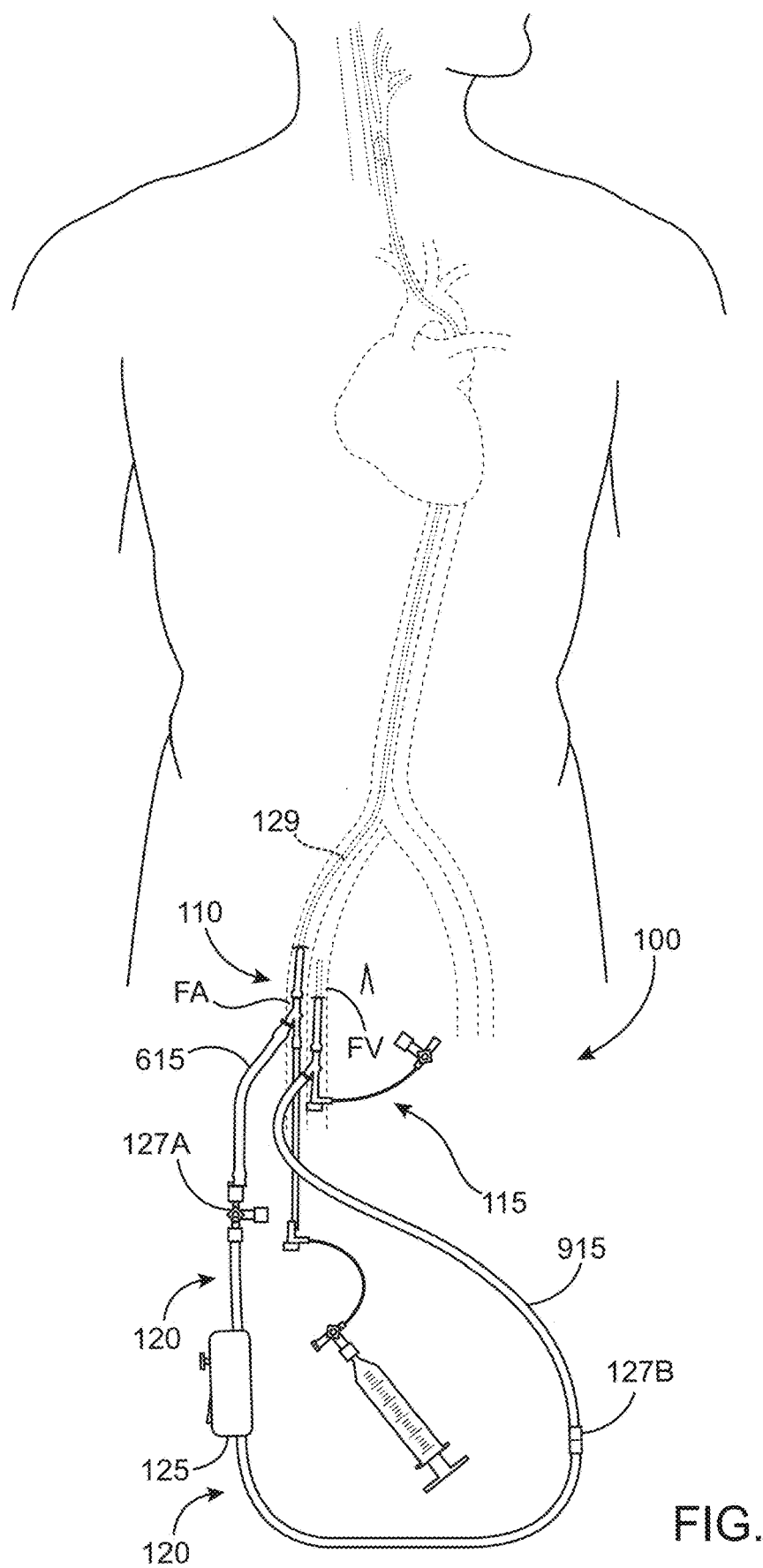
FIG. 1C is a schematic illustration of a retrograde blood flow system wherein an arterial access device accesses the common carotid artery via a transfemoral approach and a venous return device communicates with the femoral vein.

In another embodiment, shown in FIG. 1C, the arterial access device 110 accesses the common carotid artery via a femoral approach. According to the femoral approach, the arterial access device 110 approaches the CCA via a percutaneous puncture into the femoral artery FA, such as in the groin, and up the aortic arch AA into the target common carotid artery CCA. The venous return device 115 can communicate with the jugular vein JV or the femoral vein FV.

Figure 1D:
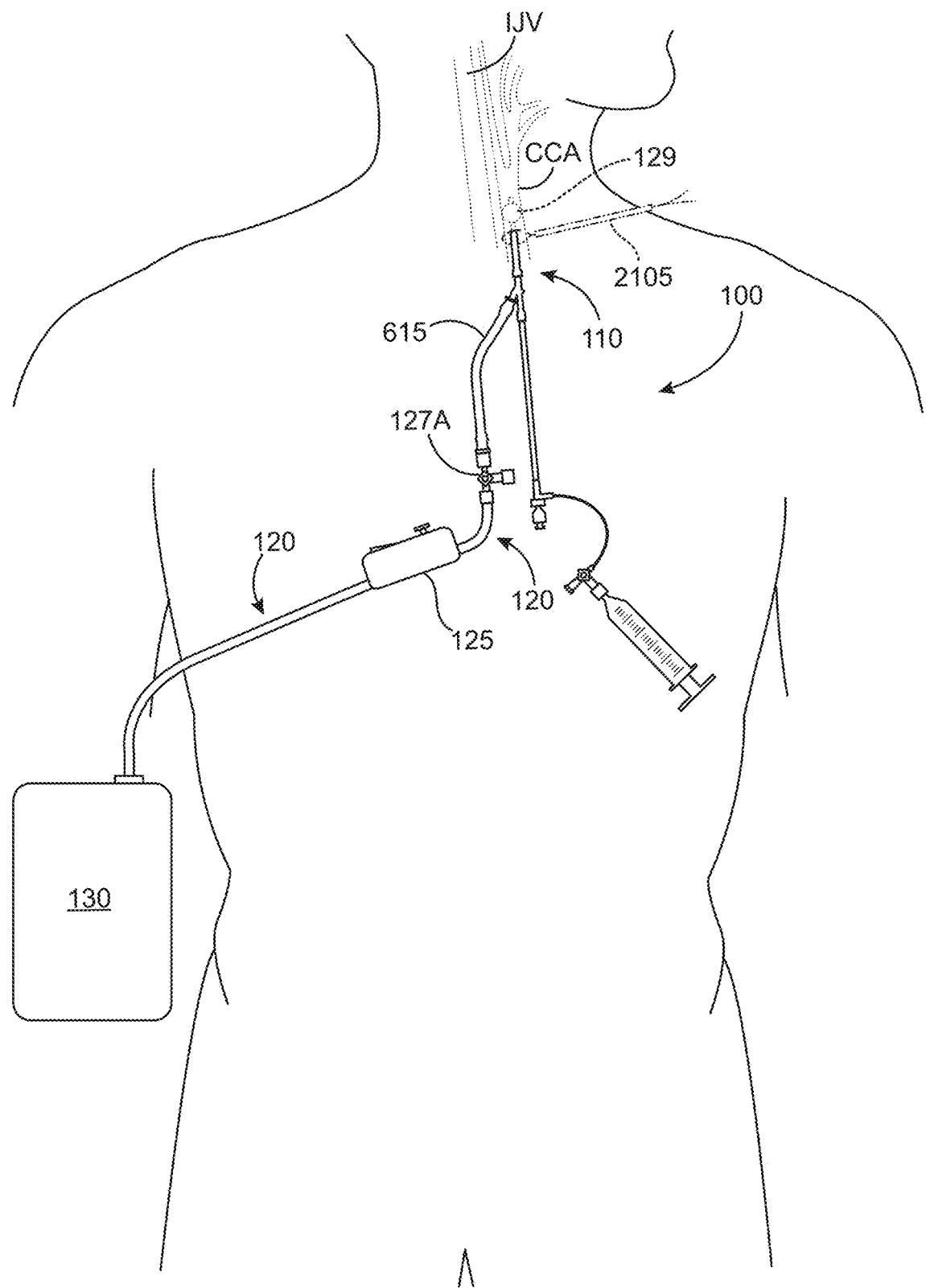
FIG. 1D is a schematic illustration of a retrograde blood flow system wherein retrograde flow is collected in an external receptacle.

FIG. 1D shows yet another embodiment, wherein the system provides retrograde flow from the carotid artery to an external receptacle 130 rather than to a venous return site. The arterial access device 110 connects to the receptacle 130 via the shunt 120, which communicates with the flow control assembly 125. The retrograde flow of blood is collected in the receptacle 130. If desired, the blood could be filtered and subsequently returned to the patient. The pressure of the receptacle 130 could be set at zero pressure (atmospheric pressure) or even lower, causing the blood to flow in a reverse direction from the cerebral vasculature to the receptacle 130. Optionally, to achieve or enhance reverse flow from the internal carotid artery, flow from the external carotid artery can be blocked, typically by deploying a balloon or other occlusion element in the external carotid artery just above the bifurcation with the internal carotid artery. FIG. 1D shows the arterial access device 110 arranged in a transcarotid approach with the CCA although it should be appreciated that the use of the external receptacle 130 can also be used with the arterial access device 110 in a transfemoral approach.

Figure 2A:
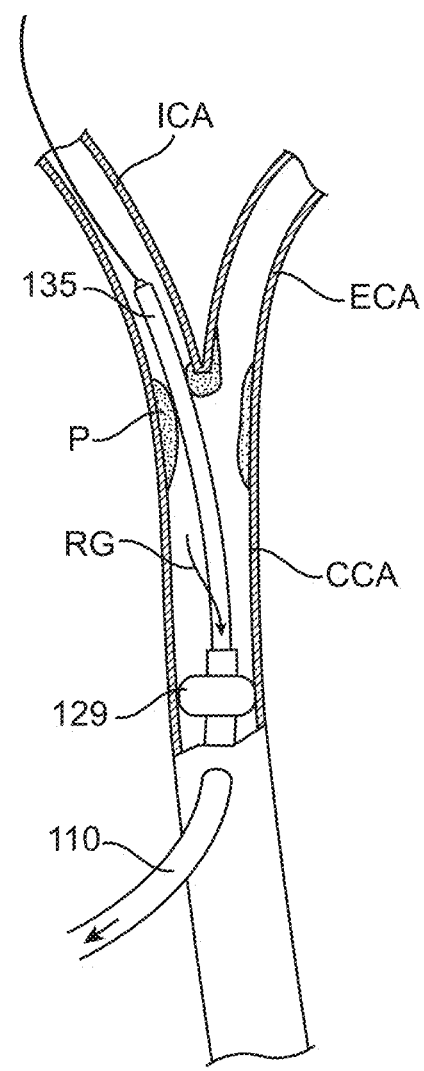
FIG. 2A is an enlarged view of the carotid artery wherein the carotid artery is occluded with an occlusion element on the sheath and connected to a reverse flow shunt, and an interventional device, such as a stent delivery system or other working catheter, is introduced into the carotid artery via an arterial access device.

With reference to the enlarged view of the carotid artery in FIG. 2A, an interventional device, such as a stent delivery system 135 or other working catheter, can be introduced into the carotid artery via the arterial access device 110, as described in detail below. The stent delivery system 135 can be used to treat the plaque P such as to deploy a stent into the carotid artery. The arrow RG in FIG. 2A represents the direction of retrograde flow.

Figure 2B:
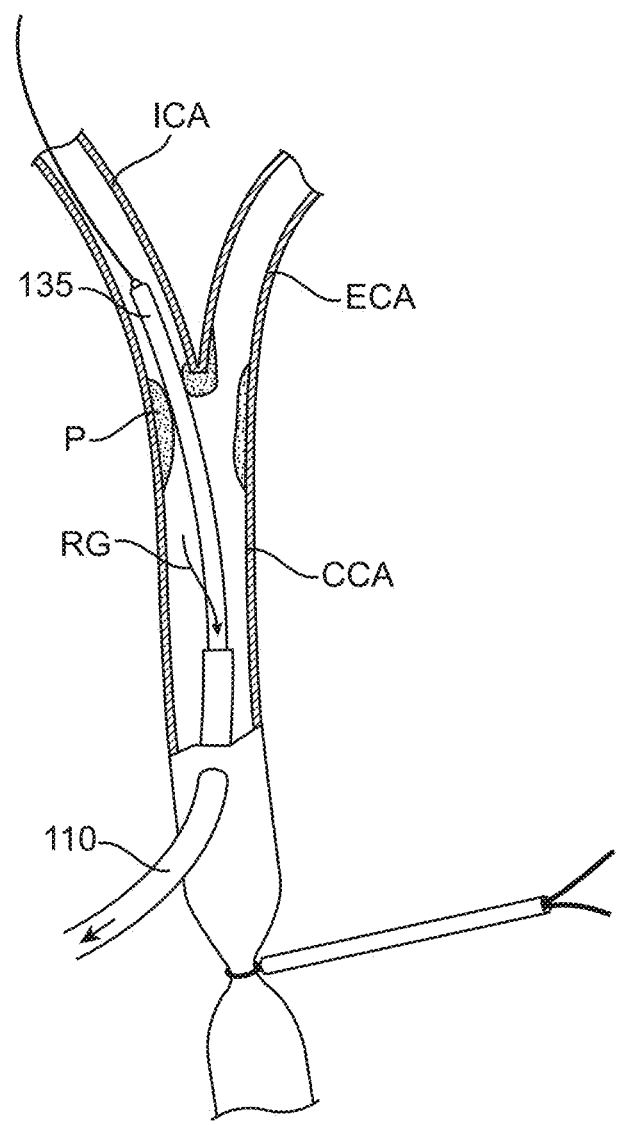
FIG. 2B is an alternate system wherein the carotid artery is occluded with a separate external occlusion device and connected to a reverse flow shunt, and an interventional device, such as a stent delivery system or other working catheter, is introduced into the carotid artery via an arterial access device.

FIG. 2B shows another embodiment, wherein the arterial access device 110 is used for the purpose of creating an arterial-to-venous shunt as well as introduction of at least one interventional device into the carotid artery. A separate arterial occlusion device 112 with an occlusion element 129 can be used to occlude the common carotid artery CCA at a location proximal to the distal end of the arterial access device 110.

Figure 2C:
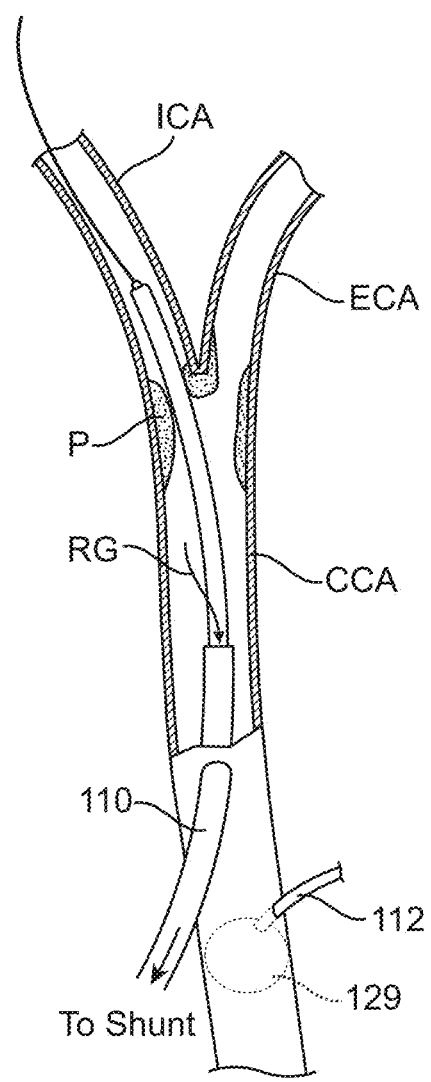
FIG. 2C is an alternate system wherein the carotid artery is connected to a reverse flow shunt and an interventional device, such as a stent delivery system or other working catheter, is introduced into the carotid artery via an arterial access device, and the carotid artery is occluded with a separate occlusion device.
Figure 2D:
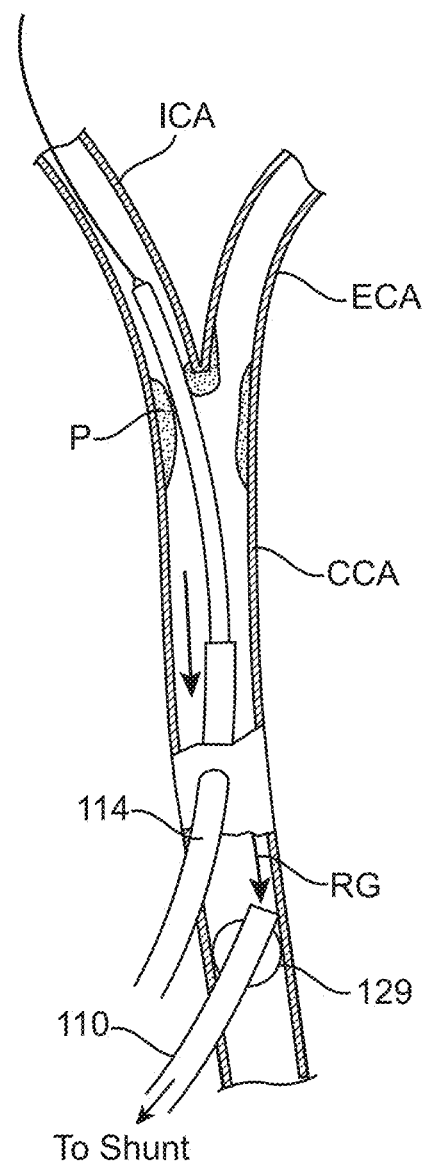
FIG. 2D is an alternate system wherein the carotid artery is occluded and the artery is connected to a reverse flow shunt via an arterial access device and the interventional device, such as a stent delivery system, is introduced into the carotid artery via a separate arterial introducer device.
Figure 3:
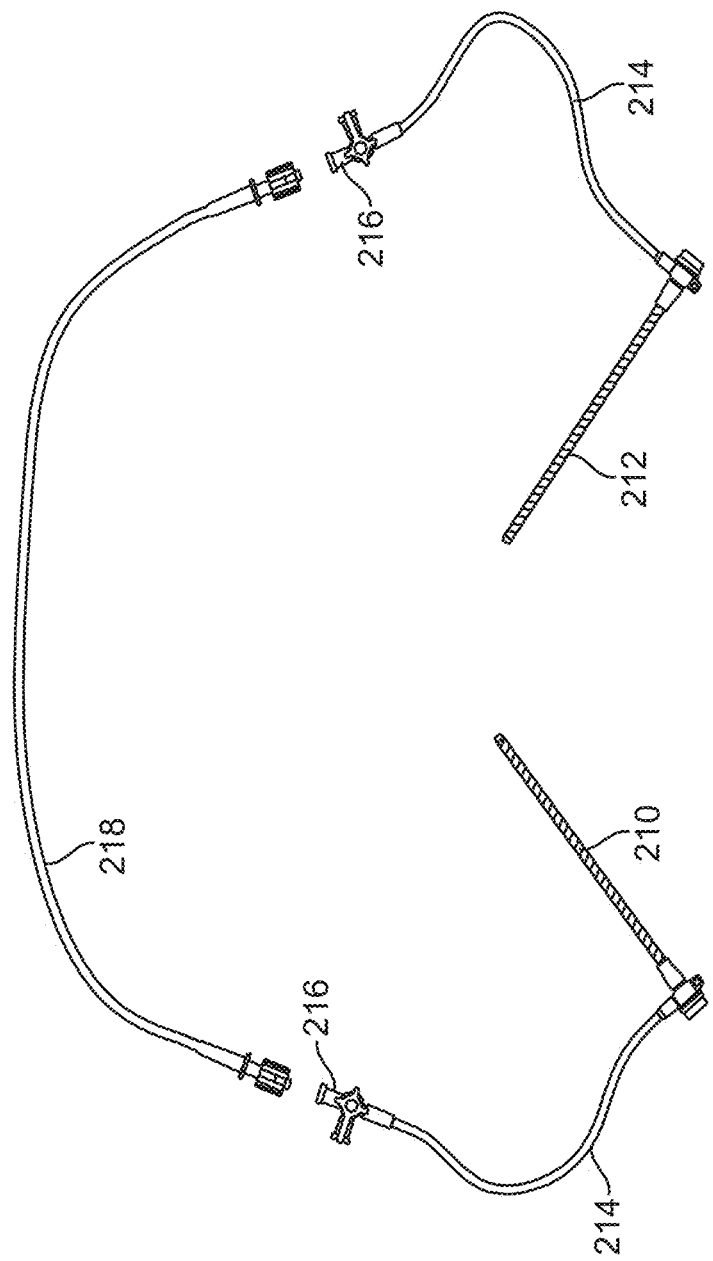
FIG. 3 illustrates a prior art Criado flow shunt system.

FIG. 2C shows yet another embodiment wherein the arterial access device 110 is used for the purpose of creating an arterial-to-venous shunt as well as arterial occlusion using an occlusion element 129. A separate arterial introducer device can be used for the introduction of at least one interventional device into the carotid artery at a location distal to the arterial access device 110.

Description of Anatomy

Collateral Brain Circulation

The Circle of Willis CW is the main arterial anastomatic trunk of the brain where all major arteries which supply the brain, namely the two internal carotid arteries (ICAs) and the vertebral basilar system, connect. The blood is carried from the Circle of Willis by the anterior, middle and posterior cerebral arteries to the brain. This communication between arteries makes collateral circulation through the brain possible. Blood flow through alternate routes is made possible thereby providing a safety mechanism in case of blockage to one or more vessels providing blood to the brain. The brain can continue receiving adequate blood supply in most instances even when there is a blockage somewhere in the arterial system (e.g., when the ICA is ligated as described herein). Flow through the Circle of Willis ensures adequate cerebral blood flow by numerous pathways that redistribute blood to the deprived side.

The collateral potential of the Circle of Willis is believed to be dependent on the presence and size of its component vessels. It should be appreciated that considerable anatomic variation between individuals can exist in these vessels and that many of the involved vessels may be diseased. For example, some people lack one of the communicating arteries. If a blockage develops in such people, collateral circulation is compromised resulting in an ischemic event and potentially brain damage. In addition, an autoregulatory response to decreased perfusion pressure can include enlargement of the collateral arteries, such as the communicating arteries, in the Circle of Willis. An adjustment time is occasionally required for this compensation mechanism before collateral circulation can reach a level that supports normal function. This autoregulatory response can occur over the space of 15 to 30 seconds and can only compensate within a certain range of pressure and flow drop. Thus, it is possible for a transient ischemic attack to occur during the adjustment period. Very high retrograde flow rate for an extended period of time can lead to conditions where the patient's brain is not getting enough blood flow, leading to patient intolerance as exhibited by neurologic symptoms or in some cases a transient ischemic attack.

Figure 4:
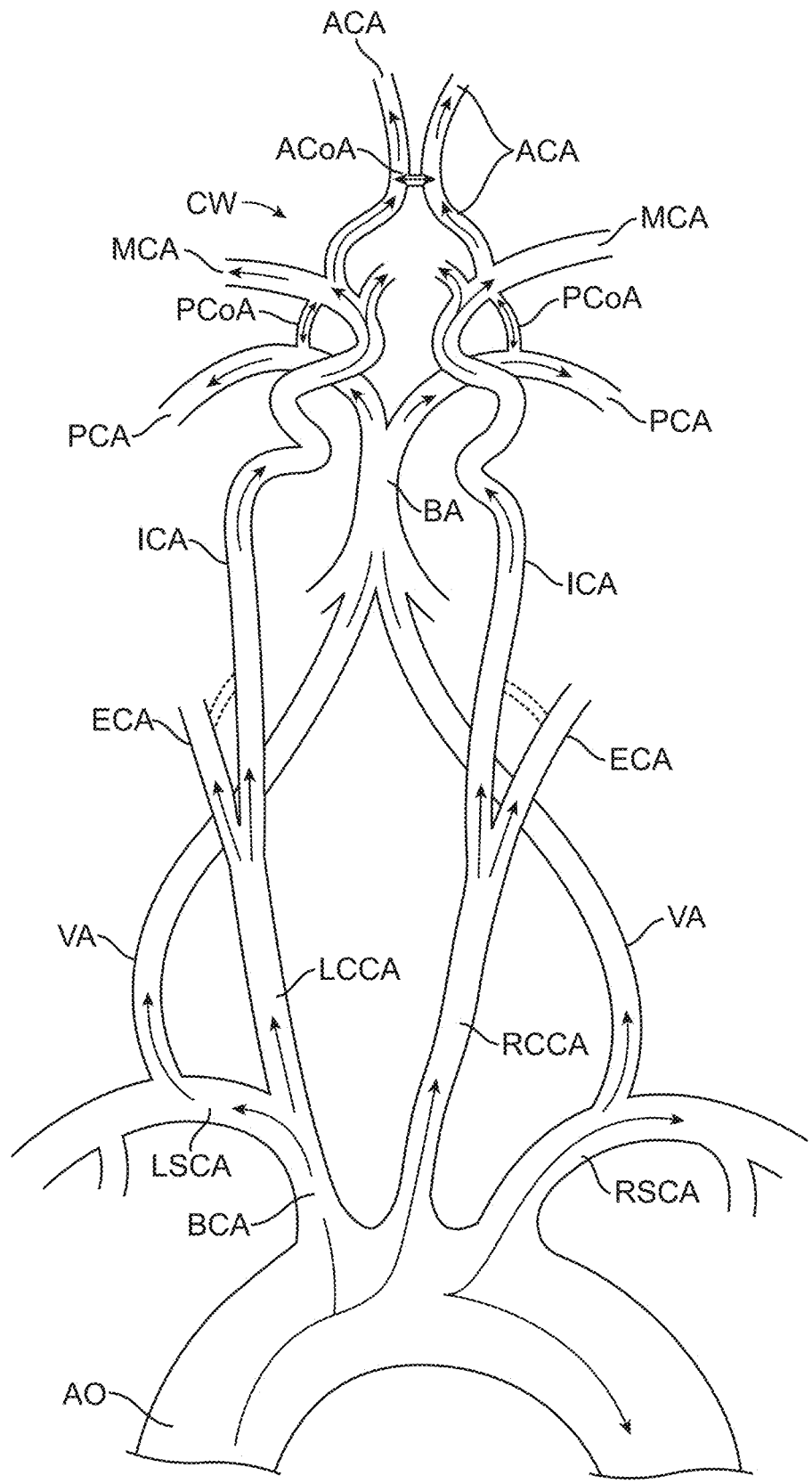
FIG. 4 illustrates a normal cerebral circulation diagram including the Circle of Willis.

FIG. 4 depicts a normal cerebral circulation and formation of Circle of Willis CW. The aorta AO gives rise to the brachiocephalic artery BCA, which branches into the left common carotid artery LCCA and left subclavian artery LSCA. The aorta AO further gives rise to the right common carotid artery RCCA and right subclavian artery RSCA. The left and right common carotid arteries CCA gives rise to internal carotid arteries ICA which branch into the middle cerebral arteries MCA, posterior communicating artery PcoA, and anterior cerebral artery ACA. The anterior cerebral arteries ACA deliver blood to some parts of the frontal lobe and the corpus striatum. The middle cerebral arteries MCA are large arteries that have tree-like branches that bring blood to the entire lateral aspect of each hemisphere of the brain. The left and right posterior cerebral arteries PCA arise from the basilar artery BA and deliver blood to the posterior portion of the brain (the occipital lobe).

Anteriorly, the Circle of Willis is formed by the anterior cerebral arteries ACA and the anterior communicating artery ACoA which connects the two ACAs. The two posterior communicating arteries PCoA connect the Circle of Willis to the two posterior cerebral arteries PCA, which branch from the basilar artery BA and complete the Circle posteriorly.

The common carotid artery CCA also gives rise to external carotid artery ECA, which branches extensively to supply most of the structures of the head except the brain and the contents of the orbit. The ECA also helps supply structures in the neck and face.

Carotid Artery Bifurcation

Figure 5:
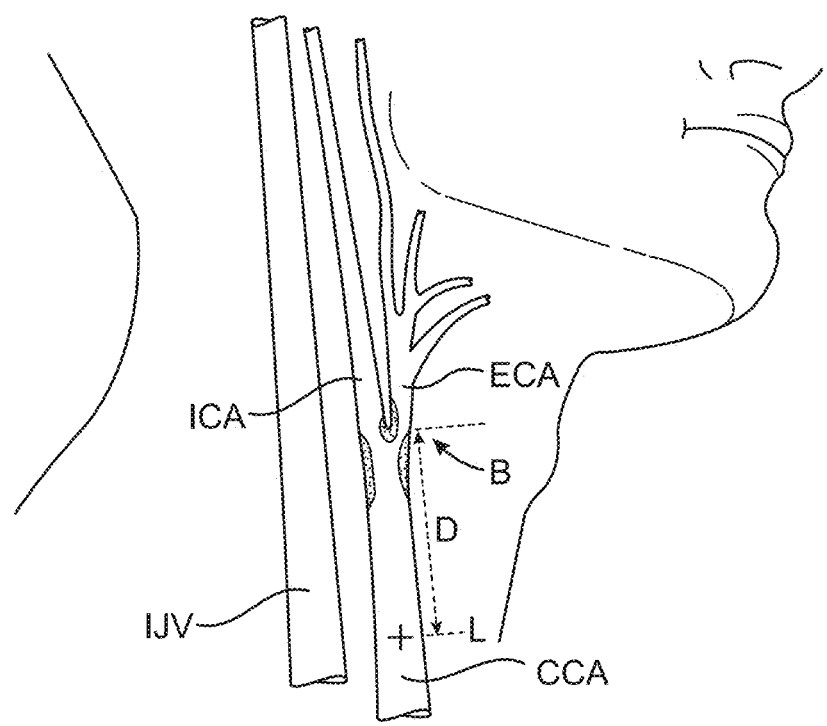
FIG. 5 illustrates the vasculature in a patient's neck, including the common carotid artery CCA, the internal carotid artery ICA, the external carotid artery ECA, and the internal jugular vein IJV.

FIG. 5 shows an enlarged view of the relevant vasculature in the patient's neck. The common carotid artery CCA branches at bifurcation B into the internal carotid artery ICA and the external carotid artery ECA. The bifurcation is located at approximately the level of the fourth cervical vertebra. FIG. 5 shows plaque P formed at the bifurcation B.

As discussed above, the arterial access device 110 can access the common carotid artery CCA via a transcarotid approach. Pursuant to the transcarotid approach, the arterial access device 110 is inserted into the common carotid artery CCA at an arterial access location L, which can be, for example, a surgical incision or puncture in the wall of the common carotid artery CCA. There is typically a distance D of around 5 to 7 cm between the arterial access location L and the bifurcation B. When the arterial access device 110 is inserted into the common carotid artery CCA, it is undesirable for the distal tip of the arterial access device 110 to contact the bifurcation B as this could disrupt the plaque P and cause generation of embolic particles. In order to minimize the likelihood of the arterial access device 110 contacting the bifurcation B, in an embodiment only about 2-4 cm of the distal region of the arterial access device is inserted into the common carotid artery CCA during a procedure.

The common carotid arteries are encased on each side in a layer of fascia called the carotid sheath. This sheath also envelops the internal jugular vein and the vagus nerve. Anterior to the sheath is the sternocleidomastoid muscle. Transcarotid access to the common carotid artery and internal jugular vein, either percutaneous or surgical, can be made immediately superior to the clavicle, between the two heads of the sternocleidomastoid muscle and through the carotid sheath, with care taken to avoid the vagus nerve.

At the upper end of this sheath, the common carotid artery bifurcates into the internal and external carotid arteries. The internal carotid artery continues upward without branching until it enters the skull to supply blood to the retina and brain. The external carotid artery branches to supply blood to the scalp, facial, ocular, and other superficial structures. Intertwined both anterior and posterior to the arteries are several facial and cranial nerves. Additional neck muscles may also overlay the bifurcation. These nerve and muscle structures can be dissected and pushed aside to access the carotid bifurcation during a carotid endarterectomy procedure. In some cases the carotid bifurcation is closer to the level of the mandible, where access is more challenging and with less room available to separate it from the various nerves which should be spared. In these instances, the risk of inadvertent nerve injury can increase and an open endarterectomy procedure may not be a good option.

Detailed Description of Retrograde Blood Flow System

As discussed, the retrograde flow system 100 includes the arterial access device 110, venous return device 115, and shunt 120 which provides a passageway for retrograde flow from the arterial access device 110 to the venous return device 115. The system also includes the flow control assembly 125, which interacts with the shunt 120 to regulate and/or monitor retrograde blood flow through the shunt 120. Exemplary embodiments of the components of the retrograde flow system 100 are now described.

Arterial Access Device

FIG. 6A shows an exemplary embodiment of the arterial access device 110, which comprises a distal sheath 605, a proximal extension 610, a flow line 615, an adaptor or Y-connector 620, and a hemostasis valve 625. The arterial access device may also comprise a dilator 645 with a tapered tip 650 and an introducer guide wire 611. The arterial access device together with the dilator and introducer guidewire are used together to gain access to a vessel. Features of the arterial access device may be optimized for transcarotid access. For example, the design of the access device components may be optimized to limit the potential injury on the vessel due to a sharp angle of insertion, allow atraumatic and secure sheath insertion, and limiting the length of sheath, sheath dilator, and introducer guide wire inserted into the vessel.

The distal sheath 605 is adapted to be introduced through an incision or puncture in a wall of a common carotid artery, either an open surgical incision or a percutaneous puncture established, for example, using the Seldinger technique. The length of the sheath can be in the range from 5 to 15 cm, usually being from 10 cm to 12 cm. The inner diameter is typically in the range from 7 Fr (1 Fr=0.33 mm), to 10 Fr, usually being 8 Fr. Particularly when the sheath is being introduced through the transcarotid approach, above the clavicle but below the carotid bifurcation, it is desirable that the sheath 605 be highly flexible while retaining hoop strength to resist kinking and buckling. Thus, the distal sheath 605 can be circumferentially reinforced, such as by braid, helical ribbon, helical wire, cut tubing, or the like and have an inner liner so that the reinforcement structure is sandwiched between an outer jacket layer and the inner liner. The inner liner may be a low friction material such as PTFE. The outer jacket may be one or more of a group of materials including Pebax, thermoplastic polyurethane, or nylon. In an embodiment, the reinforcement structure or material and/or outer jacket material or thickness may change over the length of the sheath 605 to vary the flexibility along the length. In an alternate embodiment, the distal sheath is adapted to be introduced through a percutaneous puncture into the femoral artery, such as in the groin, and up the aortic arch AA into the target common carotid artery CCA.

The distal sheath 605 can have a stepped or other configuration having a reduced diameter distal region 630, as shown in FIG. 6B, which shows an enlarged view of the distal region 630 of the sheath 605. The distal region 630 of the sheath can be sized for insertion into the carotid artery, typically having an inner diameter in the range from 2.16 mm (0.085 inch) to 2.92 mm (0.115 inch) with the remaining proximal region of the sheath having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm. The relatively short length of the reduced-diameter distal section 630 permits this section to be positioned in the common carotid artery CCA via the transcarotid approach with reduced risk that the distal end of the sheath 605 will contact the bifurcation B. Moreover, the reduced diameter section 630 also permits a reduction in size of the arteriotomy for introducing the sheath 605 into the artery while having a minimal impact in the level of flow resistance. Further, the reduced distal diameter section may be more flexible and thus more conformal to the lumen of the vessel.

With reference again to FIG. 6A, the proximal extension 610, which is an elongated body, has an inner lumen which is contiguous with an inner lumen of the sheath 605. The lumens can be joined by the Y-connector 620 which also connects a lumen of the flow line 615 to the sheath. In the assembled system, the flow line 615 connects to and forms a first leg of the retrograde shunt 120 (FIG. 1). The proximal extension 610 can have a length sufficient to space the hemostasis valve 625 well away from the Y-connector 620, which is adjacent to the percutaneous or surgical insertion site. By spacing the hemostasis valve 625 away from a percutaneous insertion site, the physician can introduce a stent delivery system or other working catheter into the proximal extension 610 and sheath 605 while staying out of the fluoroscopic field when fluoroscopy is being performed. In an embodiment, the proximal extension is about 16.9 cm from a distal most junction (such as at the hemostasis valve) with the sheath 605 to the proximal end of the proximal extension. In an embodiment, the proximal extension has an inner diameter of 0.125 inch and an outer diameter of 0.175 inch. In an embodiment, the proximal extension has a wall thickness of 0.025 inch. The inner diameter may range, for example, from 0.60 inch to 0.150 inch with a wall thickness of 0.010 inch to 0.050 inch. In another embodiment, the inner diameter may range, for example, from 0.150 inch to 0.250 inch with a wall thickness of 0.025 inch to 0.100 inch. The dimensions of the proximal extension may vary. In an embodiment, the proximal extension has a length within the range of about 12-20 cm. In another embodiment, the proximal extension has a length within the range of about 20-30 cm.

In an embodiment, the distance along the sheath from the hemostasis valve 625 to the distal tip of the sheath 605 is in the range of about 25 and 40 cm. In an embodiment, the distance is in the range of about 30 and 35 cm. With a system configuration that allows 2.5 cm of sheath introduction into the artery, and an arterial distance of between 5 and 10 cm from the arteriotomy site to the target site, this system enables a distance in the range of about 32.5 cm to 42.5 cm from the hemostasis valve 625 (the location of interventional device introduction into the access sheath) to the target site of between 32 and 43 cm. This distance is about a third the distance required in prior art technology.

A flush line 635 can be connected to the side of the hemostasis valve 625 and can have a stopcock 640 at its proximal or remote end. The flush-line 635 allows for the introduction of saline, contrast fluid, or the like, during the procedures. The flush line 635 can also allow pressure monitoring during the procedure. A dilator 645 having a tapered distal end 650 can be provided to facilitate introduction of the distal sheath 605 into the common carotid artery. The dilator 645 can be introduced through the hemostasis valve 625 so that the tapered distal end 650 extends through the distal end of the sheath 605, as best seen in FIG. 7A. The dilator 645 can have a central lumen to accommodate a guide wire. Typically, the guide wire is placed first into the vessel, and the dilator/sheath combination travels over the guide wire as it is being introduced into the vessel.

Optionally, a sheath stopper 705 such as in the form of a tube may be provided which is coaxially received over the exterior of the distal sheath 605, also as seen in FIG. 7A. The sheath stopper 705 is configured to act as a sheath stopper to prevent the sheath from being inserted too far into the vessel. The sheath stopper 705 is sized and shaped to be positioned over the sheath body 605 such that it covers a portion of the sheath body 605 and leaves a distal portion of the sheath body 605 exposed. The sheath stopper 705 may have a flared proximal end 710 that engages the adapter 620, and a distal end 715. Optionally, the distal end 715 may be beveled, as shown in FIG. 7B. The sheath stopper 705 may serve at least two purposes. First, the length of the sheath stopper 705 limits the introduction of the sheath 605 to the exposed distal portion of the sheath 605, as seen in FIG. 7A, such that the sheath insertion length is limited to the exposed distal portion of the sheath. In an embodiment, the sheath stopper limits the exposed distal portion to a range between 2 and 3 cm. In an embodiment, the sheath stopper limited the exposed distal portion to 2.5 cm. In other words, the sheath stopper may limit insertion of the sheath into the artery to a range between about 2 and 3 cm or to 2.5 cm. Second, the sheath stopper 705 can engage a pre-deployed puncture closure device disposed in the carotid artery wall, if present, to permit the sheath 605 to be withdrawn without dislodging the closure device. The sheath stopper 705 may be manufactured from clear material so that the sheath body may be clearly visible underneath the sheath stopper 705. The sheath stopper 705 may also be made from flexible material, or the sheath stopper 705 include articulating or sections of increased flexibility so that it allows the sheath to bend as needed in a proper position once inserted into the artery. The sheath stopper may be plastically bendable such that it can be bent into a desired shape such that it retains the shape when released by a user. The distal portion of the sheath stopper may be made from stiffer material, and the proximal portion may be made from more flexible material. In an embodiment, the stiffer material is 85 A durometer and the more flexible section is 50 A durometer. In an embodiment, the stiffer distal portion is 1 to 4 cm of the sheath stopper 705. The sheath stopper 705 may be removable from the sheath so that if the user desired a greater length of sheath insertion, the user could remove the sheath stopper 705, cut the length (of the sheath stopper) shorter, and re-assemble the sheath stopper 705 onto the sheath such that a greater length of insertable sheath length protrudes from the sheath stopper 705.

Figure 7C:
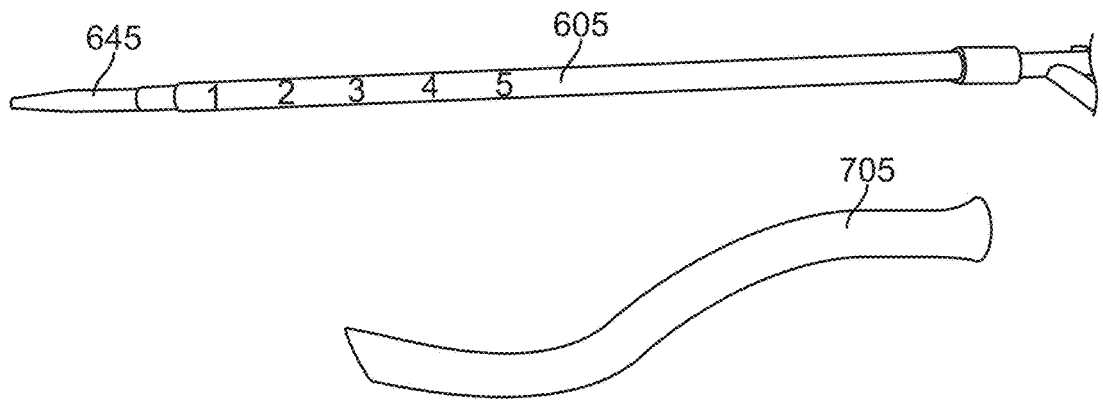
FIG. 7C show an embodiment of a sheath stopper.
Figure 7D:
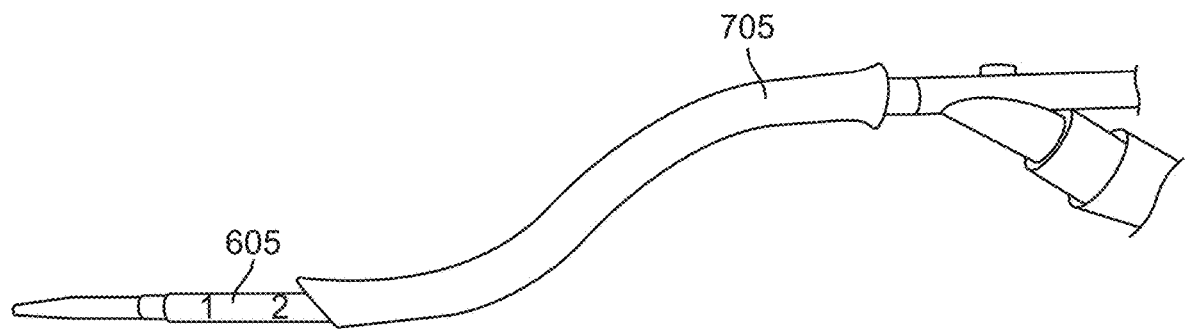
FIG. 7D shows the sheath stopper of FIG. 7C positioned on a sheath.

FIG. 7C shows another embodiment of a sheath stopper 705 positioned adjacent a sheath 605 with a dilator 645 positioned therein. The sheath stopper 705 of FIG. 7C may be deformed from a first shaped, such as a straight shape, into a second different from the first shape wherein the sheath stopper retains the second shape until a sufficient external force acts on the sheath stopper to change its shape. The second shape may be for example non-straight, curved, or an otherwise contoured or irregular shape. For example, FIG. 7C shows the sheath stopper 705 having multiple bends as well as straight sections. FIG. 7C shows just an example and it should be appreciated that the sheath stopper 705 may be shaped to have any quantity of bends along its longitudinal axis. FIG. 7D shows the sheath stopper 705 positioned on the sheath 605. The sheath stopper 705 has a greater stiffness than the sheath 605 such that the sheath 605 takes on a shape or contour that conforms to the shape of contour of the sheath stopper 705.

Figure 7E:
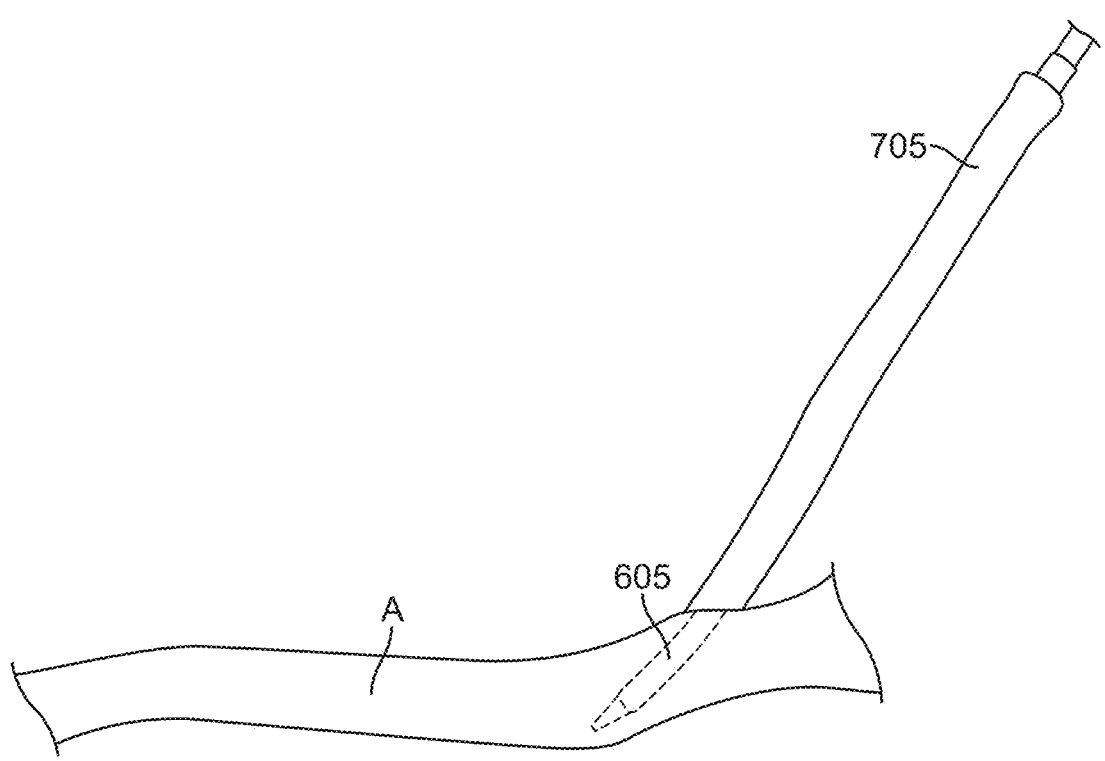
FIGS. 7E and 7F show the malleable sheath stopper in use.
Figure 7F:
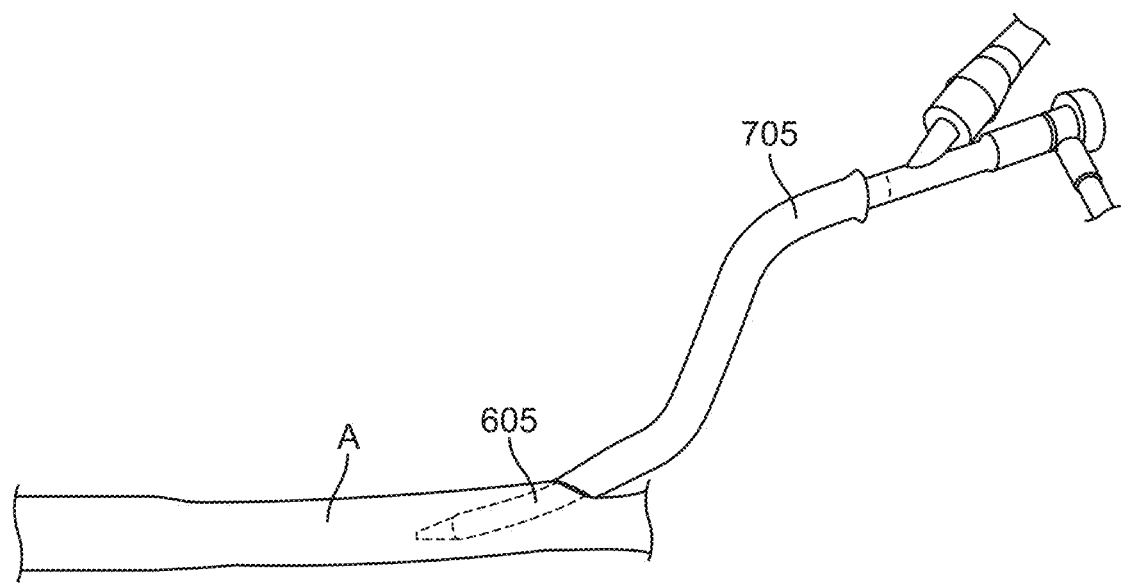

The sheath stopper 705 may be shaped according to an angle of the sheath insertion into the artery and the depth of the artery or body habitus of the patient. This feature reduces the force of the sheath tip in the blood vessel wall, especially in cases where the sheath is inserted at a steep angle into the vessel. The sheath stopper may be bent or otherwise deformed into a shape that assists in orienting the sheath coaxially with the artery being entered even if the angle of the entry into the arterial incision is relatively steep. The sheath stopper may be shaped by an operator prior to sheath insertion into the patient. Or, the sheath stopper may be shaped and/or re-shaped in situ after the sheath has been inserted into the artery. FIGS. 7E and 7F show an example of the malleable sheath stopper 705 in use. FIG. 7E shows the sheath stopper 705 positioned on the sheath 605 with the sheath stopper 705 in a straight shape. The sheath 605 takes on the straight shape of the sheath stopper 705 and is entering the artery A at a relatively steep angle such that the distal tip of the sheath 605 abuts or faces the wall of the artery. In FIG. 7F, a user has bent the sheath stopper 705 so as to adjust the angle of entry of the sheath 605 so that the longitudinal axis of the sheath 605 is more aligned with the axis of the artery A. In this manner, the sheath stopper 705 has been formed by a user into a shape that assists in directing the sheath 605 away from the opposing wall of the artery A and into a direction that is more coaxial with the axis of the artery A relative to the shape in FIG. 7E.

In an embodiment, the sheath stopper 705 is made from malleable material, or with an integral malleable component positioned on or in the sheath stopper. In another embodiment, the sheath stopper is constructed to be articulated using an actuator such as concentric tubes, pull wires, or the like. The wall of the sheath stopper may be reinforced with a ductile wire or ribbon to assist it in holding its shape against external forces such as when the sheath stopper encounters an arterial or entryway bend. Or the sheath stopper may be constructed of a homogeneous malleable tube material, including metal and polymer. The sheath stopper body may also be at least partially constructed of a reinforced braid or coil capable of retaining its shape after deformation.

Another sheath stopper embodiment is configured to facilitate adjustment of the sheath stopper position (relative to the sheath) even after the sheath is positioned in the vessel. One embodiment of the sheath stopper includes a tube with a slit along most or all of the length, so that the sheath stopper can be peeled away from the sheath body, moved forward or backwards as desired, and then re-positioned along the length of the sheath body. The tube may have a tab or feature on the proximal end so it may be grasped and more easily to peel away.

In another embodiment, the sheath stopper is a very short tube (such as a band), or ring that resides on the distal section of the sheath body. The sheath stopper may include a feature that could be grasped easily by forceps, for example, and pulled back or forwards into a new position as desired to set the sheath insertion length to be appropriate for the procedure. The sheath stopper may be fixed to the sheath body through either friction from the tube material, or a clamp that can be opened or closed against the sheath body. The clamp may be a spring-loaded clamp that is normally clamped onto the sheath body. To move the sheath stopper, the user may open the clamp with his or her fingers or an instrument, adjust the position of the clamp, and then release the clamp. The clamp is designed not to interfere with the body of the sheath.

In another embodiment, the sheath stopper includes a feature that allows suturing the sheath stopper and sheath to the tissue of the patient, to improve securement of the sheath and reduce risk of sheath dislodgement. The feature may be suture eyelets that are attached or molded into the sheath stopper tube.

Figure 9A:
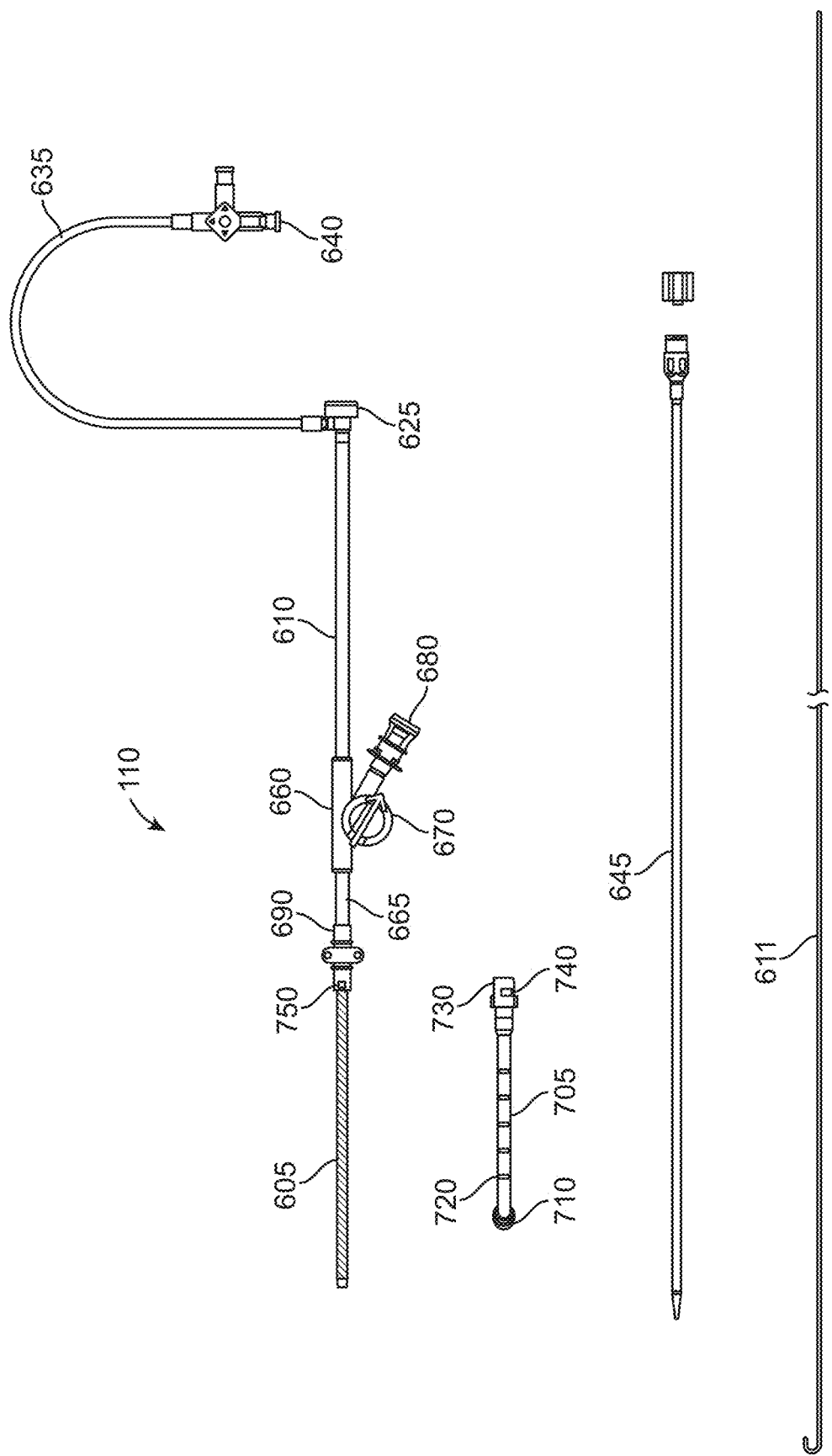
FIGS. 9A and 9B illustrate an additional embodiment of an arterial access device.

In another embodiment, as shown in FIG. 9A, the sheath stopper 705 includes a distal flange 710 sized and shaped to distribute the force of the sheath stopper over a larger area on the vessel wall and thereby reduce the risk of vessel injury or accidental insertion of the sheath stopper through the arteriotomy and into the vessel. The flange 710 may have a rounded shape or other atraumatic shape that is sufficiently large to distribute the force of the sheath stopper over a large area on the vessel wall. In an embodiment, the flange is inflatable or mechanically expandable. For example, the arterial sheath and sheath stopper may be inserted through a small puncture in the skin into the surgical area, and then expanded prior to insertion of the sheath into the artery.

The sheath stopper may include one or more cutouts or indents 720 along the length of the sheath stopper which are patterned in a staggered configuration such that the indents increase the bendability of the sheath stopper while maintaining axial strength to allow forward force of the sheath stopper against the arterial wall. The indents may also be used to facilitate securement of the sheath to the patient via sutures, to mitigate against sheath dislodgement. The sheath stopper may also include a connector element 730 on the proximal end which corresponds to features on the arterial sheath such that the sheath stopper can be locked or unlocked from the arterial sheath. For example, the connector element is a hub with generally L-shaped slots 740 that correspond to pins 750 on the hub to create a bayonet mount-style connection. In this manner, the sheath stopper can be securely attached to the hub to reduce the likelihood that the sheath stopper will be inadvertently removed from the hub unless it is unlocked from the hub.

The distal sheath 605 can be configured to establish a curved transition from a generally anterior-posterior approach over the common carotid artery to a generally axial luminal direction within the common carotid artery. Arterial access through the common carotid arterial wall either from a direct surgical cut down or a percutaneous access may require an angle of access that is typically larger than other sites of arterial access. This is due to the fact that the common carotid insertion site is much closer to the treatment site (i.e., carotid bifurcation) than from other access points. A larger access angle is needed to increase the distance from the insertion site to the treatment site to allow the sheath to be inserted at an adequate distance without the sheath distal tip reaching the carotid bifurcation. For example, the sheath insertion angle is typically 30-45 degrees or even larger via a transcarotid access, whereas the sheath insertion angle may be 15-20 degrees for access into a femoral artery. Thus the sheath must take a greater bend than is typical with introducer sheaths, without kinking and without causing undue force on the opposing arterial wall. In addition, the sheath tip desirably does not be abut or contact the arterial wall after insertion in a manner that would restrict flow into the sheath. The sheath insertion angle is defined as the angle between the luminal axis of the artery and the longitudinal axis of the sheath.

The sheath body 605 can be formed in a variety of ways to allow for this greater bend required by the angle of access.

For example, the sheath and/or the dilator may have a combined flexible bending stiffness less than typical introducer sheaths. In an embodiment, the sheath/dilator combination (i.e., the sheath with the dilator positioned inside the sheath) has a combined flexible stiffness (E*I) in the range of about 80 and 100 N–m$^2$×10$^{-6}$, where E is the elastic modulus and I is the area moment of inertia of the device. The sheath alone may have a bending stiffness in the range of about 30 to 40 N–m$^2$×10$^{-6}$ and the dilator alone has a bending stiffness in the range of about 40 to 60 N–m$^2$×10$^{-6}$. Typical sheath/dilator bending stiffnesses are in the range of 150 to 250 N–m$^2$×10$^{-6}$. The greater flexibility may be achieved through choice of materials or design of the reinforcement. For example, the sheath may have a ribbon coil reinforcement of stainless steel with dimensions 0.002" to 0.003" thick and 0.005" to 0.015" width, and with outer jacket durometer of between 40 and 55 D. In an embodiment, the coil ribbon is 0.003"×0.010", and the outer jacket durometer is 45 D. In an embodiment, the sheath 605 can be pre-shaped to have a curve or an angle some set distance from the tip, typically 0.5 to 1 cm. The pre-shaped curve or angle can typically provide for a turn in the range from 5° to 90°, preferably from 10° to 30°. For initial introduction, the sheath 605 can be straightened with an obturator or other straight or shaped instrument such as the dilator 645 placed into its lumen. After the sheath 605 has been at least partially introduced through the percutaneous or other arterial wall penetration, the obturator can be withdrawn to allow the sheath 605 to reassume its pre-shaped configuration into the arterial lumen. To retain the curved or angled shape of the sheath body after having been straightened during insertion, the sheath may be heat set in the angled or curved shape during manufacture. Alternately, the reinforcement structure may be constructed out of nitinol and heat shaped into the curved or angled shape during manufacture. Alternately, an additional spring element may be added to the sheath body, for example a strip of spring steel or nitinol, with the correct shape, added to the reinforcement layer of the sheath.

Other sheath configurations include having a deflection mechanism such that the sheath can be placed and the catheter can be deflected in situ to the desired deployment angle. In still other configurations, the catheter has a non-rigid configuration when placed into the lumen of the common carotid artery. Once in place, a pull wire or other stiffening mechanism can be deployed in order to shape and stiffen the sheath into its desired configuration. One particular example of such a mechanism is commonly known as "shape-lock" mechanisms as well described in medical and patent literature.

Another sheath configuration comprises a curved dilator inserted into a straight but flexible sheath, so that the dilator and sheath are curved during insertion. The sheath is flexible enough to conform to the anatomy after dilator removal.

Figure 7G:
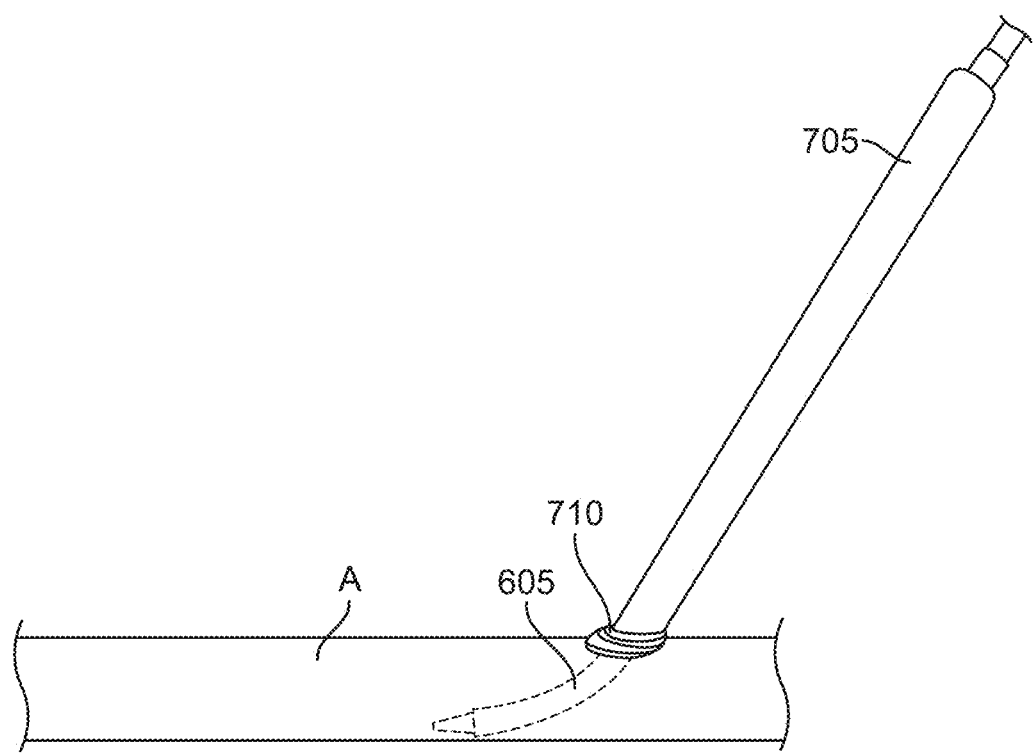
FIG. 7G shows an embodiment of a sheath with a flexible distal segment and a sheath stopper in use.

Another sheath embodiment is a sheath that includes one or more flexible distal sections, such that once inserted and in the angled configuration, the sheath is able to bend at a large angle without kinking and without causing undue force on the opposing arterial wall. In one embodiment, there is a distalmost section of sheath body 605 which is more flexible than the remainder of the sheath body. For example, the flexural stiffness of the distalmost section is one half to one tenth the flexural stiffness of the remainder of the sheath body 605. In an embodiment, the distalmost section has a flexural stiffness in the range 30 to 300 N–mm$^2$ and the remaining portion of the sheath body 605 has a flexural stiffness in the range 500 to 1500 N–mm$^2$, For a sheath configured for a CCA access site, the flexible, distal most section comprises a significant portion of the sheath body 222 which may be expressed as a ratio. In an embodiment, the ratio of length of the flexible, distalmost section to the overall length of the sheath body 222 is at least one tenth and at most one half the length of the entire sheath body 222. This change in flexibility may be achieved by various methods. For example, the outer jacket may change in durometer and/or material at various sections. Alternately, the reinforcement structure or the materials may change over the length of the sheath body. In an embodiment, the distal-most flexible section ranges from 1 cm to 3 cm. In an embodiment with more than one flexible section, a less flexible section (with respect to the distal-most section) may be 1 cm to 2 cm from the distal-most proximal section. In an embodiment, the distal flexible section has a bending stiffness in the range of about 30 to 50 N–m$^2$×10$^{-6}$ and the less flexible section has a bending stiffness in the range of about 50 and 100 N–m$^2$×10$^{-6}$. In another embodiment, a more flexible section is located between 0.5 and 1.5 cm for a length of between 1 and 2 cm, to create an articulating section that allows the distal section of the sheath to align more easily with the vessel axis though the sheath enters the artery at an angle. These configurations with variable flexibility sections may be manufactured in several manners. For example the reinforced, less flexible section may vary such that there is stiffer reinforcement in the proximal section and more flexible reinforcement in the distal section or in the articulating section. In an embodiment, an outermost jacket material of the sheath is 45 D to 70 D durometer in the proximal section and 80 A to 25 D in the distalmost section. In an embodiment, the flexibility of the sheath varies continuously along the length of the sheath body. FIG. 7G shows such a sheath inserted in the artery, with the flexible distal section allowing the sheath body to bend and the distal tip to be in general alignment with the vessel lumen. In an embodiment, the distal section is made with a more flexible reinforcement structure, either by varying the pitch of a coil or braid or by incorporating a cut hypotube with differing cut patterns. Alternately the distal section has a different reinforcement structure than the proximal section.

In an embodiment, the distal sheath tapered tip is manufactured from harder material than the distal sheath body. A purpose of this is to facilitate ease of sheath insertion by allowing for a very smooth taper on the sheath and reduce the change of sheath tip distortion or ovalizing during and after sheath insertion into the vessel. In one example the distal tapered tip material is manufactured from a higher durometer material, for example a 60-72 D shore material. In another example, distal tip is manufactured from a separate material, for example HDPE, stainless steel, or other suitable polymers or metals. In an additional embodiment, the distal tip is manufactured from radiopaque material, either as an additive to the polymer material, for example tungsten or barium sulfate, or as an inherent property of the material (as is the case with most metal materials).

In another embodiment, the dilator 645 may also have variable stiffness. For example the tapered tip 650 of the dilator may be made from more flexible material than the proximal portion of the dilator, to minimize the risk of vessel injury when the sheath and dilator are inserted into the artery. In an embodiment, the distal flexible section has a bending stiffness in the range of about 45 to 55 N–m$^2$×10$^{-6}$ and a less flexible proximal section has a bending stiffness in the range of about 60 and 90 N–m$^2$×10$^{-6}$. The taper shape of the dilator may also be optimized for transcarotid access. For example, to limit the amount of sheath and dilator tip that enter the artery, the taper length and the amount of the dilator that extends past the sheath should be shorter than typical introducer sheaths. For example, the taper length may be 1 to 1.5 cm, and extend 1.5 to 2 cm from the end of the sheath body. In an embodiment, the dilator contains a radiopaque marker at the distal tip so that the tip position is easily visible under fluoroscopy.

In another embodiment, the introducer guide wire is optimally configured for transcarotid access. Typically when inserting an introducer sheath into a vessel, an introducer guide wire is first inserted into the vessel. This may be done either with a micropuncture technique or a modified Seldinger technique. Usually there is a long length of vessel in the direction that the sheath is to be inserted into which an introducer guidewire may be inserted, for example into the femoral artery. In this instance, a user may introduce a guide wire between 10 and 15 cm or more into the vessel before inserting the sheath. The guide wire is designed to have a flexible distal section so as not to injure the vessel when being introduced into the artery. The flexible section of an introducer sheath guide wire is typically 5 to 6 cm in length, with a gradual transition to the stiffer section. Inserting the guide wire 10 to 15 cm means the stiffer section of the guide wire is positioned in the area of the puncture and allows a stable support for subsequent insertion of the sheath and dilator into the vessel. However, in the case of transcarotid sheath insertion into the common carotid artery, there is a limit on how much guide wire may be inserted into the carotid artery. In cases with carotid artery disease at the bifurcation or in the internal carotid artery, it is desirable to minimize the risk of emboli by inserting the wire into the external carotid artery (ECA), which would mean only about 5 to 7 cm of guide wire insertion, or to stop it before it reaches the bifurcation, which would be only 3 to 5 cm of guide wire insertion. Thus, a transcarotid sheath guidewire may have a distal flexible section of between 3 and 4 cm, and/or a shorter transition to a stiffer section. Alternately, a transcarotid sheath guidewire has an atraumatic tip section but have a very distal and short transition to a stiffer section. For example, the soft tip section is 1.5 to 2.5 cm, followed by a transition section with length from 3 to 5 cm, followed by a stiffer proximal segment, with the stiffer proximal section comprising the remainder of the wire.

In addition to the configurations described above, features may be included in the introducer guide wire, or the micropuncture catheter, or the micropuncture catheter guide wire, to prevent inadvertent advancement of these devices into the diseased portion of the carotid artery. For example a stopper feature may be positioned over the introducer guide wire, micropuncture catheter and/or the micropuncture guide wire to limit the length these devices can be inserted. The stopper feature may be, for example, a short section of tubing which can be slideably positioned on the device, and once positioned remains in place on the device via friction. For example, the stopper feature may be manufactured from soft polymer material such as silicone rubber, polyurethane, or other thermoplastic elastomer. The stopper feature may have an inner diameter the same size or even slightly smaller than the device diameter. Alternately the stopper feature may be configured to clamp on to the device, such that the user must squeeze or otherwise unlock the stopper feature to unclamp and reposition the device, and then release or otherwise relock the stopper feature onto the device. The stopper feature may be positioned for optimal entry into the vessel based on location of the puncture site, distance of the bifurcation with respect to the puncture site, and amount of disease in the carotid bifurcation.

The sheath guide wire may have guide wire markings to help the user determine where the tip of the wire is with respect to the dilator. For example, there may be a marking on the proximal end of the wire corresponding to when the tip of the wire is about to exit the micro access cannula tip. This marking would provide rapid wire position feedback to help the user limit the amount of wire insertion. In another embodiment, the wire may include an additional mark to let the user know the wire has exited the cannula by a set distance, for example 5 cm. Alternately, the introducer guide wire, micropuncture catheter and/or the micropuncture guide wire may be constructed or have sections constructed out of material which is markable with a marking pen, wherein the mark is easily visible in a cath lab or operating room (OR) setting. In this embodiment, the user pre-marks the components based on the anatomic information as described above, and uses these marks to determine the amount of maximal insertion for each component. For example, the guide wires may have a white coating around the section to be marked.

In an embodiment, the sheath has built-in puncturing capability and atraumatic tip analogous to a guide wire tip. This eliminates the need for needle and wire exchange currently used for arterial access according to the micropuncture technique, and can thus save time, reduce blood loss, and require less surgeon skill.

In another embodiment, the sheath dilator is configured to be inserted over an 0.018" guide wire for transcarotid access. Standard sheath insertion using a micropuncture kit requires first insertion of an 0.018" guide wire through a 22 Ga needle, then exchange of the guide wire to an 0.035" or 0.038" guide wire using a micropuncture catheter, and finally insertion of the sheath and dilator over the 0.035" or 0.038" guide wire. There exist sheaths which are insertable over a 0.018" guidewire, thus eliminating the need for the wire exchange. These sheaths, usually labeled "transradial" as they are designed for insertion into the radial artery, typically have a longer dilator taper, to allow an adequate diameter increase from the 0.018" wire to the body of the sheath. Unfortunately for transcarotid access, the length for sheath and dilator insertion is limited and therefore these existing sheaths are not appropriate. Another disadvantage is that the 0.018" guide wire may not have the support needed to insert a sheath with a sharper angle into the carotid artery. In the embodiment disclosed here, a transcarotid sheath system includes a sheath body, a sheath dilator, and an inner tube with a tapered distal edge that slidably fits inside the sheath dilator and can accommodate an 0.018" guide wire.

To use this sheath system embodiment, the 0.018" guide wire is first inserted into the vessel through a 22 Ga needle. The sheath system which is coaxially assembled is inserted over the 0.018" wire. The inner tube is first advanced over the 0.018" wire which essentially transforms it into the equivalent of an 0.035" or 0.038" guide wire in both outer diameter and mechanical support. It is locked down to the 0.018" wire on the proximal end. The sheath and dilator are then advanced over the 0.018" wire and inner tube into the vessel. This configuration eliminates the wire exchange step without the need for a longer dilator taper as with current transradial sheaths and with the same guide wire support as standard introducer sheaths. As described above, this configuration of sheath system may include stopper features which prevent inadvertent advancement too far of the 0.018" guide wire and/or inner tube during sheath insertion. Once the sheath is inserted, the dilator, inner tube, and 0.018" guide wire are removed.

FIG. 8A shows another embodiment of the arterial access device 110. This embodiment is substantially the same as the embodiment shown in FIG. 6A, except that the distal sheath 605 includes an occlusion element 129 for occluding flow through, for example the common carotid artery. If the occluding element 129 is an inflatable structure such as a balloon or the like, the sheath 605 can include an inflation lumen that communicates with the occlusion element 129. The occlusion element 129 can be an inflatable balloon, but it could also be an inflatable cuff, a conical or other circumferential element which flares outwardly to engage the interior wall of the common carotid artery to block flow therepast, a membrane-covered braid, a slotted tube that radially enlarges when axially compressed, or similar structure which can be deployed by mechanical means, or the like. In the case of balloon occlusion, the balloon can be compliant, non-compliant, elastomeric, reinforced, or have a variety of other characteristics. In an embodiment, the balloon is an elastomeric balloon which is closely received over the exterior of the distal end of the sheath prior to inflation. When inflated, the elastomeric balloon can expand and conform to the inner wall of the common carotid artery. In an embodiment, the elastomeric balloon is able to expand to a diameter at least twice that of the non-deployed configuration, frequently being able to be deployed to a diameter at least three times that of the undeployed configuration, more preferably being at least four times that of the undeployed configuration, or larger.

As shown in FIG. 8B, the distal sheath 605 with the occlusion element 129 can have a stepped or other configuration having a reduced diameter distal region 630. The distal region 630 can be sized for insertion into the carotid artery with the remaining proximal region of the sheath 605 having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm. The relatively short length of the reduced-diameter distal section 630 permits this section to be positioned in the common carotid artery CCA via the transcarotid approach with reduced risk that the distal end of the sheath 605 will contact the bifurcation B.

FIG. 2B shows an alternative embodiment, wherein the occlusion element 129 can be introduced into the carotid artery on a second sheath 112 separate from the distal sheath 605 of the arterial access device 110. The second or "proximal" sheath 112 can be adapted for insertion into the common carotid artery in a proximal or "downward" direction away from the cerebral vasculature. The second, proximal sheath can include an inflatable balloon 129 or other occlusion element, generally as described above. The distal sheath 605 of the arterial access device 110 can be then placed into the common carotid artery distal of the second, proximal sheath and generally oriented in a distal direction toward the cerebral vasculature. By using separate occlusion and access sheaths, the size of the arteriotomy needed for introducing the access sheath can be reduced.

FIG. 2C shows yet another embodiment of a two arterial sheath system, wherein the interventional devices are introduced via an introducer sheath 114 separate from the distal sheath 605 of the arterial device 110. A second or "distal" sheath 114 can be adapted for insertion into the common carotid artery distal to the arterial access device 110. As with the previous embodiment, the use of two separate access sheaths allows the size of each arteriotomy to be reduced.

In a situation with a sharp sheath insertion angle and/or a short length of sheath inserted in the artery, such as one might see in a transcarotid access procedure, the distal tip of the sheath has a higher likelihood of being partially or totally positioned against the vessel wall, thereby restricting flow into the sheath. In an embodiment, the sheath is configured to center the tip in the lumen of the vessel. One such embodiment includes a balloon such as the occlusion element 129 described above. In another embodiment, a balloon may not be occlusive to flow but still center the tip of the sheath away from a vessel wall, like an inflatable bumper. In another embodiment, expandable features are situated at the tip of the sheath and mechanically expanded once the sheath is in place. Examples of mechanically expandable features include braided structures or helical structures or longitudinal struts which expand radially when shortened.

In an embodiment, occlusion of the vessel proximal to the distal tip of the sheath may be done from the outside of the vessel, as in a Rummel tourniquet or vessel loop proximal to sheath insertion site. In an alternate embodiment, an occlusion device may fit externally to the vessel around the sheath tip, for example an elastic loop, inflatable cuff, or a mechanical clamp that could be tightened around the vessel and distal sheath tip. In a system of flow reversal, this method of vessel occlusion minimizes the area of static blood flow, thereby reducing risk of thrombus formation, and also ensure that the sheath tip is axially aligned with vessel and not partially or fully blocked by the vessel wall.

Figure 9B:
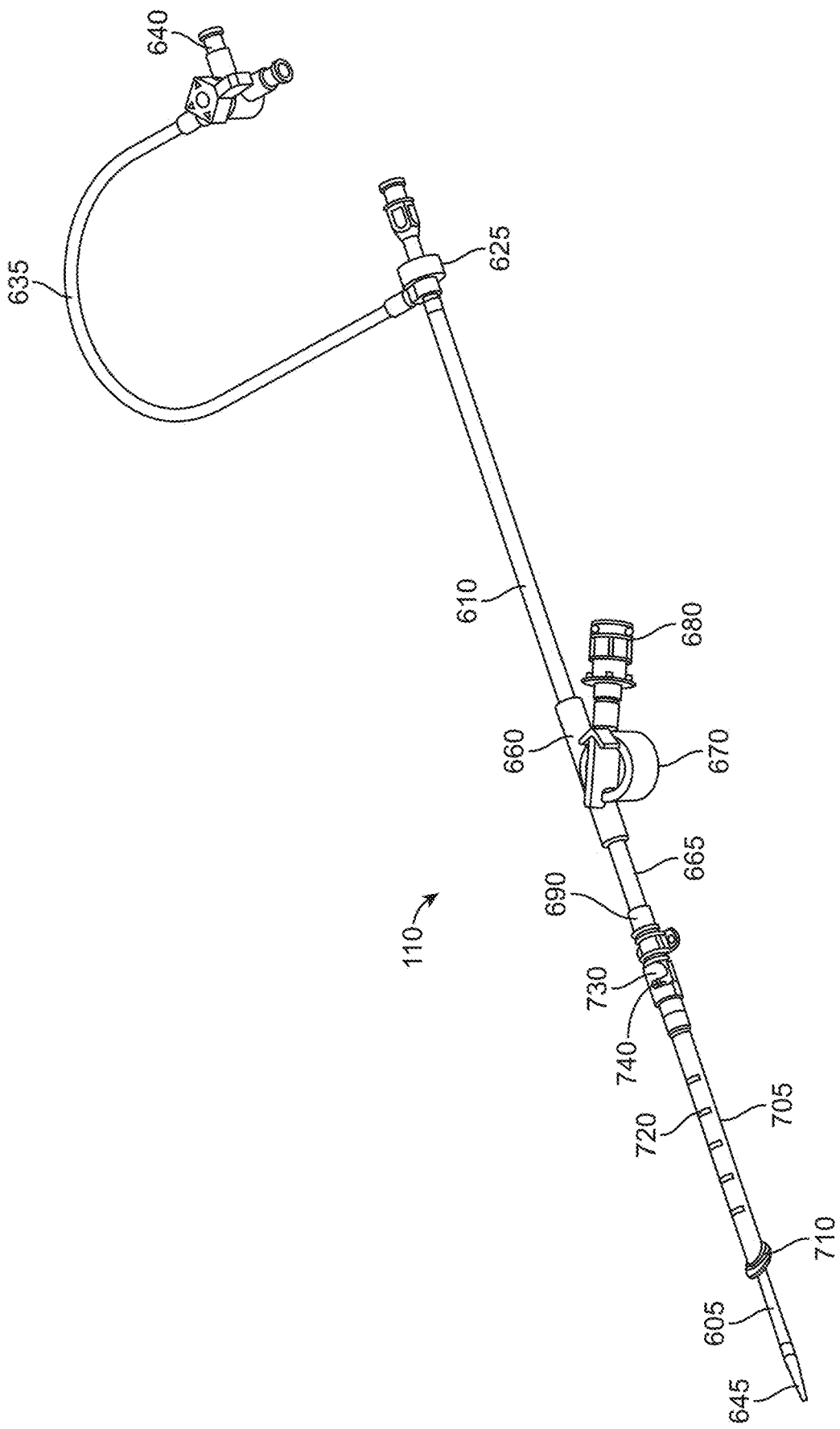

Another arterial access device is shown in FIGS. 9A-9D. This configuration has a different style of connection to the flow shunt than the versions described previously. FIG. 9A shows the components of the arterial access device 110 including arterial access sheath 605, sheath dilator 645, sheath stopper 705, and sheath guidewire 611. FIG. 9B shows the arterial access device 110 as it would be assembled for insertion over the sheath guide wire 611 into the carotid artery. After the sheath is inserted into the artery and during the procedure, the sheath guide wire 611 and sheath dilator 705 are removed. In this configuration, the sheath has a sheath body 605, proximal extension 610, and proximal hemostasis valve 625 with flush line 635 and stopcock 640. The proximal extension 610 extends from a Y-adapter 660 to the hemostasis valve 625 where the flush line 635 is connected. The sheath body 605 is the portion that is sized to be inserted into the carotid artery and is actually inserted into the artery during use.

Figure 9C:
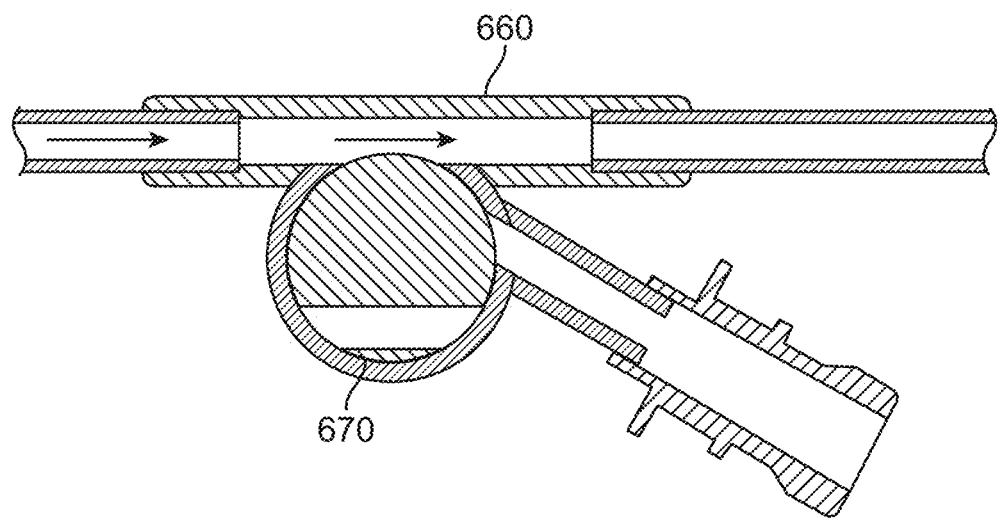
FIGS. 9C and 9D illustrate an embodiment of a valve on the arterial access device.
Figure 9D:
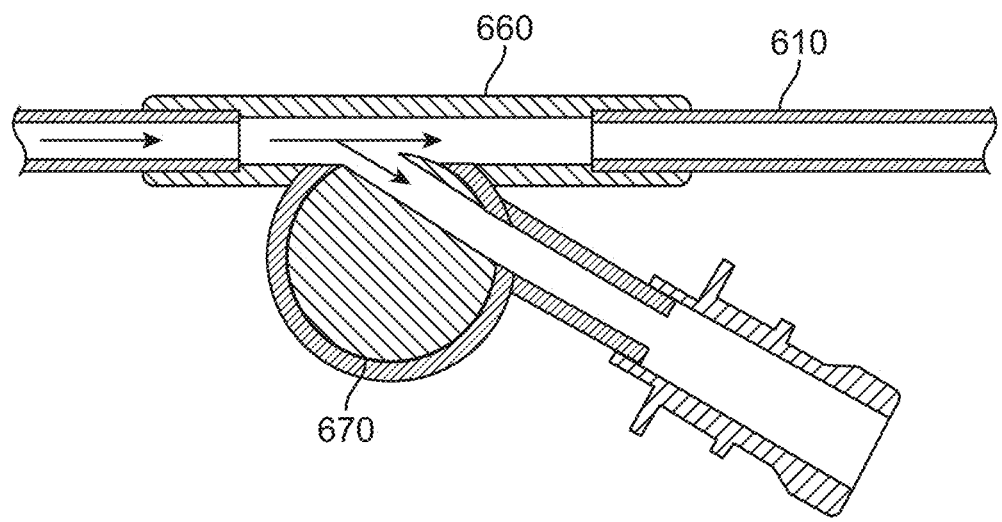

Instead of a Y-connector with a flow line connection terminating in a valve, the sheath has a Y-adaptor 660 that connects the distal portion of the sheath to the proximal extension 610. The Y-adapter can also include a valve 670 that can be operated to open and close fluid connection to a connector or hub 680 that can be removably connected to a flow line such as a shunt. The valve 670 is positioned immediately adjacent to an internal lumen of the adapter 660, which communicates with the internal lumen of the sheath body 605. FIGS. 9C and 9D show details in cross section of the Y-adaptor 660 with the valve 670 and the hub 680. FIG. 9C shows the valve closed to the connector. This is the position that the valve would be in during prep of the arterial sheath. The valve is configured so that there is no potential for trapped air during prep of the sheath. FIG. 9D shows the valve open to the connector. This position would be used once the flow shunt 120 is connected to hub 680, and would allow blood flow from the arterial sheath into the shunt. This configuration eliminates the need to prep both a flush line and flow line, instead allowing prep from the single flush line 635 and stopcock 640. This single-point prep is identical to prep of conventional introducer sheaths which do not have connections to shunt lines, and is therefore more familiar and convenient to the user. In addition, the lack of flow line on the sheath makes handling of the arterial sheath easier during prep and insertion into the artery.

With reference again to FIG. 9A, the sheath may also contain a second more distal connector 690, which is separated from the Y-adaptor 660 by a segment of tubing 665. A purpose of this second connector and the tubing 665 is to allow the valve 670 to be positioned further proximal from the distal tip of the sheath, while still limiting the length of the insertable portion of the sheath 605, and therefore allow a reduced level of exposure of the user to the radiation source as the flow shunt is connected to the arterial sheath during the procedure. In an embodiment, the distal connector 690 contains suture eyelets to aid in securement of the sheath to the patient once positioned.

During a transcarotid artery revascularization (TCAR) procedure, the arterial sheath 605 can be inserted into the common carotid artery (CCA) of the patient. As described elsewhere herein, to achieve reverse flow of blood, the CCA may be occluded to stop antegrade blood flow from the aorta through the CCA. Flow through the CCA can be occluded with an external vessel loop or tape, a vascular clamp, an internal occlusion member such as a balloon, or other type of occlusion means. When flow through CCA is blocked, the natural pressure gradient between the internal carotid artery (ICA) and the venous system will cause blood to flow in a retrograde or reverse direction from the cerebral vasculature. Blood from the ICA and the external carotid artery (ECA) flows in a retrograde direction and the systems described herein allow the retrograde blood to flow into the sheath 605, through the flow controller 1130, the venous sheath 910, and then returned into the patient's femoral vein as described elsewhere herein. Loose embolic material can be carried with the retrograde blood flow into the arterial sheath 605.

Figure 13A:
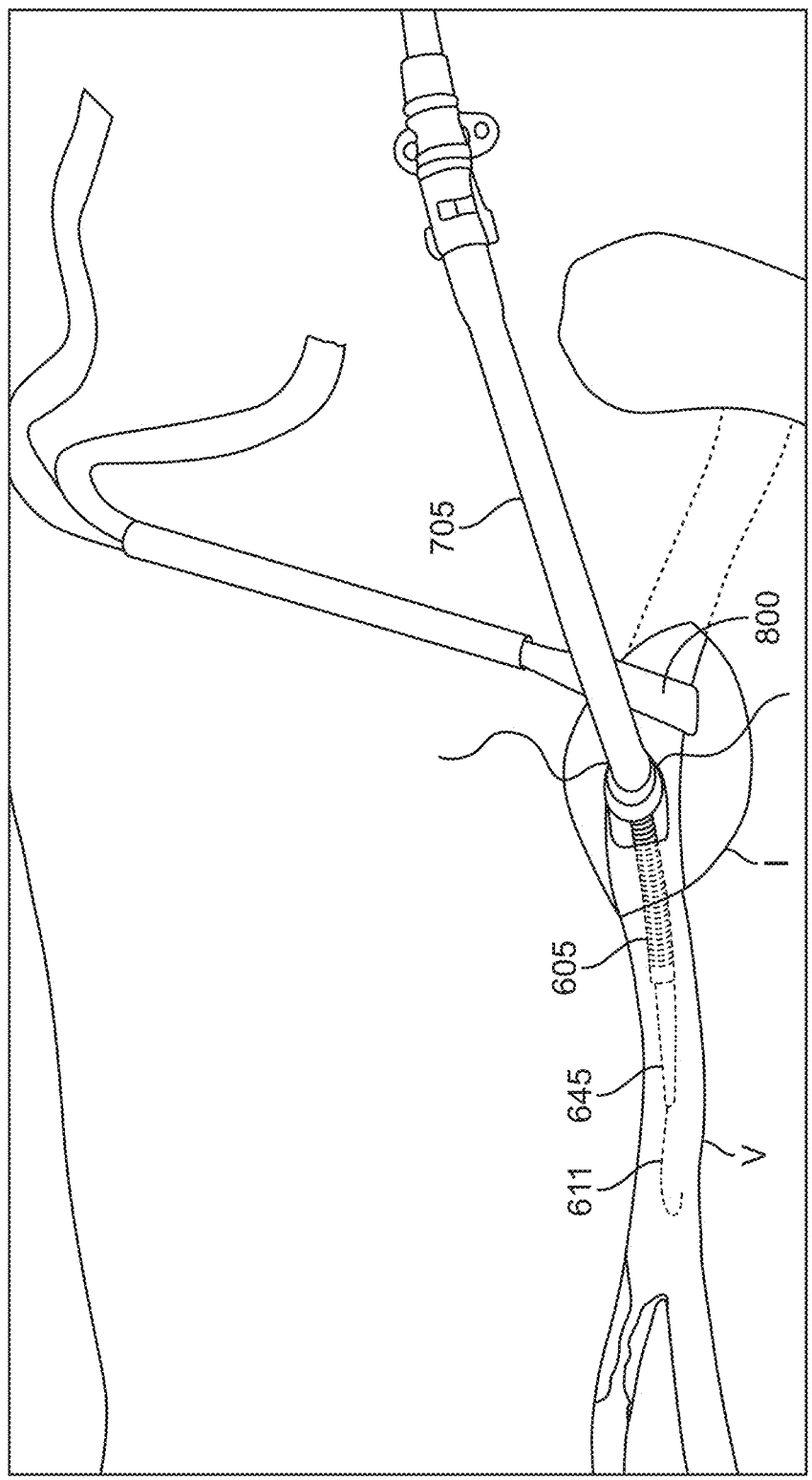
Figure 13B:
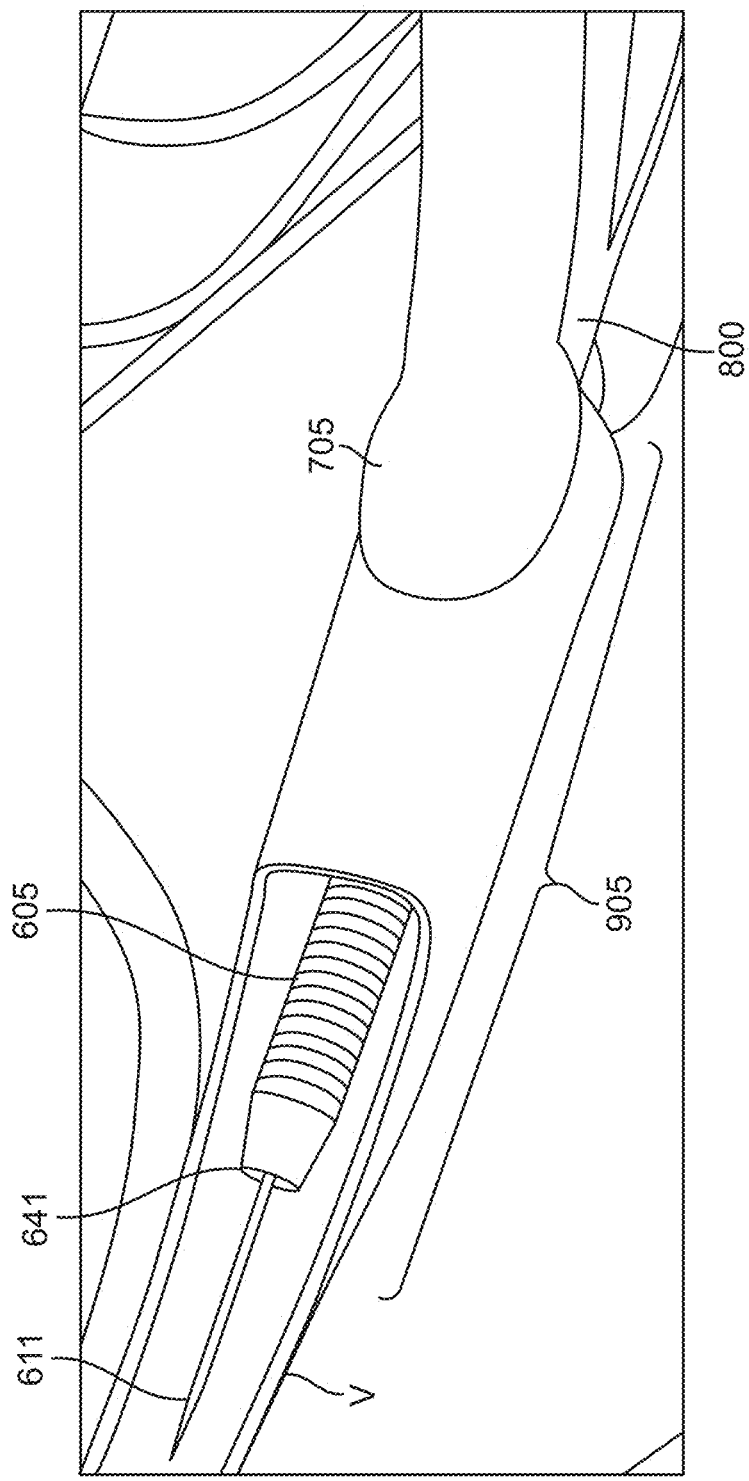

FIGS. 13A-13B illustrate an arterial sheath 605 inserted within a vessel V, such as the carotid artery, exposed through an incision I. A sheath guidewire 611 and an arterial access sheath dilator 645 protrude out from a distal opening 641 near the distal region 630 of the sheath 605. A sheath stopper 705 can be used with the sheath 605, as described elsewhere herein. Manual occlusion of the vessel V by a clinician at an occlusion location proximal to the distal tip of the sheath 605 may be provided from the outside of the vessel V using a vascular clamp 800, such as a Rummel tourniquet or vessel loop positioned proximal to the sheath insertion site. An occlusion device may fit externally to the vessel V around the sheath tip, for example, an elastic loop, inflatable cuff, or a mechanical clamp that can be tightened around the vessel and the distal sheath tip. In a flow reversal system, this type of vessel occlusion can minimize creation of a zone of static blood flow, thereby reducing the risk of thrombus formation. This also ensures that the sheath tip is axially aligned with the vessel V and avoids partially or fully blocking the distal opening 641 by the vessel wall.

Despite these clamp techniques, the zone of static blood flow can still be created. FIG. 13B illustrates a system for retrograde blood flow into the distal opening 641 of the arterial sheath 605 after removal of the access sheath dilator 645. The location of the vascular clamp 800 in FIG. 13B is partially obscured by the presence of the sheath stopper 705. Embolic material within the retrograde blood flow may drift and be trapped within a zone 905 of static blood flow within the vessel V between the distal opening 641 of the arterial sheath 605 and the location of the vascular clamp 800 proximal to the sheath insertion location. Embolic material may remain within this zone 905 rather than flow into the distal opening 641 of the arterial sheath 605. Once the target vessel has been treated by the operator, the vascular clamp 800 is released permitting resumption of antegrade blood flow. Embolic material from this zone 905 may be carried into the neurovasculature when the vascular clamp 800 is released and antegrade blood flow resumes. The trapped embolic material within the zone 905 may cause an ischemic event despite the use of reverse flow embolic protection during the procedure because it fails to ever enter the lumen of the arterial sheath 605 during the period of retrograde flow.

FIG. 13C illustrates a distal end region of an implementation of an arterial sheath 605 having a fenestrated distal portion 643. The fenestrated distal portion 643 of the sheath 605 includes one or more side holes or fenestrations 646 in the side wall of the sheath 605. As described above, blood from zone 905 may potentially contain embolic material that would otherwise flow into the neurovasculature upon release of the vascular clamp 800. Material from this zone 905 can enter the sheath 605 through the fenestrations 646 in the sidewall of the sheath 605. The fenestrations 646 can also maintain flow into the sheath 605 even if the distal opening 641 at the distal tip of sheath 605 is partially or fully blocked by arterial wall. Blood and any embolic material can flow into the lumen of the sheath 604 through the one or more fenestrations 646 and transported proximally through the embolic protection system with the retrograde blood flow.

The location, distribution, shape, and size of the fenestrations 646 can vary. The fenestrations 646 can be distributed longitudinally and/or circumferentially along the distal portion 643 of the arterial sheath 605. The location and distribution of the fenestrations 646 can be selected based on whether a sheath stopper 705 is to be used with the sheath 605. For example, a sheath stopper 705 can be positioned on the arterial sheath 605 to limit an insertion depth of the sheath 605 into the vessel. In some implementations, the sheath stopper 705 limits the insertion depth to 2.5 cm. Thus, the one or more fenestrations 646 can be distributed along the distal-most 2.5 cm of the sheath 605. Fenestrations 646 may also be distributed along the sheath 605 over a greater distance. The proximal sheath fenestrations 646 sitting external to the vessel can be blocked by a sleeve or other feature of the system thereby preventing leakage.

Figure 13D:
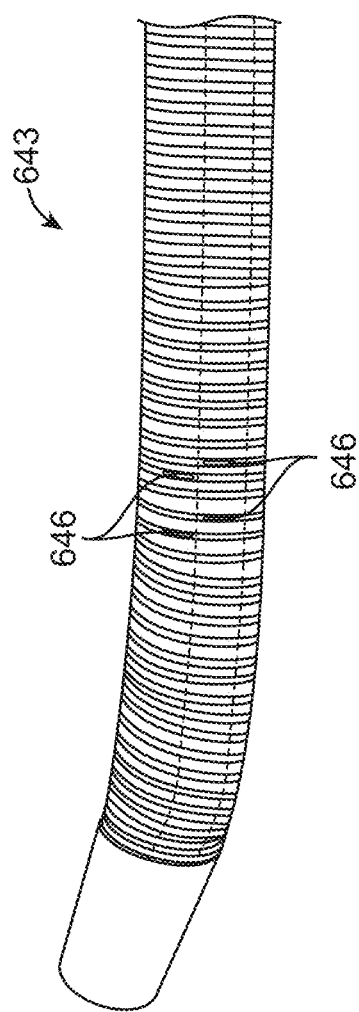

As described elsewhere herein, the sheath 605 can be reinforced to provide improved flexibility and kink-resistance. The reinforcement can be a spiral-wound stainless steel ribbon, braid, or mesh as is known in the art. The one or more fenestrations 646 can be positioned such that they extend through and/or align with the side wall in the space(s) between the reinforcement material such that the fenestrations 646 and the space(s) collectively form passageways through which fluid can flow into the internal lumen of the sheath 605. The spaces within the reinforcement layer can include gaps between individual coils, circular or diamond-shaped holes through the braid or mesh, etc. The fenestrations 646 through the sidewall of the sheath 605 align with these spaces or gaps in the reinforcement layer thereby providing additional entrance points for blood and embolic material while maintaining the structural benefits of the reinforcement layer. The orientation of the fenestrations 646 can be such that they align with these spaces between the reinforcement material (see FIG. 13D). The fenestrations 646 can vary in their number, size, and shape, including circular, oval, rectangular, or other elongate shape. The elongate fenestrations 646 can extend along an axis perpendicular or at an angle to the longitudinal axis of the sheath overall such that they fit within or align with the spaces between the reinforcement layer.

For example, as described elsewhere herein the arterial sheath 605 may have a ribbon coil reinforcement of stainless steel with dimensions 0.002" to 0.003" thick and 0.005" to 0.015" width. In an embodiment, the coil ribbon is 0.003"×0.010". The nominal spacing between the reinforcement coils of the sheath 605 can vary, but generally is about 0.020". The elongated fenestrations 646 can thus have a width of about this size such that they extend through the wall between the reinforcement coils. In some implementations, the fenestrations 646 can be between about 0.010" to about 0.080", with a nominal range of about 0.015"-0.020". Depending on the spacing between the reinforcement, the elongated fenestrations 646 can have a size between 0.015"×0.030" to about 0.040"×0.080". Elongated fenestrations 646 that fit between or within the gaps in the reinforcement material can be up to about 0.020", with a maximum envisioned dimension of about 0.020"×0.080". It may be possible to vary the pitch of the coils as well as the width of the coil ribbon to adjust and optimize the flexibility and performance of the sheath 605 and the size of the fenestrations 646. For example, the reinforcement material can be a coil ribbon.

The width between the individual coils can be increased near where one or more fenestrations 646 would extend through the wall of the sheath 605. The width near this location can be increased from 0.020" to 0.050". The fenestrations 646 need not be limited to the location of the gaps in the reinforcement. For example, the reinforcement material can be a wire or polymer mesh. One or more regions of the mesh can be cut to create a larger sized space (while taking into consideration maintaining the overall functionality of the sheath) and the one or more fenestrations 646 co-located to that larger space.

The embolic protection system can include a passive method of driving retrograde blood flow into the distal opening 641 at the sheath tip and the fenestrations 646 in the distal end region 643, for example, by relying upon arterial-venous pressure differential. The embolic protection system can also incorporate active aspiration of blood through the arterial sheath 605 to enhance the withdrawal of embolic material into the distal opening 641 as well as through the fenestrations 646. The fenestrations 646 can also be useful in delivering materials into the vessel through the fenestrations 646. In some implementations, a gentle injection of saline through the lumen of the sheath 605 into the vessel through the fenestrations 646 can cause turbulence/agitation within the zone 905 of static blood. The flush of fluid can induce any particulates trapped within the zone 905 to be drawn into the fluid flow path and to enter the sheath 605, either through the fenestrations 646 upon resumption of aspiration forces or through the distal opening 641.

The arterial sheath 605 having one or more fenestrations 646 on the distal end portion 643 can be delivered in combination with a delivery tool (not shown) configured to facilitate a smooth delivery into the vessel and prevent the edges of the fenestrations 646 from catching on tissue as the sheath 605 is inserted through the vessel wall. The fenestrations 646 may also impact delivery of guidewires, balloon catheters, or other devices through the lumen of the arterial sheath 605. As such, the arterial sheath 605 can incorporate a secondary sleeve on the inside or outside of the arterial sheath 605. The secondary sleeve can be initially positioned such that the sheath fenestrations 646 are covered or closed, thereby permitting smooth passage of guidewires and other devices through the lumen of the arterial sheath 605. Once the devices have been passed through the sheath, the secondary sleeve can be rotated, advanced and/or retracted to uncover or open the fenestrations. A lubricious coating of material on the inner and/or outer surfaces of the sheath 605 can be provided to improve advancement of materials. In addition, a coating of heparin can be provided to decrease the likelihood of thrombus formation on the sheath 605.

Venous Return Device

Figure 10A:
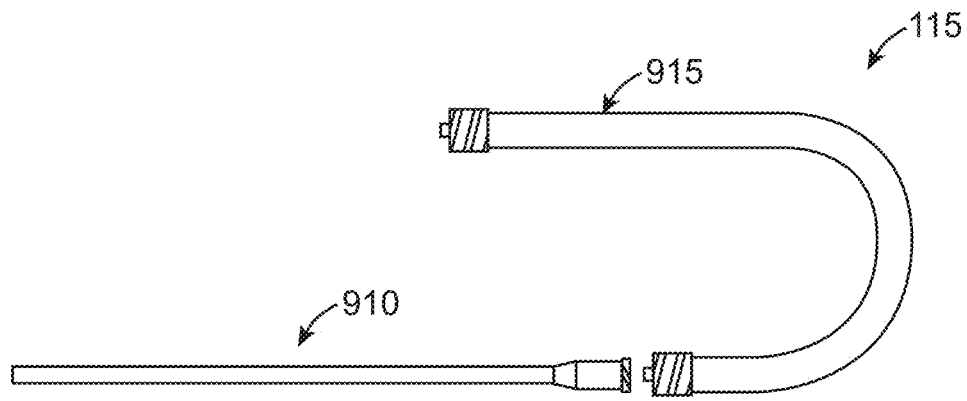
Figure 10B:
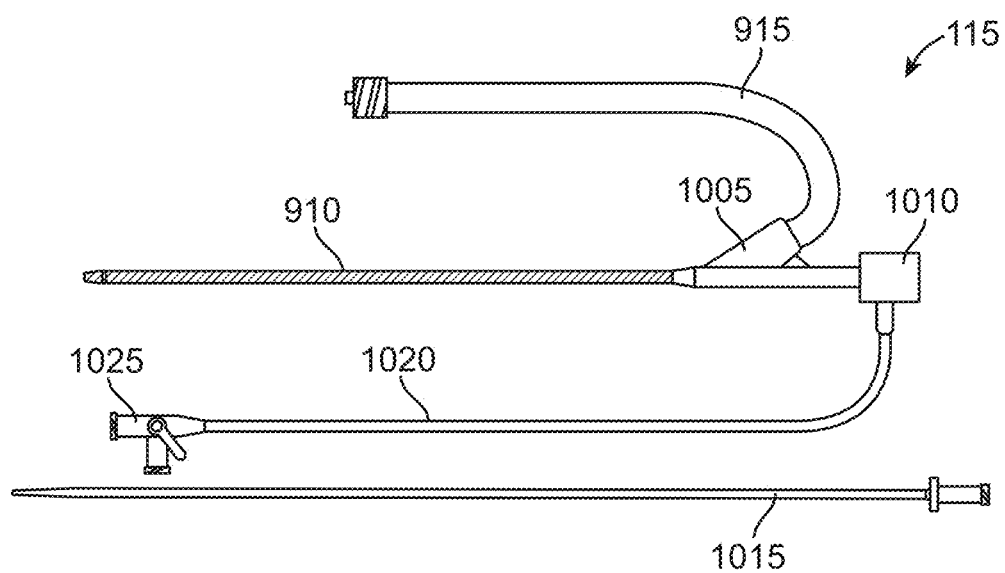

Referring now to FIG. 10, the venous return device 115 can comprise a distal sheath 910 and a flow line 915, which connects to and forms a leg of the shunt 120 when the system is in use. The distal sheath 910 is adapted to be introduced through an incision or puncture into a venous return location, such as the jugular vein or femoral vein. The distal sheath 910 and flow line 915 can be permanently affixed, or can be attached using a conventional luer fitting, as shown in FIG. 10A. Optionally, as shown in FIG. 10B, the sheath 910 can be joined to the flow line 915 by a Y-connector 1005. The Y-connector 1005 can include a hemostasis valve 1010. The venous return device also comprises a venous sheath dilator 1015 and an introducer guide wire 611 to facilitate introduction of the venous return device into the internal jugular vein or other vein. As with the arterial access dilator 645, the venous dilator 1015 includes a central guide wire lumen so the venous sheath and dilator combination can be placed over the guide wire 611. Optionally, the venous sheath 910 can include a flush line 1020 with a stopcock 1025 at its proximal or remote end.

Figure 10D:
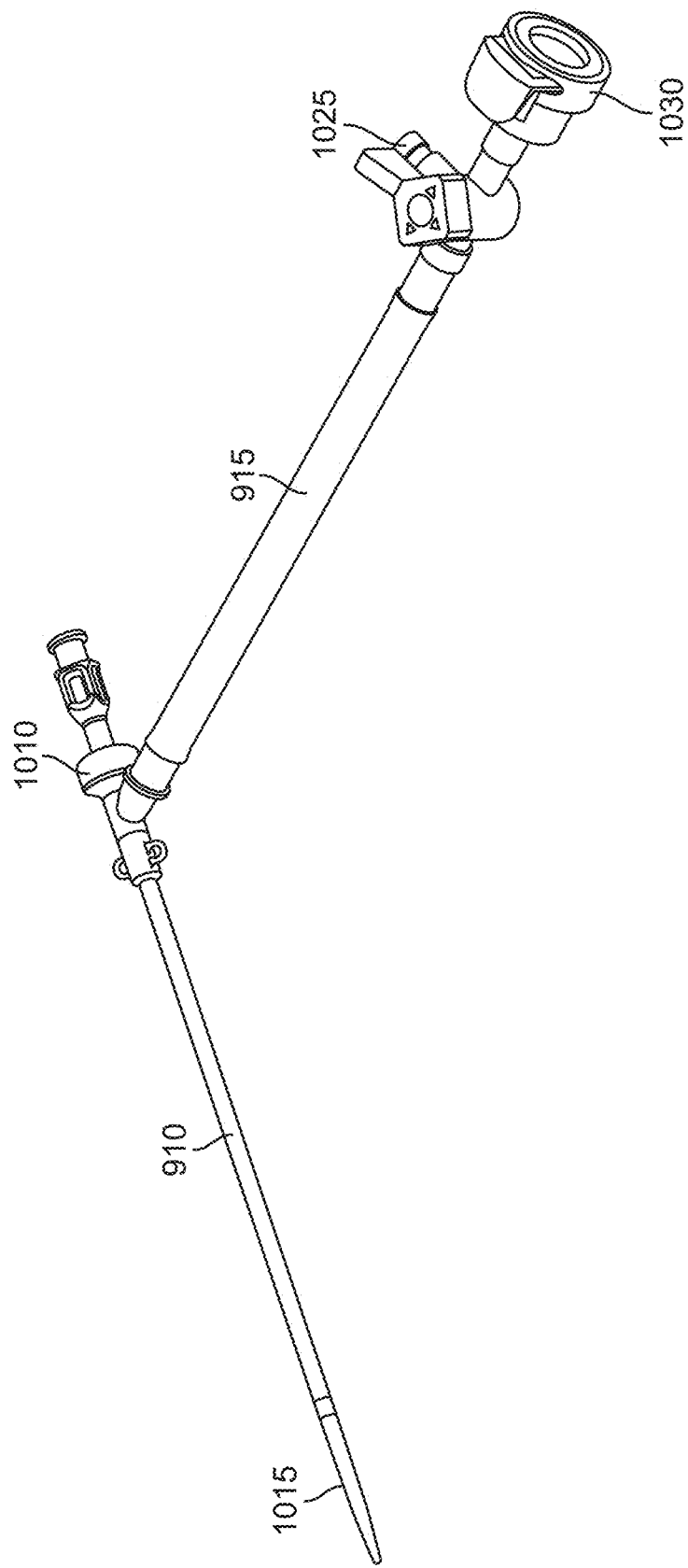

An alternate configuration is shown in FIGS. 10C and 10D. FIG. 10C shows the components of the venous return device 115 including venous return sheath 910, sheath dilator 1015, and sheath guidewire 611. FIG. 10D shows the venous return device 115 as it would be assembled for insertion over the sheath guide wire 611 into a central vein. Once the sheath is inserted into the vein, the dilator and guidewire are removed. The venous sheath can include a hemostasis valve 1010 and flow line 915. A stopcock 1025 on the end of the flow line allows the venous sheath to be flushed via the flow line prior to use. This configuration allows the sheath to be prepped from a single point, as is done with conventional introducer sheaths. Connection to the flow shunt 120 is made with a connector 1030 on the stopcock 1025.

In order to reduce the overall system flow resistance, the arterial access flow line 615 (FIG. 6A) and the venous return flow line 915, and Y-connectors 620 (FIG. 6A) and 1005, can each have a relatively large flow lumen inner diameter, typically being in the range from 2.54 mm (0.100 inch) to 5.08 mm (0.200 inch), and a relatively short length, typically being in the range from 10 cm to 20 cm. The low system flow resistance is desirable since it permits the flow to be maximized during portions of a procedure when the risk of emboli is at its greatest. The low system flow resistance also allows the use of a variable flow resistance for controlling flow in the system, as described in more detail below. The dimensions of the venous return sheath 910 can be generally the same as those described for the arterial access sheath 605 above. In the venous return sheath, an extension for the hemostasis valve 1010 is not required.

Retrograde Shunt

The shunt 120 can be formed of a single tube or multiple, connected tubes that provide fluid communication between the arterial access catheter 110 and the venous return catheter 115 to provide a pathway for retrograde blood flow therebetween. As shown in FIG. 1A, the shunt 120 connects at one end (via connector 127a) to the flow line 615 of the arterial access device 110, and at an opposite end (via connector 127b) to the flow line 915 of the venous return catheter 115.

In an embodiment, the shunt 120 can be formed of at least one tube that communicates with the flow control assembly 125. The shunt 120 can be any structure that provides a fluid pathway for blood flow. The shunt 120 can have a single lumen or it can have multiple lumens. The shunt 120 can be removably attached to the flow control assembly 125, arterial access device 110, and/or venous return device 115. Prior to use, the user can select a shunt 120 with a length that is most appropriate for use with the arterial access location and venous return location. In an embodiment, the shunt 120 can include one or more extension tubes that can be used to vary the length of the shunt 120. The extension tubes can be modularly attached to the shunt 120 to achieve a desired length. The modular aspect of the shunt 120 permits the user to lengthen the shunt 120 as needed depending on the site of venous return. For example, in some patients, the internal jugular vein IJV is small and/or tortuous. The risk of complications at this site may be higher than at some other locations, due to proximity to other anatomic structures. In addition, hematoma in the neck may lead to airway obstruction and/or cerebral vascular complications. Consequently, for such patients it may be desirable to locate the venous return site at a location other than the internal jugular vein IJV, such as the femoral vein. A femoral vein return site may be accomplished percutaneously, with lower risk of serious complication, and also offers an alternative venous access to the central vein if the internal jugular vein IJV is not available. Furthermore, the femoral venous return changes the layout of the reverse flow shunt such that the shunt controls may be located closer to the "working area" of the intervention, where the devices are being introduced and the contrast injection port is located.

Figure 11:
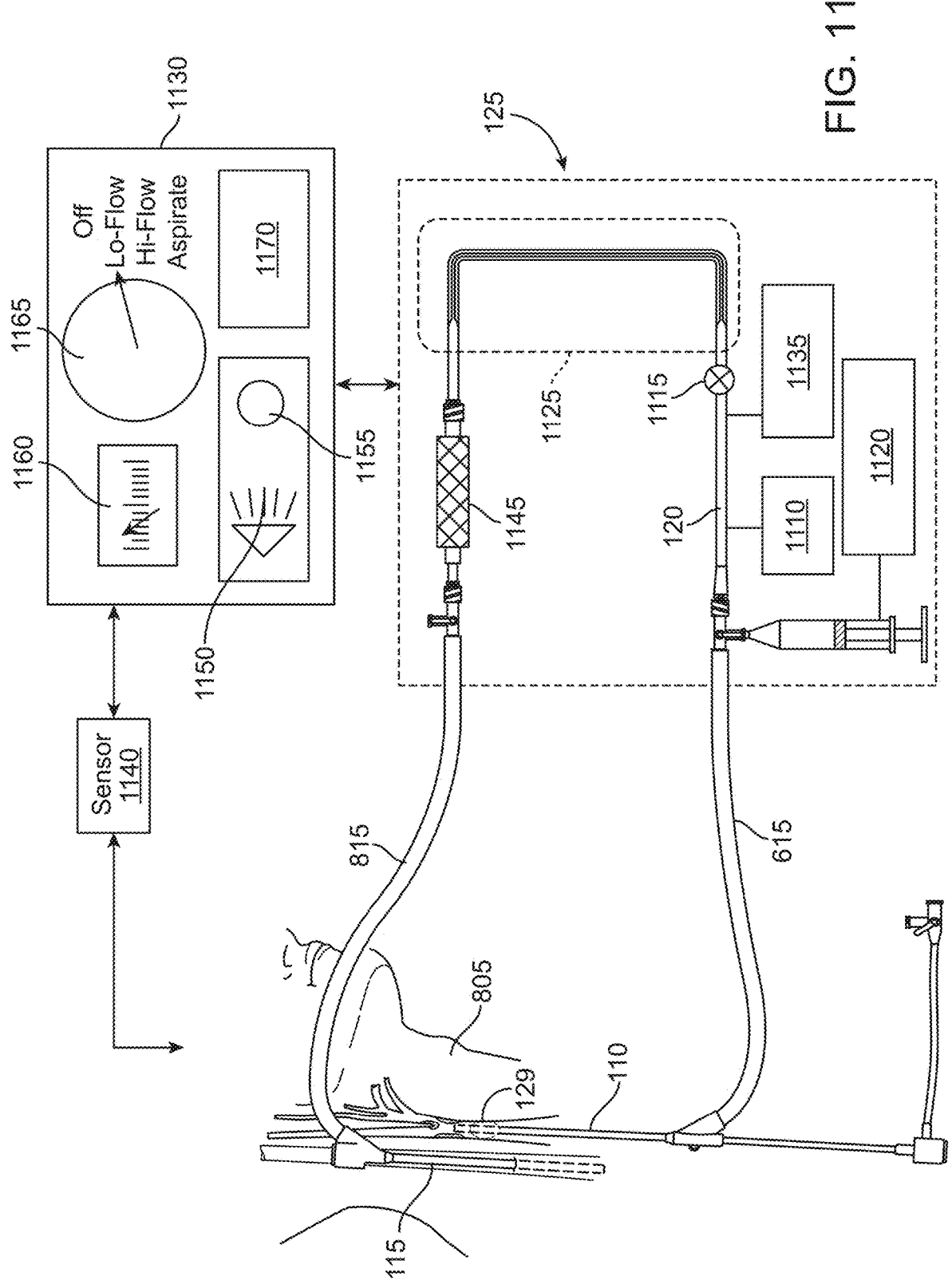
FIG. 11 illustrates the system of FIG. 1 including a flow control assembly.

In an embodiment, the shunt 120 has an internal diameter of 4.76 mm (3/16 inch) and has a length of 40-70 cm. As mentioned, the length of the shunt can be adjusted. In an embodiment, connectors between the shunt and the arterial and/or venous access devices are configured to minimize flow resistance. In an embodiment, the arterial access sheath 110, the retrograde shunt 120, and the venous return sheath 115 are combined to create a low flow resistance arteriovenous AV shunt, as shown in FIGS. 1A-1D. As described above, the connections and flow lines of all these devices are optimized to minimize or reduce the resistance to flow. In an embodiment, the AV shunt has a flow resistance which enables a flow of up to 300 mL/minute when no device is in the arterial sheath 110 and when the AV shunt is connected to a fluid source with the viscosity of blood and a static pressure head of 60 mmHg. The actual shunt resistance may vary depending on the presence or absence of a check valve 1115 or a filter 1145 (as shown in FIG. 11), or the length of the shunt, and may enable a flow of between 150 and 300 mL/min.

When there is a device such as a stent delivery catheter in the arterial sheath, there is a section of the arterial sheath that has increased flow resistance, which in turn increases the flow resistance of the overall AV shunt. This increase in flow resistance has a corresponding reduction in flow. In an embodiment, the Y-arm 620 as shown in FIG. 6A connects the arterial sheath body 605 to the flow line 615 some distance away from the hemostasis valve 625 where the catheter is introduced into the sheath. This distance is set by the length of the proximal extension 610. Thus the section of the arterial sheath that is restricted by the catheter is limited to the length of the sheath body 605. The actual flow restriction will depend on the length and inner diameter of the sheath body 605, and the outer diameter of the catheter. As described above, the sheath length may range from 5 to 15 cm, usually being from 10 cm to 12 cm, and the inner diameter is typically in the range from 7 Fr (1 Fr=0.33 mm), to 10 Fr, usually being 8 Fr. Stent delivery catheters may range from 3.7 Fr. to 5.0 or 6.0 Fr, depending on the size of the stent and the manufacturer. This restriction may further be reduced if the sheath body is designed to increase in inner diameter for the portion not in the vessel (a stepped sheath body), as shown in FIG. 6B. Since flow restriction is proportional to luminal distances to the fourth power, small increases in luminal or annular areas result in large reductions in flow resistance.

Actual flow through the AV shunt when in use will further depend on the cerebral blood pressures and flow resistances of the patient.

Flow Control Assembly—Regulation and Monitoring of Retrograde Flow

The flow control assembly 125 interacts with the retrograde shunt 120 to regulate and/or monitor the retrograde flow rate from the common carotid artery to the venous return site, such as the femoral vein, internal jugular vein, or to the external receptacle 130. In this regard, the flow control assembly 125 enables the user to achieve higher maximum flow rates than existing systems and to also selectively adjust, set, or otherwise modulate the retrograde flow rate. Various mechanisms can be used to regulate the retrograde flow rate, as described more fully below. The flow control assembly 125 enables the user to configure retrograde blood flow in a manner that is suited for various treatment regimens, as described below.

In general, the ability to control the continuous retrograde flow rate allows the physician to adjust the protocol for individual patients and stages of the procedure. The retrograde blood flow rate will typically be controlled over a range from a low rate to a high rate. The high rate can be at least two fold higher than the low rate, typically being at least three fold higher than the low rate, and often being at least five fold higher than the low rate, or even higher. In an embodiment, the high rate is at least three fold higher than the low rate and in another embodiment the high rate is at least six fold higher than the low rate. While it is generally desirable to have a high retrograde blood flow rate to maximize the extraction of emboli from the carotid arteries, the ability of patients to tolerate retrograde blood flow will vary. Thus, by having a system and protocol which allows the retrograde blood flow rate to be easily modulated, the treating physician can determine when the flow rate exceeds the tolerable level for that patient and set the reverse flow rate accordingly. For patients who cannot tolerate continuous high reverse flow rates, the physician can chose to turn on high flow only for brief, critical portions of the procedure when the risk of embolic debris is highest. At short intervals, for example between 15 seconds and 1 minute, patient tolerance limitations are usually not a factor.

In specific embodiments, the continuous retrograde blood flow rate can be controlled at a base line flow rate in the range from 10 ml/min to 200 ml/min, typically from 20 ml/min to 100 ml/min. These flow rates will be tolerable to the majority of patients. Although flow rate is maintained at the base line flow rate during most of the procedure, at times when the risk of emboli release is increased, the flow rate can be increased above the base line for a short duration in order to improve the ability to capture such emboli. For example, the retrograde blood flow rate can be increased above the base line when the stent catheter is being introduced, when the stent is being deployed, pre- and post-dilatation of the stent, removal of the common carotid artery occlusion, and the like.

The flow rate control system can be cycled between a relatively low flow rate and a relatively high flow rate in order to "flush" the carotid arteries in the region of the carotid bifurcation prior to reestablishing antegrade flow. Such cycling can be established with a high flow rate which can be approximately two to six fold greater than the low flow rate, typically being about three fold greater. The cycles can typically have a length in the range from 0.5 seconds to 10 seconds, usually from 2 seconds to 5 seconds, with the total duration of the cycling being in the range from 5 seconds to 60 seconds, usually from 10 seconds to 30 seconds.

FIG. 11 shows an example of the system 100 with a schematic representation of the flow control assembly 125, which is positioned along the shunt 120 such that retrograde blood flow passes through or otherwise communicates with at least a portion of the flow control assembly 125. The flow control assembly 125 can include various controllable mechanisms for regulating and/or monitoring retrograde flow. The mechanisms can include various means of controlling the retrograde flow, including one or more pumps 1110, valves 1115, syringes 1120 and/or a variable resistance component 1125. The flow control assembly 125 can be manually controlled by a user and/or automatically controlled via a controller 1130 to vary the flow through the shunt 120. For example, by varying the flow resistance, the rate of retrograde blood flow through the shunt 120 can be controlled. The controller 1130, which is described in more detail below, can be integrated into the flow control assembly 125 or it can be a separate component that communicates with the components of the flow control assembly 125.

In addition, the flow control assembly 125 can include one or more flow sensors 1135 and/or anatomical data sensors 1140 (described in detail below) for sensing one or more aspects of the retrograde flow. A filter 1145 can be positioned along the shunt 120 for removing emboli before the blood is returned to the venous return site. When the filter 1145 is positioned upstream of the controller 1130, the filter 1145 can prevent emboli from entering the controller 1145 and potentially clogging the variable flow resistance component 1125. It should be appreciated that the various components of the flow control assembly 125 (including the pump 1110, valves 1115, syringes 1120, variable resistance component 1125, sensors 1135/1140, and filter 1145) can be positioned at various locations along the shunt 120 and at various upstream or downstream locations relative to one another. The components of the flow control assembly 125 are not limited to the locations shown in FIG. 11. Moreover, the flow control assembly 125 does not necessarily include all of the components but can rather include various sub-combinations of the components. For example, a syringe could optionally be used within the flow control assembly 125 for purposes of regulating flow or it could be used outside of the assembly for purposes other than flow regulation, such as to introduce fluid such as radiopaque contrast into the artery in an antegrade direction via the shunt 120.

Both the variable resistance component 1125 and the pump 1110 can be coupled to the shunt 120 to control the retrograde flow rate. The variable resistance component 1125 controls the flow resistance, while the pump 1110 provides for positive displacement of the blood through the shunt 120. Thus, the pump can be activated to drive the retrograde flow rather than relying on the perfusion stump pressures of the ECA and ICA and the venous back pressure to drive the retrograde flow. The pump 1110 can be a peristaltic tube pump or any type of pump including a positive displacement pump. The pump 1110 can be activated and deactivated (either manually or automatically via the controller 1130) to selectively achieve blood displacement through the shunt 120 and to control the flow rate through the shunt 120. Displacement of the blood through the shunt 120 can also be achieved in other manners including using the aspiration syringe 1120, or a suction source such as a vacutainer, vaculock syringe, or wall suction may be used. The pump 1110 can communicate with the controller 1130.

One or more flow control valves 1115 can be positioned along the pathway of the shunt. The valve(s) can be manually actuated or automatically actuated (via the controller 1130). The flow control valves 1115 can be, for example one-way valves to prevent flow in the antegrade direction in the shunt 120, check valves, or high pressure valves which would close off the shunt 120, for example during high-pressure contrast injections (which are intended to enter the arterial vasculature in an antegrade direction). In an embodiment, the one-way valves are low flow-resistance valves for example that described in U.S. Pat. No. 5,727,594, or other low resistance valves.

In an embodiment of a shunt with both a filter 1145 and a one-way check valve 1115, the check valve is located down stream of the filter. In this manner, if there is debris traveling in the shunt, it is trapped in the filter before it reaches the check valve. Many check valve configurations include a sealing member that seals against a housing that contains a flow lumen. Debris may have the potential to be trapped between the sealing member and the housing, thus compromising the ability of the valve to seal against backwards pressure.

The controller 1130 communicates with components of the system 100 including the flow control assembly 125 to enable manual and/or automatic regulation and/or monitoring of the retrograde flow through the components of the system 100 (including, for example, the shunt 120, the arterial access device 110, the venous return device 115 and the flow control assembly 125). For example, a user can actuate one or more actuators on the controller 1130 to manually control the components of the flow control assembly 125. Manual controls can include switches or dials or similar components located directly on the controller 1130 or components located remote from the controller 1130 such as a foot pedal or similar device. The controller 1130 can also automatically control the components of the system 100 without requiring input from the user. In an embodiment, the user can program software in the controller 1130 to enable such automatic control. The controller 1130 can control actuation of the mechanical portions of the flow control assembly 125. The controller 1130 can include circuitry or programming that interprets signals generated by sensors 1135/1140 such that the controller 1130 can control actuation of the flow control assembly 125 in response to such signals generated by the sensors.

The representation of the controller 1130 in FIG. 11 is merely exemplary. It should be appreciated that the controller 1130 can vary in appearance and structure. The controller 1130 is shown in FIG. 11 as being integrated in a single housing. This permits the user to control the flow control assembly 125 from a single location. It should be appreciated that any of the components of the controller 1130 can be separated into separate housings. Further, FIG. 11 shows the controller 1130 and flow control assembly 125 as separate housings. It should be appreciated that the controller 1130 and flow control regulator 125 can be integrated into a single housing or can be divided into multiple housings or components.

Flow State Indicator(s)

The controller 1130 can include one or more indicators that provides a visual and/or audio signal to the user regarding the state of the retrograde flow. An audio indication advantageously reminds the user of a flow state without requiring the user to visually check the flow controller 1130. The indicator(s) can include a speaker 1150 and/or a light 1155 or any other means for communicating the state of retrograde flow to the user. The controller 1130 can communicate with one or more sensors of the system to control activation of the indicator. Or, activation of the indicator can be tied directly to the user actuating one of the flow control actuators 1165. The indicator need not be a speaker or a light. The indicator could simply be a button or switch that visually indicates the state of the retrograde flow. For example, the button being in a certain state (such as a pressed or down state) may be a visual indication that the retrograde flow is in a high state. Or, a switch or dial pointing toward a particular labeled flow state may be a visual indication that the retrograde flow is in the labeled state.

The indicator can provide a signal indicative of one or more states of the retrograde flow. In an embodiment, the indicator identifies only two discrete states: a state of "high" flow rate and a state of "low" flow rate. In another embodiment, the indicator identifies more than two flow rates, including a "high" flow rate, a "medium" flow rate, and a "low" rate. The indicator can be configured to identify any quantity of discrete states of the retrograde flow or it can identify a graduated signal that corresponds to the state of the retrograde flow. In this regard, the indicator can be a digital or analog meter 1160 that indicates a value of the retrograde flow rate, such as in ml/min or any other units.

In an embodiment, the indicator is configured to indicate to the user whether the retrograde flow rate is in a state of "high" flow rate or a "low" flow rate. For example, the indicator may illuminate in a first manner (e.g., level of brightness) and/or emit a first audio signal when the flow rate is high and then change to a second manner of illumination and/or emit a second audio signal when the flow rate is low. Or, the indicator may illuminate and/or emit an audio signal only when the flow rate is high, or only when the flow rate is low. Given that some patients may be intolerant of a high flow rate or intolerant of a high flow rate beyond an extended period of time, it can be desirable that the indicator provide notification to the user when the flow rate is in the high state. This would serve as a fail safe feature.

In another embodiment, the indicator provides a signal (audio and/or visual) when the flow rate changes state, such as when the flow rate changes from high to low and/or vice-versa. In another embodiment, the indicator provides a signal when no retrograde flow is present, such as when the shunt 120 is blocked or one of the stopcocks in the shunt 120 is closed.

Flow Rate Actuators

The controller 1130 can include one or more actuators that the user can press, switch, manipulate, or otherwise actuate to regulate the retrograde flow rate and/or to monitor the flow rate. For example, the controller 1130 can include a flow control actuator 1165 (such as one or more buttons, knobs, dials, switches, etc.) that the user can actuate to cause the controller to selectively vary an aspect of the reverse flow. For example, in the illustrated embodiment, the flow control actuator 1165 is a knob that can be turned to various discrete positions each of which corresponds to the controller 1130 causing the system 100 to achieve a particular retrograde flow state. The states include, for example, (a) OFF; (b) LO-FLOW; (c) HI-FLOW; and (d) ASPIRATE. It should be appreciated that the foregoing states are merely exemplary and that different states or combinations of states can be used. The controller 1130 achieves the various retrograde flow states by interacting with one or more components of the system, including the sensor(s), valve(s), variable resistance component, and/or pump(s). It should be appreciated that the controller 1130 can also include circuitry and software that regulates the retrograde flow rate and/or monitors the flow rate such that the user wouldn't need to actively actuate the controller 1130.

The OFF state corresponds to a state where there is no retrograde blood flow through the shunt 120. When the user sets the flow control actuator 1165 to OFF, the controller 1130 causes the retrograde flow to cease, such as by shutting off valves or closing a stop cock in the shunt 120. The LO-FLOW and HI-FLOW states correspond to a low retrograde flow rate and a high retrograde flow rate, respectively. When the user sets the flow control actuator 1165 to LO-FLOW or HI-FLOW, the controller 1130 interacts with components of the flow control regulator 125 including pump(s) 1110, valve(s) 1115 and/or variable resistance component 1125 to increase or decrease the flow rate accordingly. Finally, the ASPIRATE state corresponds to opening the circuit to a suction source, for example a vacutainer or suction unit, if active retrograde flow is desired.

The system can be used to vary the blood flow between various states including an active state, a passive state, an aspiration state, and an off state. The active state corresponds to the system using a means that actively drives retrograde blood flow. Such active means can include, for example, a pump, syringe, vacuum source, etc. The passive state corresponds to when retrograde blood flow is driven by the perfusion stump pressures of the ECA and ICA and possibly the venous pressure. The aspiration state corresponds to the system using a suction source, for example a vacutainer or suction unit, to drive retrograde blood flow. The off state corresponds to the system having zero retrograde blood flow such as the result of closing a stopcock or valve. The low and high flow rates can be either passive or active flow states. In an embodiment, the particular value (such as in ml/min) of either the low flow rate and/or the high flow rate can be predetermined and/or pre-programmed into the controller such that the user does not actually set or input the value. Rather, the user simply selects "high flow" and/or "low flow" (such as by pressing an actuator such as a button on the controller 1130) and the controller 1130 interacts with one or more of the components of the flow control assembly 125 to cause the flow rate to achieve the predetermined high or low flow rate value. In another embodiment, the user sets or inputs a value for low flow rate and/or high flow rate such as into the controller. In another embodiment, the low flow rate and/or high flow rate is not actually set. Rather, external data (such as data from the anatomical data sensor 1140) is used as the basis for affects the flow rate.

The flow control actuator 1165 can be multiple actuators, for example one actuator, such as a button or switch, to switch state from LO-FLOW to HI-FLOW and another to close the flow loop to OFF, for example during a contrast injection where the contrast is directed antegrade into the carotid artery. In an embodiment, the flow control actuator 1165 can include multiple actuators. For example, one actuator can be operated to switch flow rate from low to high, another actuator can be operated to temporarily stop flow, and a third actuator (such as a stopcock) can be operated for aspiration using a syringe. In another example, one actuator is operated to switch to LO-FLOW and another actuator is operated to switch to HI-FLOW. Or, the flow control actuator 1165 can include multiple actuators to switch states from LO-FLOW to HI-FLOW and additional actuators for fine-tuning flow rate within the high flow state and low flow state. Upon switching between LO-FLOW and HI-FLOW, these additional actuators can be used to fine-tune the flow rates within those states. Thus, it should be appreciated that within each state (i.e. high flow state and low flow states) a variety of flow rates can be dialed in and fine-tuned. A wide variety of actuators can be used to achieve control over the state of flow.

The controller 1130 or individual components of the controller 1130 can be located at various positions relative to the patient and/or relative to the other components of the system 100. For example, the flow control actuator 1165 can be located near the hemostasis valve where any interventional tools are introduced into the patient in order to facilitate access to the flow control actuator 1165 during introduction of the tools. The location may vary, for example, based on whether a transfemoral or a transcarotid approach is used, as shown in FIGS. 1 A-C. The controller 1130 can have a wireless connection to the remainder of the system 100 and/or a wired connection of adjustable length to permit remote control of the system 100. The controller 1130 can have a wireless connection with the flow control regulator 125 and/or a wired connection of adjustable length to permit remote control of the flow control regulator 125. The controller 1130 can also be integrated in the flow control regulator 125. Where the controller 1130 is mechanically connected to the components of the flow control assembly 125, a tether with mechanical actuation capabilities can connect the controller 1130 to one or more of the components. In an embodiment, the controller 1130 can be positioned a sufficient distance from the system 100 to permit positioning the controller 1130 outside of a radiation field when fluoroscopy is in use.

The controller 1130 and any of its components can interact with other components of the system (such as the pump(s), sensor(s), shunt, etc) in various manners. For example, any of a variety of mechanical connections can be used to enable communication between the controller 1130 and the system components. Alternately, the controller 1130 can communicate electronically or magnetically with the system components. Electro-mechanical connections can also be used. The controller 1130 can be equipped with control software that enables the controller to implement control functions with the system components. The controller itself can be a mechanical, electrical or electro-mechanical device. The controller can be mechanically, pneumatically, or hydraulically actuated or electromechanically actuated (for example in the case of solenoid actuation of flow control state). The controller 1130 can include a computer, computer processor, and memory, as well as data storage capabilities.

Figure 12A:
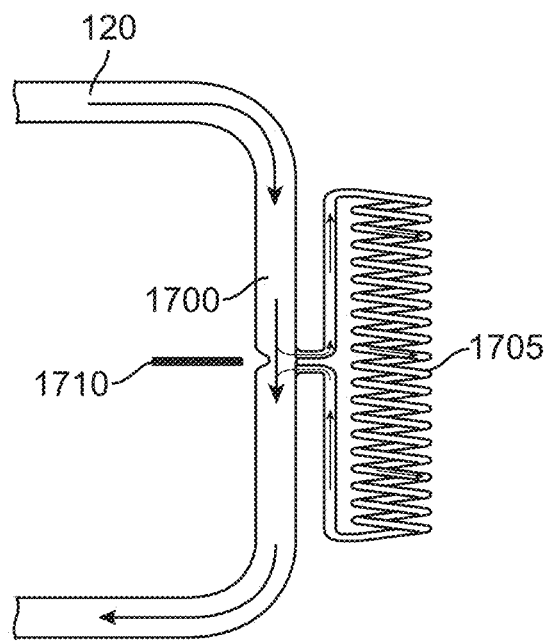
FIGS. 12A-12B illustrate an embodiment of a variable flow resistance component useful in the methods and systems of the present disclosure.
Figure 12B:
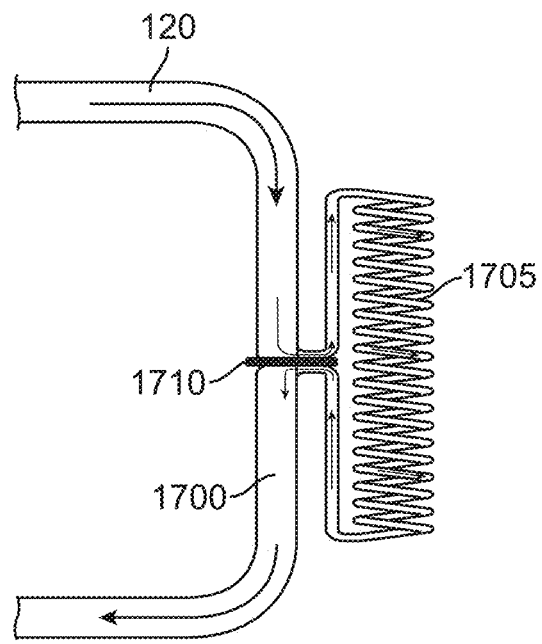

FIG. 11 shows an exemplary embodiment of a variable flow control element 1125. In this embodiment, the flow resistance through shunt 120 may be changed by providing two or more alternative flow paths to create a low and high resistance flow path. As shown in FIG. 12A, the flow through shunt 120 passes through a main lumen 1700 as well as secondary lumen 1705. The secondary lumen 1705 is longer and/or has a smaller diameter than the main lumen 1700. Thus, the secondary lumen 1705 has higher flow resistance than the main lumen 1700. By passing the blood through both these lumens, the flow resistance will be at a minimum. Blood is able to flow through both lumens 1700 and 1705 due to the pressure drop created in the main lumen 1700 across the inlet and outlet of the secondary lumen 1705. This has the benefit of preventing stagnant blood. As shown in FIG. 12B, by blocking flow through the main lumen 1700 of shunt 120, the flow is diverted entirely to the secondary lumen 1705, thus increasing the flow resistance and reducing the blood flow rate. It will be appreciated that additional flow lumens could also be provided in parallel to allow for a three, four, or more discrete flow resistances. The shunt 120 may be equipped with a valve 1710 that controls flow to the main lumen 1700 and the secondary lumen 1705. The valve position may be controlled by an actuator such as a button or switch on the housing of flow controller 125. The embodiment of FIGS. 12A and 12B has an advantage in that this embodiment in that it maintains precise flow lumen sizes even for the lowest flow setting. The secondary flow lumen size can be configured to prevent thrombus from forming under even the lowest flow or prolonged flow conditions. In an embodiment, the inner diameter of the secondary lumen 1705 lumen is 0.063 inches or larger.

In a preferred embodiment, the connectors which connect the elements of the reverse flow system are large bore, quick-connect style connectors. For example, a male large-bore hub 680 on the Y-adaptor 660 of arterial sheath 110, as seen in FIG. 9B, connects to a female counterpart 1320 on the arterial side of flow shunt 120. Similarly, a male large bore connector 1310 on the venous side of flow shunt 120 connects to a female counterpart connector 1310 on the flow line of venous sheath 115, as seen in FIG. 10C. The connections can be standard female and male Luer connectors or other style of tubing connectors.

Sensor(s)

As mentioned, the flow control assembly 125 can include or interact with one or more sensors, which communicate with the system 100 and/or communicate with the patient's anatomy. Each of the sensors can be adapted to respond to a physical stimulus (including, for example, heat, light, sound, pressure, magnetism, motion, etc.) and to transmit a resulting signal for measurement or display or for operating the controller 1130. In an embodiment, the flow sensor 1135 interacts with the shunt 120 to sense an aspect of the flow through the shunt 120, such as flow velocity or volumetric rate of blood flow. The flow sensor 1135 could be directly coupled to a display that directly displays the value of the volumetric flow rate or the flow velocity. Or the flow sensor 1135 could feed data to the controller 1130 for display of the volumetric flow rate or the flow velocity.

The type of flow sensor 1135 can vary. The flow sensor 1135 can be a mechanical device, such as a paddle wheel, flapper valve, rolling ball, or any mechanical component that responds to the flow through the shunt 120. Movement of the mechanical device in response to flow through the shunt 120 can serve as a visual indication of fluid flow and can also be calibrated to a scale as a visual indication of fluid flow rate. The mechanical device can be coupled to an electrical component. For example, a paddle wheel can be positioned in the shunt 120 such that fluid flow causes the paddle wheel to rotate, with greater rate of fluid flow causing a greater speed of rotation of the paddle wheel. The paddle wheel can be coupled magnetically to a Hall-effect sensor to detect the speed of rotation, which is indicative of the fluid flow rate through the shunt 120.

In an embodiment, the flow sensor 1135 is an ultrasonic or electromagnetic, or electro-optic flow meter, which allows for blood flow measurement without contacting the blood through the wall of the shunt 120. An ultrasonic or electromagnetic flow meter can be configured such that it does not have to contact the internal lumen of the shunt 120. In an embodiment, the flow sensor 1135 at least partially includes a Doppler flow meter, such as a Transonic flow meter, that measures fluid flow through the shunt 120. In another embodiment, the flow sensor 1135 measures pressure differential along the flow line to determine flow. It should be appreciated that any of a wide variety of sensor types can be used including an ultrasound flow meter and transducer. Moreover, the system can include multiple sensors.

The system 100 is not limited to using a flow sensor 1135 that is positioned in the shunt 120 or a sensor that interacts with the venous return device 115 or the arterial access device 110. For example, an anatomical data sensor 1140 can communicate with or otherwise interact with the patient's anatomy such as the patient's neurological anatomy. In this manner, the anatomical data sensor 1140 can sense a measurable anatomical aspect that is directly or indirectly related to the rate of retrograde flow from the carotid artery. For example, the anatomical data sensor 1140 can measure blood flow conditions in the brain, for example the flow velocity in the middle cerebral artery, and communicate such conditions to a display and/or to the controller 1130 for adjustment of the retrograde flow rate based on predetermined criteria. In an embodiment, the anatomical data sensor 1140 comprises a transcranial Doppler ultrasonography (TCD), which is an ultrasound test that uses reflected sound waves to evaluate blood as it flows through the brain. Use of TCD results in a TCD signal that can be communicated to the controller 1130 for controlling the retrograde flow rate to achieve or maintain a desired TCD profile. The anatomical data sensor 1140 can be based on any physiological measurement, including reverse flow rate, blood flow through the middle cerebral artery, TCD signals of embolic particles, or other neuromonitoring signals.

In an embodiment, the system 100 comprises a closed-loop control system. In the closed-loop control system, one or more of the sensors (such as the flow sensor 1135 or the anatomical data sensor 1140) senses or monitors a predetermined aspect of the system 100 or the anatomy (such as, for example, reverse flow rate and/or neuromonitoring signal). The sensor(s) feed relevant data to the controller 1130, which continuously adjusts an aspect of the system as necessary to maintain a desired retrograde flow rate. The sensors communicate feedback on how the system 100 is operating to the controller 1130 so that the controller 1130 can translate that data and actuate the components of the flow control regulator 125 to dynamically compensate for disturbances to the retrograde flow rate. For example, the controller 1130 may include software that causes the controller 1130 to signal the components of the flow control assembly 125 to adjust the flow rate such that the flow rate is maintained at a constant state despite differing blood pressures from the patient. In this embodiment, the system 100 need not rely on the user to determine when, how long, and/or what value to set the reverse flow rate in either a high or low state. Rather, software in the controller 1130 can govern such factors. In the closed loop system, the controller 1130 can control the components of the flow control assembly 125 to establish the level or state of retrograde flow (either analog level or discreet state such as high, low, baseline, medium, etc.) based on the retrograde flow rate sensed by the sensor 1135.

In an embodiment, the anatomical data sensor 1140 (which measures a physiologic measurement in the patient) communicates a signal to the controller 1130, which adjusts the flow rate based on the signal. For example the physiological measurement may be based on flow velocity through the MCA, TCD signal, or some other cerebral vascular signal. In the case of the TCD signal, TCD may be used to monitor cerebral flow changes and to detect microemboli. The controller 1130 may adjust the flow rate to maintain the TCD signal within a desired profile. For example, the TCD signal may indicate the presence of microemboli ("TCD hits") and the controller 1130 can adjust the retrograde flow rate to maintain the TCD hits below a threshold value of hits. (See, Ribo, et al., "Transcranial Doppler Monitoring of Transcervical Carotid Stenting with Flow Reversal Protection: A Novel Carotid Revascularization Technique", *Stroke* 2006, 37, 2846-2849; Shekel, et al., "Experience of 500 Cases of Neurophysiological Monitoring in Carotid Endarterectomy", *Acta Neurochir*, 2007, 149:681-689, which are incorporated by reference in their entirety.

In the case of the MCA flow, the controller 1130 can set the retrograde flow rate at the "maximum" flow rate that is tolerated by the patient, as assessed by perfusion to the brain. The controller 1130 can thus control the reverse flow rate to optimize the level of protection for the patient without relying on the user to intercede. In another embodiment, the feedback is based on a state of the devices in the system 100 or the interventional tools being used. For example, a sensor may notify the controller 1130 when the system 100 is in a high risk state, such as when an interventional catheter is positioned in the sheath 605. The controller 1130 then adjusts the flow rate to compensate for such a state.

The controller 1130 can be used to selectively augment the retrograde flow in a variety of manners. For example, it has been observed that greater reverse flow rates may cause a resultant greater drop in blood flow to the brain, most importantly the ipsilateral MCA, which may not be compensated enough with collateral flow from the Circle of Willis. Thus a higher reverse flow rate for an extended period of time may lead to conditions where the patient's brain is not getting enough blood flow, leading to patient intolerance as exhibited by neurologic symptoms. Studies show that MCA blood velocity less than 10 cm/sec is a threshold value below which patient is at risk for neurological blood deficit. There are other markers for monitoring adequate perfusion to the brains, such as EEG signals. However, a high flow rate may be tolerated even up to a complete stoppage of MCA flow for a short period, up to about 15 seconds to 1 minute.

Thus, the controller 1130 can optimize embolic debris capture by automatically increasing the reverse flow only during limited time periods which correspond to periods of heightened risk of emboli generation during a procedure. These periods of heightened risk include the period of time while an interventional device (such as a dilatation balloon for pre or post stenting dilatation or a stent delivery device) crosses the plaque P. Another period is during an interventional maneuver such as deployment of the stent or inflation and deflation of the balloon pre- or post-dilatation. A third period is during injection of contrast for angiographic imaging of treatment area. During lower risk periods, the controller can cause the reverse flow rate to revert to a lower, baseline level. This lower level may correspond to a low reverse flow rate in the ICA, or even slight antegrade flow in those patients with a high ECA to ICA perfusion pressure ratio.

In a flow regulation system where the user manually sets the state of flow, there is risk that the user may not pay attention to the state of retrograde flow (high or low) and accidentally keep the circuit on high flow. This may then lead to adverse patient reactions. In an embodiment, as a safety mechanism, the default flow rate is the low flow rate. This serves as a fail safe measure for patient's that are intolerant of a high flow rate. In this regard, the controller 1130 can be biased toward the default rate such that the controller causes the system to revert to the low flow rate after passage of a predetermined period of time of high flow rate. The bias toward low flow rate can be achieved via electronics or software, or it can be achieved using mechanical components, or a combination thereof. In an embodiment, the flow control actuator 1165 of the controller 1130 and/or valve(s) 1115 and/or pump(s) 1110 of the flow control regulator 125 are spring loaded toward a state that achieves a low flow rate. The controller 1130 is configured such that the user may over-ride the controller 1130 such as to manually cause the system to revert to a state of low flow rate if desired.

In another safety mechanism, the controller 1130 includes a timer 1170 (FIG. 11) that keeps time with respect to how long the flow rate has been at a high flow rate. The controller 1130 can be programmed to automatically cause the system 100 to revert to a low flow rate after a predetermined time period of high flow rate, for example after 15, 30, or 60 seconds or more of high flow rate. After the controller reverts to the low flow rate, the user can initiate another predetermined period of high flow rate as desired. Moreover, the user can override the controller 1130 to cause the system 100 to move to the low flow rate (or high flow rate) as desired.

In an exemplary procedure, embolic debris capture is optimized while not causing patient tolerance issues by initially setting the level of retrograde flow at a low rate, and then switching to a high rate for discreet periods of time during critical stages in the procedure. Alternately, the flow rate is initially set at a high rate, and then verifying patient tolerance to that level before proceeding with the rest of the procedure. If the patient shows signs of intolerance, the retrograde flow rate is lowered. Patient tolerance may be determined automatically by the controller based on feedback from the anatomical data sensor 1140 or it may be determined by a user based on patient observation. The adjustments to the retrograde flow rate may be performed automatically by the controller or manually by the user. Alternately, the user may monitor the flow velocity through the middle cerebral artery (MCA), for example using TCD, and then to set the maximum level of reverse flow which keeps the MCA flow velocity above the threshold level. In this situation, the entire procedure may be done without modifying the state of flow. Adjustments may be made as needed if the MCA flow velocity changes during the course of the procedure, or the patient exhibits neurologic symptoms.

Exemplary Methods of Use

Figure 14C:
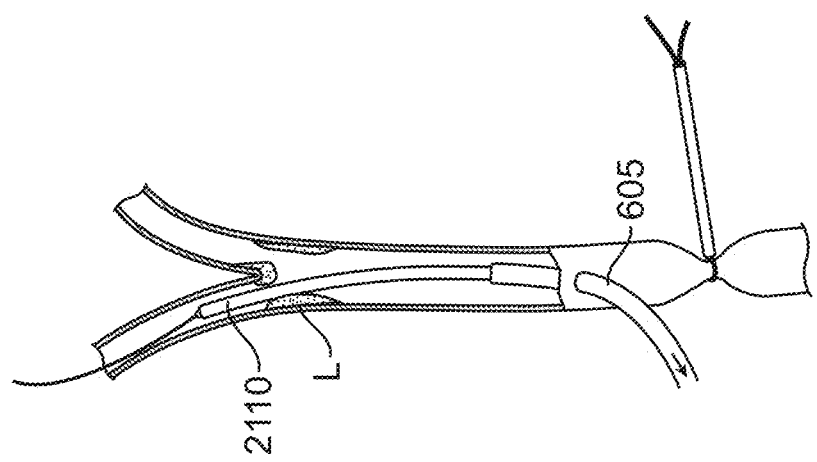
FIGS. 14A-14E illustrate the exemplary blood flow paths during a procedure for implanting a stent at the carotid bifurcation in accordance with the principles of the present disclosure.
Figure 14B:
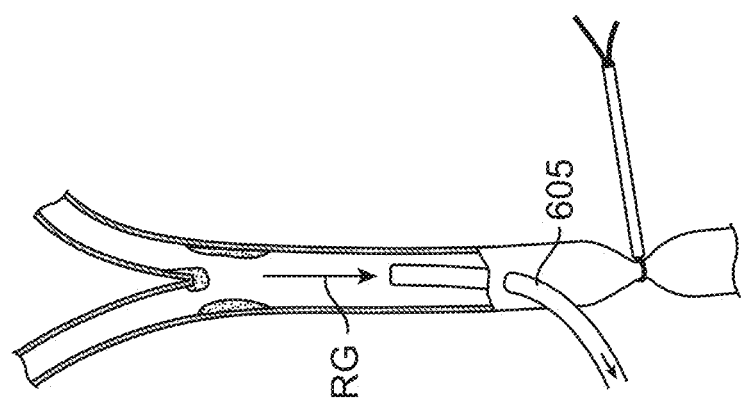
Figure 14A:
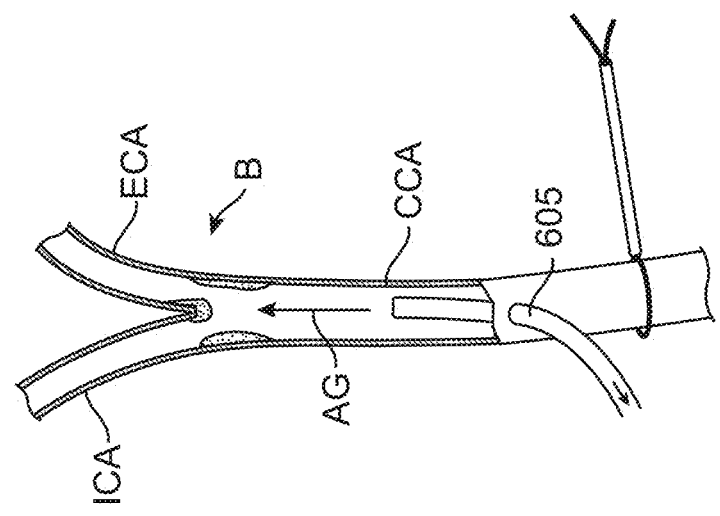

Referring now to FIGS. 14A-14E, flow through the carotid artery bifurcation at different stages of the methods of the present disclosure will be described. Initially, as shown in FIG. 14A, the distal sheath 605 of the arterial access device 110 is introduced into the common carotid artery CCA. As mentioned, entry into the common carotid artery CCA can be via a transcarotid or transfemoral approach, and can be either a direct surgical cut-down or percutaneous access. After the sheath 605 of the arterial access device 110 has been introduced into the common carotid artery CCA, the blood flow will continue in antegrade direction AG with flow from the common carotid artery entering both the internal carotid artery ICA and the external carotid artery ECA, as shown in FIG. 14A.

The venous return device 115 is then inserted into a venous return site, such as the internal jugular vein IJV (not shown in FIGS. 14A-14E) or femoral vein. The shunt 120 is used to connect the flow lines 615 and 915 of the arterial access device 110 and the venous return device 115, respectively (as shown in FIG. 1A). In this manner, the shunt 120 provides a passageway for retrograde flow from the atrial access device 110 to the venous return device 115. In another embodiment, the shunt 120 connects to an external receptacle 130 rather than to the venous return device 115, as shown in FIG. 1C.

Once all components of the system are in place and connected, flow through the common carotid artery CCA is stopped, typically by use of a tourniquet 2105 or other external vessel occlusion device to occlude the common carotid artery CCA. In an alternative embodiment, an occlusion element 129 is located on the distal end of arterial access device 110. Alternately, the occlusion element 129 is introduced on second occlusion device 112 separate from the distal sheath 605 of the arterial access device 110, as shown in FIG. 2B. The ECA may also be occluded with a separate occlusion element, either on the same device 110 or on a separate occlusion device.

At that point retrograde flow RG from the external carotid artery ECA and internal carotid artery ICA will begin and will flow through the sheath 605, the flow line 615, the shunt 120, and into the venous return device 115 via the flow line 915. The flow control assembly 125 regulates the retrograde flow as described above. FIG. 14B shows the occurrence of retrograde flow RG. While the retrograde flow is maintained, a stent delivery catheter 2110 is introduced into the sheath 605, as shown in FIG. 14C. The stent delivery catheter 2110 is introduced into the sheath 605 through the hemostasis valve 615 and the proximal extension 610 (not shown in FIGS. 14A-14E) of the arterial access device 110. The stent delivery catheter 2110 is advanced into the internal carotid artery ICA and a stent 2115 deployed at the bifurcation B, as shown in FIG. 14D.

The rate of retrograde flow can be increased during periods of higher risk for emboli generation for example while the stent delivery catheter 2110 is being introduced and optionally while the stent 2115 is being deployed. The rate of retrograde flow can be increased also during placement and expansion of balloons for dilatation prior to or after stent deployment. An atherectomy can also be performed before stenting under retrograde flow.

Still further optionally, after the stent 2115 has been expanded, the bifurcation B can be flushed by cycling the retrograde flow between a low flow rate and high flow rate. The region within the carotid arteries where the stent has been deployed or other procedure performed may be flushed with blood prior to reestablishing normal blood flow. In particular, while the common carotid artery remains occluded, a balloon catheter or other occlusion element may be advanced into the internal carotid artery and deployed to fully occlude that artery. The same maneuver may also be used to perform a post-deployment stent dilatation, which is typically done currently in self-expanding stent procedures. Flow from the common carotid artery and into the external carotid artery may then be reestablished by temporarily opening the occluding means present in the artery. The resulting flow will thus be able to flush the common carotid artery which saw slow, turbulent, or stagnant flow during carotid artery occlusion into the external carotid artery. In addition, the same balloon may be positioned distally of the stent during reverse flow and forward flow then established by temporarily relieving occlusion of the common carotid artery and flushing. Thus, the flushing action occurs in the stented area to help remove loose or loosely adhering embolic debris in that region.

Optionally, while flow from the common carotid artery continues and the internal carotid artery remains blocked, measures can be taken to further loosen emboli from the treated region. For example, mechanical elements may be used to clean or remove loose or loosely attached plaque or other potentially embolic debris within the stent, thrombolytic or other fluid delivery catheters may be used to clean the area, or other procedures may be performed. For example, treatment of in-stent restenosis using balloons, atherectomy, or more stents can be performed under retrograde flow. In another example, the occlusion balloon catheter may include flow or aspiration lumens or channels which open proximal to the balloon. Saline, thrombolytics, or other fluids may be infused and/or blood and debris aspirated to or from the treated area without the need for an additional device. While the emboli thus released will flow into the external carotid artery, the external carotid artery is generally less sensitive to emboli release than the internal carotid artery. By prophylactically removing potential emboli which remain, when flow to the internal carotid artery is reestablished, the risk of emboli release is even further reduced. The emboli can also be released under retrograde flow so that the emboli flows through the shunt 120 to the venous system, a filter in the shunt 120, or the receptacle 130.

Figure 14E:
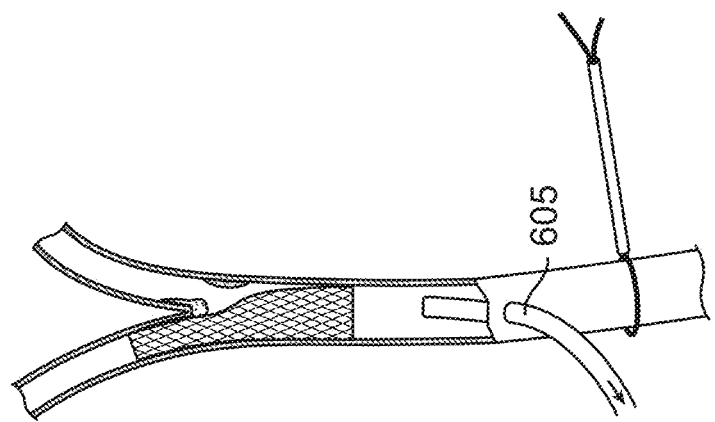
Figure 14D:
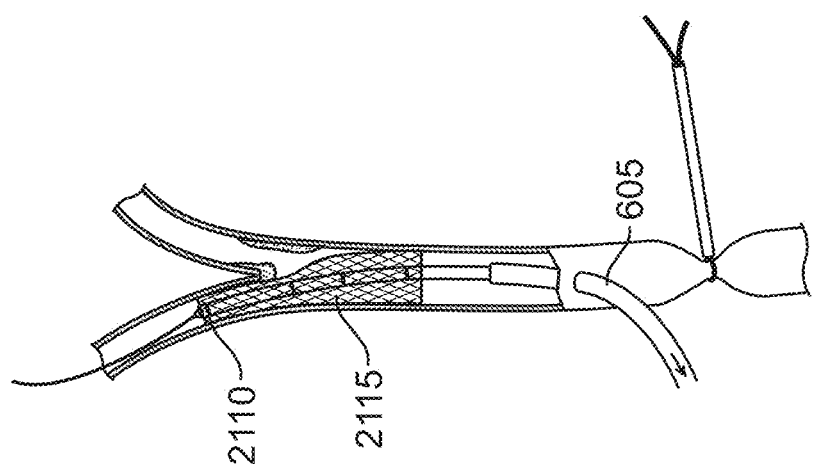

After the bifurcation has been cleared of emboli, the occlusion element 129 or alternately the tourniquet 2105 can be released, reestablishing antegrade flow, as shown in FIG. 14E. The sheath 605 can then be removed.

A self-closing element may be deployed about the penetration in the wall of the common carotid artery prior to withdrawing the sheath 605 at the end of the procedure. Usually, the self-closing element will be deployed at or near the beginning of the procedure, but optionally, the self-closing element could be deployed as the sheath is being withdrawn, often being released from a distal end of the sheath onto the wall of the common carotid artery. Use of the self-closing element is advantageous since it affects substantially the rapid closure of the penetration in the common carotid artery as the sheath is being withdrawn. Such rapid closure can reduce or eliminate unintended blood loss either at the end of the procedure or during accidental dislodgement of the sheath. In addition, such a self-closing element may reduce the risk of arterial wall dissection during access. Further, the self-closing element may be configured to exert a frictional or other retention force on the sheath during the procedure. Such a retention force is advantageous and can reduce the chance of accidentally dislodging the sheath during the procedure. A self-closing element eliminates the need for vascular surgical closure of the artery with suture after sheath removal, reducing the need for a large surgical field and greatly reducing the surgical skill required for the procedure.

The disclosed systems and methods may employ a wide variety of self-closing elements, typically being mechanical elements which include an anchor portion and a self-closing portion. The anchor portion may comprise hooks, pins, staples, clips, tine, suture, or the like, which are engaged in the exterior surface of the common carotid artery about the penetration to immobilize the self-closing element when the penetration is fully open. The self-closing element may also include a spring-like or other self-closing portion which, upon removal of the sheath, will close the anchor portion in order to draw the tissue in the arterial wall together to provide closure. Usually, the closure will be sufficient so that no further measures need be taken to close or seal the penetration. Optionally, however, it may be desirable to provide for supplemental sealing of the self-closing element after the sheath is withdrawn. For example, the self-closing element and/or the tissue tract in the region of the element can be treated with hemostatic materials, such as bioabsorbable polymers, collagen plugs, glues, sealants, dotting factors, or other clot-promoting agents. Alternatively, the tissue or self-closing element could be sealed using other sealing protocols, such as electrocautery, suturing, clipping, stapling, or the like. In another method, the self-closing element will be a self-sealing membrane or gasket material which is attached to the outer wall of the vessel with clips, glue, bands, or other means. The self-sealing membrane may have an inner opening such as a slit or cross cut, which would be normally closed against blood pressure. Any of these self-closing elements could be designed to be placed in an open surgical procedure, or deployed percutaneously.

In another embodiment, carotid artery stenting may be performed after the sheath is placed and an occlusion balloon catheter deployed in the external carotid artery. The stent having a side hole or other element intended to not block the ostium of the external carotid artery may be delivered through the sheath with a guidewire or a shaft of an external carotid artery occlusion balloon received through the side hole. Thus, as the stent is advanced, typically by a catheter being introduced over a guidewire which extends into the internal carotid artery, the presence of the catheter shaft in the side hole will ensure that the side hole becomes aligned with the ostium to the external carotid artery as the stent is being advanced. When an occlusion balloon is deployed in the external carotid artery, the side hole prevents trapping the external carotid artery occlusion balloon shaft with the stent which is a disadvantage of the other flow reversal systems. This approach also avoids "jailing" the external carotid artery, and if the stent is covered with a graft material, avoids blocking flow to the external carotid artery.

In another embodiment, stents are placed which have a shape which substantially conforms to any preexisting angle between the common carotid artery and the internal carotid artery. Due to significant variation in the anatomy among patients, the bifurcation between the internal carotid artery and the external carotid artery may have a wide variety of angles and shapes. By providing a family of stents having differing geometries, or by providing individual stents which may be shaped by the physician prior to deployment, the physician may choose a stent which matches the patient's particular anatomy prior to deployment. The patient's anatomy may be determined using angiography or by other conventional means. As a still further alternative, the stent may have sections of articulation. These stents may be placed first and then articulated in situ in order to match the angle of bifurcation between a common carotid artery and internal carotid artery. Stents may be placed in the carotid arteries, where the stents have a sidewall with different density zones.

In another embodiment, a stent may be placed where the stent is at least partly covered with a graft material at either or both ends. Generally, the stent will be free from graft material and the middle section of the stent which will be deployed adjacent to the ostium to the external carotid artery to allow blood flow from the common carotid artery into the external carotid artery.

In another embodiment, a stent delivery system can be optimized for transcervical transcarotid access by making them shorter and/or more rigid than systems designed for transfemoral access. These changes will improve the ability to torque and position the stent accurately during deployment. In addition, the stent delivery system can be designed to align the stent with the ostium of the external carotid artery, either by using the external carotid occlusion balloon or a separate guide wire in the external carotid artery, which is especially useful with stents with sideholes or for stents with curves, bends, or angulation where orientation is critical.

In certain embodiments, the shunt is fixedly connected to the arterial access sheath and the venous return sheath so that the entire assembly of the replaceable flow assembly and sheaths may be disposable and replaceable as a unit. In other instances, the flow control assembly may be removably attached to either or both of the sheaths.

In an embodiment, the user first determines whether any periods of heightened risk of emboli generation may exist during the procedure. As mentioned, some exemplary periods of heightened risk include (1) during periods when the plaque P is being crossed by a device; (2) during an interventional procedure, such as during delivery of a stent or during inflation or deflation of a balloon catheter or guidewire; (3) during injection of contrast. The foregoing are merely examples of periods of heightened risk. During such periods, the user sets the retrograde flow at a high rate for a discreet period of time. At the end of the high risk period, or if the patient exhibits any intolerance to the high flow rate, then the user reverts the flow state to baseline flow. If the system has a timer, the flow state automatically reverts to baseline flow after a set period of time. In this case, the user may re-set the flow state to high flow if the procedure is still in a period of heightened embolic risk.

In another embodiment, if the patient exhibits an intolerance to the presence of retrograde flow, then retrograde flow is established only during placement of a filter in the ICA distal to the plaque P. Retrograde flow is then ceased while an interventional procedure is performed on the plaque P. Retrograde flow is then re-established while the filter is removed. In another embodiment, a filter is placed in the ICA distal of the plaque P and retrograde flow is established while the filter is in place. This embodiment combines the use of a distal filter with retrograde flow.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method for treating a carotid artery, comprising:
    positioning an arterial access device having a distal sheath into a common carotid artery through an access location in a neck of a patient, the arterial access device comprising:
        a distal sheath adapted to be introduced into a carotid artery through a wall of the carotid artery, the sheath having a lumen extending between a distal opening and a proximal opening;
        wherein the distal sheath includes a material that defines a plurality of spaces evenly distributed and uninterrupted along at least a portion of a length of the distal sheath; and
        wherein the distal sheath includes at least one fenestration aligned with at least one of the spaces defined by the material;
    occluding blood flow at an occlusion location of the common carotid artery to establish retrograde blood flow through the common carotid artery such that blood flows into the lumen of the arterial access device, wherein the occlusion location is located proximal of the distal opening so as to form a zone between the occlusion location and the distal opening;
    wherein the blood flows into the distal sheath via at least one of the distal opening and the at least one fenestration.

2. The method of claim 1, wherein the distal sheath includes a removable stopper member that covers a portion of a distal section of the distal sheath such that a portion of the distal section of the distal sheath is covered by the stopper member and a portion of the distal section of the distal sheath is exposed, wherein the stopper member, when coupled to the distal sheath, limits insertion of the distal sheath into the carotid artery to the exposed portion, and further comprising:
    inserting no more than the exposed portion of the distal sheath into the common carotid artery.

3. The method of claim 2, wherein the at least one fenestration is located entirely within the exposed portion of the distal sheath.

4. The method of claim 1, wherein the zone is a static zone.

5. The method of claim 1, further comprising positioning the distal sheath so that at least one fenestration is positioned in the zone.

6. The method of claim 1, wherein occluding blood flow at an occlusion location comprises applying a vascular clamp at the occlusion location.

7. The method of claim 1, wherein occluding blood flow at an occlusion location comprises expanding a balloon at the occlusion location.

8. The method of claim 1, further comprising making a transcervical incision to expose a region of the common carotid artery at the access location.

9. The method of claim 1, wherein at least one fenestration of the plurality of fenestrations is positioned external to the common carotid artery, and further comprising blocking the at least one fenestration positioned external to the common carotid artery to prevent leakage.

10. The method of claim 1, further comprising placing a stent in an artery via the arterial access device.

* * * * *